(12) United States Patent
Marconi

(10) Patent No.: US 11,899,015 B1
(45) Date of Patent: Feb. 13, 2024

(54) CHIMERIC RECOMBINANT PROTEINS AND RECOMBINANT PROTEIN PANELS FOR THE DIAGNOSIS OF LYME DISEASE IN ANIMALS AND HUMANS

(71) Applicant: VIRGINIA COMMONWEALTH UNIVERSITY, Richmond, VA (US)

(72) Inventor: Richard Marconi, Richmond, VA (US)

(73) Assignee: VIRGINIA COMMONWEALTH UNIVERSITY, Richmond, VA (US)

( * ) Notice: Subject to any disclaimer, the term of this patent is extended or adjusted under 35 U.S.C. 154(b) by 0 days.

(21) Appl. No.: 18/049,022

(22) Filed: Oct. 24, 2022

(51) Int. Cl.
*G01N 33/569* (2006.01)
*C12Q 1/6883* (2018.01)
*C12Q 1/689* (2018.01)
*C07K 14/20* (2006.01)

(52) U.S. Cl.
CPC ........ *G01N 33/56911* (2013.01); *C07K 14/20* (2013.01); *C12Q 1/689* (2013.01); *C12Q 1/6883* (2013.01); *C07K 2319/21* (2013.01); *G01N 2333/20* (2013.01)

(58) Field of Classification Search
None
See application file for complete search history.

(56) References Cited

U.S. PATENT DOCUMENTS

| | | |
|---|---|---|
| 2005/0147999 A1 | 7/2005 | Choi et al. |
| 2008/0013466 A1 | 6/2008 | Reed |
| 2011/0117636 A1 | 5/2011 | Bae et al. |
| 2017/0059566 A1 | 3/2017 | Reed et al. |
| 2018/0149648 A1 | 5/2018 | Lukinova et al. |

FOREIGN PATENT DOCUMENTS

| | | |
|---|---|---|
| RU | 2514230 C1 | 4/2014 |
| WO | 2018217897 A1 | 11/2018 |

*Primary Examiner* — Kagnew H Gebreyesus
(74) *Attorney, Agent, or Firm* — WCF IP

(57) ABSTRACT

Chimeric recombinant proteins for the detection of infection by *Borreliella* and/or diagnosis of Lyme disease are provided. Methods and devices for conducting immunoassays with the chimeric recombinant proteins are also provided.

3 Claims, 8 Drawing Sheets
Specification includes a Sequence Listing.

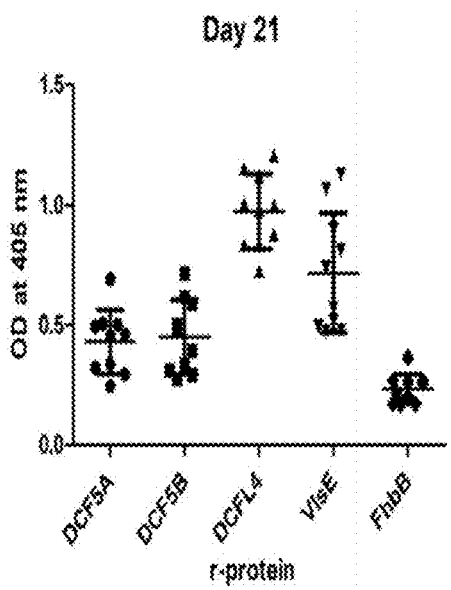 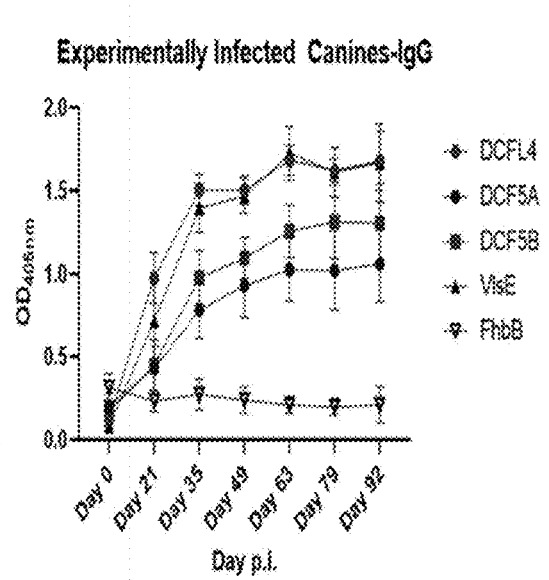
Figure 9A                    Figure 9B
Figure 10

CHIMERIC RECOMBINANT PROTEINS AND RECOMBINANT PROTEIN PANELS FOR THE DIAGNOSIS OF LYME DISEASE IN ANIMALS AND HUMANS

FIELD OF THE INVENTION

The disclosure generally relates to diagnostics for diseases caused by *Borreliella burgdorferi* and related species in mammals, such as Lyme disease, also referred to as Lyme Borreliosis. In particular, the invention provides chimeric recombinant proteins comprising *Borreliella* proteins, or variants thereof, that are highly specific and sensitive when used to detect anti-*Borreliella* antibodies.

BACKGROUND OF THE INVENTION

Lyme disease is the most common arthropod-borne disease in North America and Europe. It is caused by the spirochetes *Borreliella burgdorferi*, *B. garinii*, *B. mayonii*, *B. myiamotoi*, *B. bissetiae*, *B. lanei*, *B. bavariensis*, *B. afzelii* and several other taxonomically related species. In 2014, the bacterial species that cause Lyme disease were reclassified and assigned a new genus name (*Borreliella*). We collectively refer to the *Borreliella* species that cause Lyme disease as the Lyme disease spirochetes. Transmission of Lyme disease spirochetes to mammals occurs through the bite of infected *Ixodes* ticks [Burgdorfer et al, 1982, Benach et al., 1983]. Considerable morbidity is associated with Lyme disease and there are areas in the United States, Europe and the northern hemisphere where 3% or more of the population is infected annually [Fahrer et al., 1991]. Infection results in a multi-systemic inflammatory disease with early-stage symptoms that may include erythema migrans, low-grade fever, arthralgia, myalgia, and headache [Steere et al., 1977a]. Late-stage clinical manifestations can be severe and may include in part, arthritis [Steere et al., 1977a; Eiffert et al., 1998; Steere et al., 2004], carditis [Asch et al., 1994; Nagi et al., 1996 Barthold et al., 1991] and neurological complications [Nachman and Pontrelli, 2003; Coyle and Schutzer 2002]. In addition, Lyme disease has significant socio-economic costs, manifested by reductions in outdoor recreational and social activities due to concerns about tick exposure.

Detection of antibodies to individual proteins is the most common means of diagnosing Lyme disease and many other bacterial, viral and parasitic infections. Infection with Lyme disease spirochetes triggers antibody responses to several proteins. Unfortunately, heretofore no individual protein, or combination of proteins has proven successful for detecting Lyme disease spirochete-directed antibodies with high specificity and sensitivity.

SUMMARY

The present disclosure describes an exhaustive analysis of antibody responses that develop during Lyme disease infection and the resulting design, production and testing of "chimeric" recombinant proteins that comprise a plurality of different antigenic *Borreliella* proteins or variants or peptide segments thereof. In some aspects, 3 or 4 different *Borreliella* proteins (selected from, for example, DbpA, DbpB, BBK19, BBK53, VlsE, BBA73 and BB0238, and/or variants or peptide segments thereof) were used to make the chimeras including the chimeras referred to herein as HDFL4, DCFL4, and DCFL3a. When tested, the chimeras proved to exhibit high specificity and sensitivity in Lyme disease diagnostic assays in humans and animals. Studies in canines revealed that the chimeric proteins do not yield false positives in vaccinated dogs and can detect infection shortly after exposure to infected *Ixodes* ticks. Advantageously, studies in humans have demonstrated high sensitivity and specificity using both ELISA and lateral flow (rapid test) based assays. The chimeric proteins are thus useful as diagnostic tools to identify individuals and/or animals that have antibodies to the epitopes in the chimeric proteins. Hence the chimeric proteins can be used to determine whether or not an individual person or animal has been exposed to and/or infected with Lyme disease spirochetes. Use of the recombinant chimeras in diagnostic assays makes the interpretation of test results easier and more accurate than prior art assays, which required the detection and analysis of antibody responses to several different proteins. Furthermore, it is an improvement over the current state of art in that the production of a single chimeric protein is significantly less expensive than the production of several different proteins.

It is an object of the disclosure to provide a recombinant chimeric polypeptide comprising:

DbpB (SEQ ID NO: 2), or a first variant thereof that is at least 50 amino acids in length, wherein the at least 50 amino acids are identical to at least 50 contiguous amino acids of SEQ ID NO: 2, or a second variant thereof having at least 95% amino acid sequence identity to SEQ ID NO: 2, or a third variant having at least 95% amino acid sequence identity to the first variant;
and
at least one additional *Borreliella* protein, or a first variant thereof that is at least 50 amino acids in length, wherein the at least 50 amino acids are identical to at least 50 contiguous amino acids of the at least one additional *Borreliella* protein, or a second variant thereof having at least 95% amino acid sequence identity to the at least one additional *Borreliella* protein, or a third variant having at least 95% amino acid sequence identity to the first variant.

In some aspects, the at least one additional *Borreliella* protein is:

BBA73 (SEQ ID NO: 3), or a first variant thereof that is at least 50 amino acids in length, wherein the at least 50 amino acids are identical to at least 50 contiguous amino acids of SEQ ID NO: 3, or a second variant thereof having at least 95% amino acid sequence identity to SEQ ID NO: 3, or a third variant having at least 95% amino acid sequence identity to the first variant;

BBK53 (SEQ ID NO: 4), or a first variant thereof that is at least 50 amino acids in length, wherein the at least 50 amino acids are identical to at least 50 contiguous amino acids of SEQ ID NO: 4, or a second variant thereof having at least 95% amino acid sequence identity to SEQ ID NO: 4, or a third variant having at least 95% amino acid sequence identity to the first variant;

BB0238 (SEQ ID NO: 5), or a first variant thereof that is at least 50 amino acids in length, wherein the at least 50 amino acids are identical to at least 50 contiguous amino acids of SEQ ID NO: 5, or a second variant thereof having at least 95% amino acid sequence identity to SEQ ID NO: 5, or a third variant having at least 95% amino acid sequence identity to the first variant;

DbpA (SEQ ID NO: 13), or a first variant thereof that is at least 50 amino acids in length, wherein the at least 50 amino acids are identical to at least 50 contiguous amino acids of SEQ ID NO: 13, or a second variant thereof having at least 95% amino acid sequence identity to SEQ ID NO: 13, or a third variant having at least 95% amino acid sequence identity to the first variant;

BBK19 (SEQ ID NO: 15), or a first variant thereof that is at least 50 amino acids in length, wherein the at least 50 amino acids are identical to at least 50 contiguous amino acids of (SEQ ID NO: 15), or a second variant thereof having at least 95% amino acid sequence identity to SEQ ID NO: 15, or a third variant having at least 95% amino acid sequence identity to the first variant; or VlsE (SEQ ID NO: 16), or a first variant thereof that is at least 50 amino acids in length, wherein the at least 50 amino acids are identical to at least 50 contiguous amino acids of SEQ ID NO: 16, or a second variant thereof having at least 95% amino acid sequence identity to SEQ ID NO: 16, or a third variant having at least 95% amino acid sequence identity to the first variant.

In further aspects, the recombinant chimeric polypeptide comprises
  i) DbpB (SEQ ID NO:2), or a first variant thereof that is at least 50 amino acids in length, wherein the at least 50 amino acids are identical to at least 50 contiguous amino acids of (SEQ ID NO:2), or a second variant thereof having at least 95% amino acid sequence identity to SEQ ID NO:2, or a third variant having at least 95% amino acid sequence identity to the first variant;
  ii) BBK53 (SEQ ID NO:4), or a first variant thereof that is at least 50 amino acids in length, wherein the at least 50 amino acids are identical to at least 50 contiguous amino acids of SEQ ID NO:4, or a second variant thereof having at least 95% amino acid sequence identity to SEQ ID NO:4, or a third variant having at least 95% amino acid sequence identity to the first variant; and
  iii) BBA73 (SEQ ID NO:3), or a first variant thereof that is at least 50 amino acids in length, wherein the at least 50 amino acids are identical to at least 50 contiguous amino acids of SEQ ID NO:3, or a second variant thereof having at least 95% amino acid sequence identity to SEQ ID NO:3, or a third variant having at least 95% amino acid sequence identity to the first variant.

In additional aspects, the recombinant chimeric polypeptide comprises
  i) DbpB (SEQ ID NO:2), or a first variant thereof that is at least 50 amino acids in length, wherein the at least 50 amino acids are identical to at least 50 contiguous amino acids of SEQ ID NO:2, or a second variant thereof having at least 95% amino acid sequence identity to SEQ ID NO:2, or a third variant having at least 95% amino acid sequence identity to the first variant;
  ii) BBK53 (SEQ ID NO:4), or a first variant thereof that is at least 50 amino acids in length, wherein the at least 50 amino acids are identical to at least 50 contiguous amino acids of SEQ ID NO:4, or a second variant thereof having at least 95% amino acid sequence identity to SEQ ID NO:4, or a third variant having at least 95% amino acid sequence identity to the first variant;
  iii) BBA73 (SEQ ID NO:3), or a first variant thereof that is at least 50 amino acids in length, wherein the at least 50 amino acids are identical to at least 50 contiguous amino acids of SEQ ID NO:3, or a second variant thereof having at least 95% amino acid sequence identity to SEQ ID NO:3, or a third variant having at least 95% amino acid sequence identity to the first variant; and
  iv) BB0238 (SEQ ID NO: 5) or a first variant thereof that is at least 50 amino acids in length, wherein the at least 50 amino acids are identical to at least 50 contiguous amino acids of SEQ ID NO:5, or a second variant thereof having at least 95% amino acid sequence identity to SEQ ID NO:5, or a third variant having at least 95% amino acid sequence identity to the first variant.

In some aspects, the recombinant chimeric polypeptide comprises
  i) DbpB (SEQ ID NO:2), or a first variant thereof that is at least 50 amino acids in length, wherein the at least 50 amino acids are identical to at least 50 contiguous amino acids of SEQ ID NO: 2, or a second variant thereof having at least 95% amino acid sequence identity to SEQ ID NO:2, or a third variant having at least 95% amino acid sequence identity to the first variant;
  ii) DbpA (SEQ ID NO:13), or a first variant thereof that is at least 50 amino acids in length, wherein the at least 50 amino acids are identical to at least 50 contiguous amino acids of SEQ ID NO: 13, or a second variant thereof having at least 95% amino acid sequence identity to SEQ ID NO:13, or a third variant having at least 95% amino acid sequence identity to the first variant;
  iii) BBK19 (SEQ ID NO:15), or a first variant thereof that is at least 50 amino acids in length, wherein the at least 50 amino acids are identical to at least 50 contiguous amino acids of SEQ ID NO:15, or a second variant thereof having at least 95% amino acid sequence identity to SEQ ID NO:15, or a third variant having at least 95% amino acid sequence identity to the first variant, and
  iv) VlsE (SEQ ID NO:16), or a first variant thereof that is at least 50 amino acids in length, wherein the at least 50 amino acids are identical to at least 50 contiguous amino acids of SEQ ID NO:16, or a second variant thereof having at least 95% amino acid sequence identity to SEQ ID NO:16, or a third variant having at least 95% amino acid sequence identity to the first variant.

In additional aspects, the recombinant chimeric polypeptide comprises i) DbpB (SEQ ID NO:2), ii) BBK53 (SEQ ID NO:4 and iii) BBA73 (SEQ ID NO:3).

In yet further aspects, the recombinant chimeric polypeptide comprises i) DbpB (SEQ ID NO:2), ii) BBK53 (SEQ ID NO:4), iii) BBA73 (SEQ ID NO:3), and iv) BB0238 (SEQ ID NO: 5).

In other aspects, the recombinant chimeric polypeptide comprises i) DbpB (SEQ ID NO:2), ii) DbpA (SEQ ID NO:13), iii) BBK19 (SEQ ID NO:15), and iv) VlsE (SEQ ID NO:16).

The disclosure also provides composition comprising at least one recombinant chimeric polypeptide and a physiologically acceptable carrier.

The disclosure also provides a lyophilized, reconstitutable preparation comprising at least one recombinant chimeric polypeptide.

The disclosure also provides a nucleic acid encoding a recombinant chimeric polypeptide.

The disclosure also provides a vector comprising the nucleic acid, (i.e., a vector comprising a nucleic acid encoding any of the recombinant polypeptides disclosed herein).

The disclosure also provides a host cell comprising the vector (i.e., a host cell comprising a vector comprising a nucleic acid encoding any of the recombinant polypeptides disclosed herein).

The disclosure also provides an *Escherichia coli* bacterial cell that is genetically engineered to contain and express a nucleic acid (i.e., an *Escherichia coli* bacterial cell that is genetically engineered to contain and express a nucleic acid encoding any of the recombinant polypeptides disclosed herein).

The disclosure also provides method of diagnosing Lyme disease in a subject, comprising i) contacting a biological sample from the mammal with at least one recombinant chimeric polypeptide i.e., at least one of any of the recombinant polypeptides disclosed herein), and detecting antibody-antigen complexes formed by antibodies in the biological sample and the at least one recombinant chimeric polypeptide, wherein the subject is diagnosed as having Lyme disease when the antibody-antigen complexes are detected. In some aspects, the subject is a human or a non-human mammal. In further aspects, the subject is a non-human mammal and the at least one recombinant chimeric polypeptide is or includes the recombinant chimeric polypeptide (i.e., the at least one recombinant chimeric polypeptide is or includes the recombinant chimeric polypeptide comprising i) DbpB (SEQ ID NO:2), ii) BBK53 (SEQ ID NO:4 and iii) BBA73 (SEQ ID NO:3) and/or the recombinant chimeric polypeptide comprises i) DbpB (SEQ ID NO:2), ii) BBK53 (SEQ ID NO:4), iii) BBA73 (SEQ ID NO:3), and iv) BB0238 (SEQ ID NO: 5)). In further aspects, the subject is a human and the at least one recombinant chimeric polypeptide is or includes a recombinant chimeric polypeptide of (i.e., the at least one recombinant chimeric polypeptide is or includes the recombinant chimeric polypeptide comprising i) DbpB (SEQ ID NO:2), ii) DbpA (SEQ ID NO:13), iii) BBK19 (SEQ ID NO:15), and iv) VlsE (SEQ ID NO:16)).

The disclosure also provides a method of detecting antibodies that specifically bind anti-*Borreliella* antibodies in a test sample, comprising contacting the test sample with at least one recombinant chimeric polypeptide of (i.e., a recombinant chimeric polypeptide comprising: DbpB (SEQ ID NO: 2), or a first variant thereof that is at least 50 amino acids in length, wherein the at least 50 amino acids are identical to at least 50 contiguous amino acids of SEQ ID NO: 2, or a second variant thereof having at least 95% amino acid sequence identity to SEQ ID NO: 2, or a third variant having at least 95% amino acid sequence identity to the first variant; and at least one additional *Borreliella* protein, or a first variant thereof that is at least 50 amino acids in length, wherein the at least 50 amino acids are identical to at least 50 contiguous amino acids of the at least one additional *Borreliella* protein, or a second variant thereof having at least 95% amino acid sequence identity to the at least one additional *Borreliella* protein, or a third variant having at least 95% amino acid sequence identity to the first variant), and detecting one or more recombinant chimeric polypeptide-antibody complexes in said test sample, wherein the detection of recombinant chimeric polypeptide-antibody complexes is an indication that antibodies specific for *Borreliella* are present in the test sample. In various aspects, the method is an assay method selected from the group consisting of a lateral flow assay, an immunoblot and an enzyme-linked immunosorbent assay (ELISA).

The disclosure further provides a device for detecting anti-*Borreliella* antibodies in a sample comprising: a) a sample application pad for receiving the sample; and b) a membrane substrate comprising a first test line, the first test line comprising at least one immobilized recombinant chimeric polypeptide (i.e., at least on of any of the recombinant chimeric polypeptides disclosed herein). In some aspects, the device is a lateral flow immunoassay. In further aspects, the membrane substrate further comprises at least one control line. In additional aspects the device further comprises a backing. In yet further aspects, the device further comprises a wicking pad.

BRIEF DESCRIPTION OF THE FIGURES

FIGS. 9A and B. DCFL4 detects antibodies elicited by infection with Lyme disease spirochetes during early-stage infection and throughout the course of infection. A, ELISA results in which the proteins indicated on the X axis were screened with serum collected 21 days (i.e., early) after tick bite from experimentally infected dogs. B, ELISA results in which the proteins indicated were screened with serum from infected dogs over longer periods of time. The results demonstrate that DCFL4 detects antibodies during both early and late-stage infection.

FIG. 10. Demonstration the chimeric recombinant diagnostic antigens do not yield false positive results in dogs vaccinated with commercially available vaccines. Recombinant proteins were spotted onto membranes and then the membranes were screened with sera from vaccinated or control dogs. One set of dot blots was stained with MemCode™ to verify the presence of the chimerics on the membrane. Representative data are shown for the DCF5A, DCF5B, and DCFL4 chimerics. FhbB is a negative control protein derived from *Treponema denticola* that should not react with any serum sample. *B. burgdorferi* OspA is a positive control protein for the detection of antibodies elicited by vaccination (all current vaccines contain OspA). VlsE is a positive control for the detection of antibodies in dogs infected with Lyme disease spirochetes. Trade names for each vaccine are indicated on the left. False positives were not observed in vaccinated dogs with any of the chimeric constructs.

DETAILED DESCRIPTION

Figure 1:
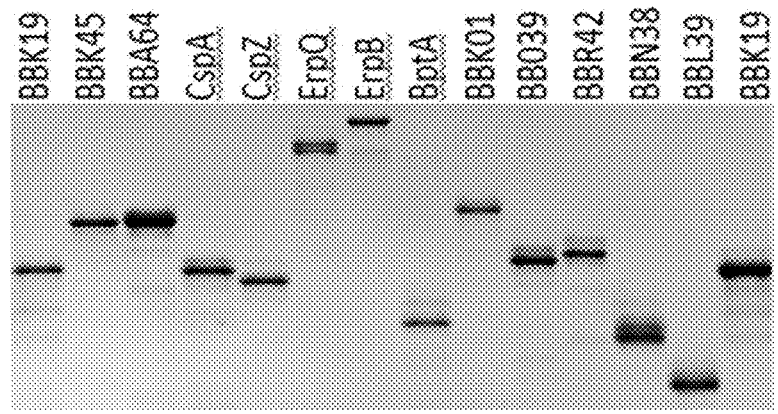
FIG. 1. Synthesis, generation, and purification of candidate antigens for inclusion in chimeric diagnostic proteins. The genes encoding each protein were codon optimized, synthesized, and ligated into the pET45 expression vector. The proteins were expressed and purified. The SDS-PAGE gel presents an image of the purity of representative proteins (indicated along the top).

Aspects of the present disclosure are related to diagnosing disease caused by Lyme disease spirochetes. Described herein is an exhaustive analysis of antibody responses that develop during infection with *Borreliella* species. This was accomplished by generating and individually screening 60 different Lyme disease spirochete proteins to determine if they i) are expressed during mammalian infection and ii) elicit antibody responses during both natural and experimental infection. Sera from humans, dogs, horses, eastern coyotes, foxes (gray and red), pocket gophers, ground hogs, grey squirrels, mice, black vultures, eastern black bears, and raccoons, were screened for antibodies to each of the 60 proteins using single dilution ELISA and immunoblot analyses. While several proteins were identified as being highly antigenic, no single natural protein was able to detect antibodies in all of the infected mammals. Thus, no one single natural protein was identified that would provide the necessary specificity and sensitivity required of a diagnostic assay.

However, a subset of the proteins was detected by most serum samples and were then considered for use in the construction of chimeric proteins, the rationale being that chimerics would allow the detection of antibodies in a wider array of infected mammals. Accordingly, novel "chimeric" recombinant proteins were generated by designing chimeric genes that encode the proteins that had been identified as highly antigenic. The chimeric genes were codon optimized for efficient production in expression systems. The leader peptides or lipidation motifs were omitted to allow for high-level expression. The chimeras, which have no parallel or equivalent in nature, comprise non-lipidated amino acid sequences derived from about 3 to about 8 different proteins selected from the 60 that were initially tested. In some aspects, the amino acid sequences are full-length proteins (minus the N-terminal leader sequence and lipidation motif). In other aspects, the amino acid sequences are antigenic peptide segments (e.g., epitopes) derived from the about 3 to about 8 different proteins. Several different variants of each chimeric protein were made in which the ordering of the component proteins or epitopes was varied. These analyses were critical as the optimal ordering of the polypeptides in the chimerics could not be predicted and was not obvious. In some aspects, the chimeric proteins were modified e.g. by the inclusion of non-native tryptophan insertions to allow for accurate quantification. In other aspects, some properties of some proteins or the genes that encode them were modified to make them amenable to mass production, e.g., by identifying variants of the chimeras that could be readily produced at high levels with high purity as soluble proteins in *Escherichia coli* expression systems.

The specificity and sensitivity of the chimeras were tested using ELISA, dot blots, immunoblot and lateral flow assays. The results showed that, in contrast to any of the individual proteins and other prior art Lyme disease diagnostic proteins, the chimeric proteins disclosed herein advantageously exhibited very high specificity and sensitivity toward antibodies elicited during infection with the Lyme disease spirochetes. Significantly, very high specificity and sensitivity was exhibited in both humans and animals infected with Lyme disease spirochetes. In particular, recombinant chimeric polypeptides comprising the Lyme disease spirochete proteins DbpB, DbpA, BBK19, BBK53, VlsE, BBA73 and BB0238, typically in a specific order within the chimera, exhibited exceptionally high specificity and sensitivity. Also of high significance, the high specificity and sensitivity was exhibited without generating false positive results. In addition, chimeric proteins comprising these proteins are readily produced using in vitro manufacturing processes, such as by using E. coli bacteria that are genetically engineered to encode and express nucleic acids encoding the chimeras.

As described in detail elsewhere herein, the extensive screening from diverse mammals, including numerous species of wildlife, dogs, horses and humans, demonstrated that the chimeras can be used in any species of mammal to determine if a mammal is actively infected or was recently infected with Lyme disease spirochetes. In addition, the chimeras can be used in young dogs with suspected Lyme disease to differentiate between antibodies resulting from an active infection and antibodies resulting from infection of the mother (maternal antibodies). This is done by testing the serum samples obtained from young dogs at timed intervals, shortly after birth (e.g., 6-15 weeks). Antibodies that are maternal in origin decrease in titer over time whereas persistent and elevated antibody responses indicate an active infection.

In order to facilitate the understanding of the present invention, the following definitions are provided:

Antigen: term used historically to designate an entity that is bound by an antibody, and also to designate the entity that induces the production of the antibody. More current usage limits the meaning of antigen to that entity bound by an antibody, while the word "immunogen" is used for the entity that induces antibody production. Where an entity discussed herein is both immunogenic and antigenic, reference to it as either an immunogen or antigen will typically be made according to its intended utility. The terms "antigen", "antigenic region" "immunogen" and "epitope" may be used interchangeably herein. As used herein, an antigen, immunogen or epitope is generally a portion of a protein (e.g. a peptide or polypeptide).

Linker sequences: short peptide sequences encoding functional units that may be engineered or otherwise added at the ends or within recombinant proteins, polypeptides, peptides of interest. Linker sequences may be used as "handles" for protein purification, as detectable signals of expression or binding to other proteins or macromolecules, to modulate tertiary structure, or enhance antigenicity. Examples of linker sequences include but are not limited to an amino acid spacer, an amino acid linker, a signal sequence, a stop transfer sequence, a transmembrane domain, and a protein purification ligand.

Tags: Recombinant protein sequences that can be added to the N- or C-terminus of a recombinant protein for the purpose of identification or for purifying the recombinant protein for subsequent uses. Examples of recombinant protein tags that may be useful in practicing the invention include but are not limited to glutathione-S-transferease (GST), poly-histidine, maltose binding protein (MBP), FLAG, V5, halo, myc, hemaglutinin (HA), S-tag, calmodulin, tag, streptavidin binding protein (SBP), Softag1™, Softag3™, Xpress tag, isopeptag, Spy Tag, biotin carboxyl carrier protein (BCCP), GFP, Nus-tag, strep-tag, thioredoxin tag, TC tag, and Ty tag. All such tags are well-known to those of ordinary skill in the art of recombinant protein production and may or may not be removed before use, using tag specific cleavage protocols. For example, a hexahistidine tag (His-His-His-His-His-His (SEQ ID NO: 74)) is typically removed by incubation of the protein with the enzyme enterokinase which recognizes the following amino acid sequence: AspAspAspAspLys (SEQ ID NO: 75). Cleavage of this motif releases the His tag from the recombinant protein.

Epitope: a specific chemical domain on an antigen that is recognized by a B-cell receptor, and which can be bound by secreted antibody. The term as used herein is interchangeable with "antigenic determinant". An epitope may comprise a single, non-interrupted, contiguous chain of amino acids joined together by peptide bonds to form a peptide or polypeptide. Such an epitope can be described by its primary structure, i.e. the linear sequence of amino acids in the peptide chain. Epitope may also refer to conformational epitopes, which are comprised of at least some amino acids that are not part of an uninterrupted, linear sequence of amino acids, but which are brought into proximity to other residues in the epitope by secondary, tertiary and/or quaternary interactions of the protein. Residues in conformational epitopes may be located far from other resides in the epitope with respect to primary sequence but may be spatially located near other residues in the conformational epitope due to protein folding.

Panel indicates more than one protein e.g., in an assay.

Protein: Generally means a linear sequence of about 100 or more amino acids covalently joined by peptide bonds.

Polypeptide: Generally means a linear sequence of about 55 to about 100 amino acids covalently joined by peptide bonds.

Peptide: Generally means a linear sequence of about 100 or fewer amino acids covalently joined by peptide bonds.

Note: The terms "polypeptide" and "protein" may be used interchangeably herein.

Chimeric or fusion peptide or polypeptide: a recombinant or synthetic peptide or polypeptide whose primary sequence comprises two or more linear amino acid sequences which do not occur together in a single molecule in nature. The two or more sequences may be, for example, a peptide (e.g. an epitope or antigenic region) and a linker sequence, or two or more peptides (which may be the same or different) which are either contiguous or separated by a linker sequences, etc.

Original or native or wild type sequence: The sequence of a peptide, polypeptide, protein or nucleic acid as found in nature.

Recombinant peptide, polypeptide, protein or nucleic acid: A peptide, polypeptide, protein or nucleic acid that has been produced and/or manipulated using molecular biology techniques such as cloning, polymerase chain reaction (PCR), etc.

Synthetic peptide, polypeptide, protein or nucleic acid: A peptide, polypeptide, protein or nucleic acid that has been produced using chemical synthesis procedures.

Techniques for recombinant (i.e., engineered) DNA, peptide and oligonucleotide synthesis, immunoassays, tissue culture, transformation (e.g., electroporation, lipofection), enzymatic reactions, purification, and related techniques and procedures may be generally performed as described in various general and more specific references in microbiology, molecular biology, biochemistry, molecular genetics, cell biology, virology and immunology as cited and discussed throughout the present specification. See, e.g., Sambrook et al., Molecular Cloning: A Laboratory Manual, 3d ed., Cold Spring Harbor Laboratory Press, Cold Spring Harbor, N.Y.; Current Protocols in Molecular Biology (John Wiley and Sons, updated July 2008); Short Protocols in Molecular Biology: A Compendium of Methods from Current Protocols in Molecular Biology, Greene Pub. Associates and Wiley-Interscience; Glover, DNA Cloning: A Practical Approach, vol. I & II (IRL Press, Oxford Univ. Press USA, 1985); Current Protocols in Immunology (Edited by: John E. Coligan, Ada M. Kruisbeek, David H. Margulies, Ethan M. Shevach, Warren Strober 2001 John Wiley & Sons, NY, NY); Real-Time PCR: Current Technology and Applications, Edited by Julie Logan, Kirstin Edwards and Nick Saunders, 2009, Caister Academic Press, Norfolk, UK; Anand, Techniques for the Analysis of Complex Genomes, (Academic Press, New York, 1992); Guthrie and Fink, Guide to Yeast Genetics and Molecular Biology (Academic Press, New York, 1991); Oligonucleotide Synthesis (N. Gait, Ed., 1984); Nucleic Acid The Hybridization (B. Hames & S. Higgins, Eds., 1985); Transcription and Translation (B. Hames & S. Higgins, Eds., 1984); Animal Cell Culture (R. Freshney, Ed., 1986); Perbal, A Practical Guide to Molecular Cloning (1984); Next-Generation Genome Sequencing (Janitz, 2008 Wiley-VCH); PCR Protocols (Methods in Molecular Biology) (Park, Ed., 3rd Edition, 2010 Humana Press); Immobilized Cells And Enzymes (IRL Press, 1986); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Harlow and Lane, Antibodies, (Cold Spring Harbor Laboratory Press, Cold Spring Harbor, N.Y., 1998); Immunochemical Methods In Cell And Molecular Biology (Mayer and Walker, eds., Academic Press, London, 1987); Handbook Of Experimental Immunology, Volumes I-IV (D. M. Weir and C C Blackwell, eds., 1986); Roitt, Essential Immunology, 6th Edition, (Blackwell Scientific Publications, Oxford, 1988); Current Protocols in Immunology (Q. E. Coligan, A. M. Kruisbeek, D. H. Margulies, E. M. Shevach and W. Strober, eds., 1991); Annual Review of Immunology; as well as monographs in journals such as Advances in Immunology. *Identity, similarity and structural similarity*. As used herein, a polypeptide (e.g. a first polypeptide) is "similar" to a reference polypeptide (e.g. a second polypeptide) if the amino acid sequence of the first polypeptide possesses a specified amount of identity compared to the second reference polypeptide. Similarity of two polypeptides can be determined along the entire length of the polypeptides by aligning the residues of the two polypeptides to optimize the number of identical amino acids along the lengths of their sequences; gaps in either or both sequences are permitted in making the alignment in order to optimize the number of identical amino acids, although the amino acids in each sequence must nonetheless remain in their proper order.

A pair-wise comparison analysis of amino acid sequences can be carried out using the BESTFIT algorithm in the GCG package (version 10.2, Madison Wis.). Alternatively, polypeptides may be compared using the Blastp program of the BLAST 2 search algorithm, as described by Tatiana et al., (FEMS Microbiol Lett, 174, 247-250 (1999)), and available on the National Center for Biotechnology Information (NCBI) website. The default values for all BLAST 2 search parameters may be used, including matrix=BLOSUM62; open gap penalty=11, extension gap penalty=1, gap x_dropoff=50, expect=10, word size=3, and filter on.

In the comparison of two amino acid sequences, similarity may be referred to by e.g. "percent identity" or "percent similarity." "Identity" refers to the presence of identical amino acids along the entire length of the polypeptides that are being compared. "Similarity" generally refers to the presence of not only identical amino acids but also the presence of conservative substitutions along the entire length of the polypeptides that are being compared. A conservative substitution for an amino acid may be selected from other members of the class to which the amino acid belongs. For example, it is well-known in the art of protein biochemistry that an amino acid belonging to a grouping of amino acids having a particular size or characteristic (such as charge, hydrophobicity and hydrophilicity) can be substituted for another amino acid without altering the activity of a protein, particularly in regions of the protein that are not directly associated with biological activity. For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Conservative substitutions include, for example, Lys for Arg and vice versa to maintain a positive charge; Glu for Asp and vice versa to maintain a negative charge; Ser for Thr so that a free —OH is maintained; and Gln for Asn to maintain a free —$NH_2$. Likewise, biologically active analogs of a polypeptide containing deletions or additions of one or more contiguous or noncontiguous amino acids that do not eliminate a functional activity of the polypeptide are also encompassed.

"Specificity" as used herein generally refers to the ability of a chimeric protein to discriminate between similar or even dissimilar antibodies, e.g., antibodies to other infectious agents. Specificity measures how often a test correctly gives a negative result when a person does not have the disease. Low specificity can result in false positives, incorrectly identifying non-infected subjects as sick. The higher the specificity, the less chance there will be a false positive result.

"Sensitivity" as used herein generally refers to how often a test correctly gives a positive result when a subject has or has had an infection that generated antibodies to an infectious agent. Low sensitivity can result in false negatives, incorrectly identifying infected subjects as not infected. The higher the sensitivity, the less chance there will be a false negative result.

The Recombinant Chimeric Polypeptides

In one embodiment, the compositions of the invention comprise one or more isolated and purified recombinant chimeric proteins/polypeptides. Each chimeric polypeptide comprises a plurality of Lyme disease spirochete proteins. In some aspects, each chimeric polypeptide comprises, for example, from about 2-10 different *Borreliella* proteins, such as about 2, 3, 4, 5, 6, 7, 8, 9 or 10 or more different *Borreliella* proteins, and/or peptide segments from about 2, 3, 4, 5, 6, 7, 8, 9 or 10 or more different *Borreliella* proteins. In some aspects, each chimeric polypeptide comprises from about 3 to 6 different *Borreliella* proteins (e.g. 3, 4, 5, or 6), and/or peptide segments from about 3 to 6 different *Borreliella* proteins (i.e. full length proteins and peptide segments may both be present in a single chimera). In some aspects, *Borreliella* proteins, and/or peptide segments thereof, that are included in a chimera are selected from, for example: BB0141, BB0147, BB0167, BB0238, BB0283, BB0419, BB0564, BB0603, BB0612, BB0664, BB0733, BBA04, BBA15, BBA16, BBA19, BBA24, BBA25, BBA36, BBA57, BBA60, BBA64, BBA66, BBA68, BBA73, BBA74, BBB07, BBB09, BBB14, BBB19, BBC10, BBE09, BBE16, BBH06, BBI29, BBI36, BBI39, BBJ41, BBK01, BBK19, BBK32, BBK45, BBK48, BBK50, BBK52, BBK53, BBL39, BBM27, BBM28, BBM38, BBN38, BBN39, BBO39, BBO40, BBP39, BBQ47, BBR28, BBR42, BBS30 and BBS41. In this list, open reading frames (ORFs) are in all caps and the commonly used protein names follow in parentheses. It is noted that the gene names are those that were originally assigned for the *B. burgdorferi* isolate B31.

The full-length, wild-type sequences of *Borreliella* proteins that may be present in the chimeras are as follows:

```
BBA25 (DbpD):
                                          (SEQ ID NO:2)
ALESSSKDLKNKILKIKKEATGKGVLFEAFTGLKTGSKVTSGGLALREAKVQAIV
ETGKFLKIIEEEALKLKETGNSGQFLAMFDLMLEVVESLEDVGIIGLKARVLEESK
NNPINTAERLLAAKAQIENQLKVVKEKQNIENGGEKKNNKSKKKK

BBA73:
                                          (SEQ ID NO:3)
NTEAISELQSSPIKLGKIKVLQKTEKIVSTQNLQNLQQSQFFKNEKEKIIKKIAQEF
DENEKLINKIGPNIEMFAQTINTDIQKIEPNDQFGINKTLFTEKKDNNIDFMLKDNR
LRRLFYSSLNYDENKIKKLATILAQTSSSNDYHYTLIGLIFWTGFKIQEAFESAVNI
LTKDEQKRLIFNFRTKTVKEIQENFEKLMQERNSWIKIVDNIIGEYDKNTGGCKA
DGKILGEVIRVGYEHELDSNKSMQILNNIETPLKTCCDHIHY

BBK53:
                                          (SEQ ID NO:4)
QTFFENSESSDMGSDEIVTEGIFSSLKLYASEHRLLVEIKKTLISLKDPNYRDVVRP
VSDYNEEYFNKFFLDLGSEQSKDLIKLFIMVKNEQNNNKFMRIVRWLYSCIEELY
SLDIKYSGEGSHEYNRNMPRPTAYEQYLKVKRYDYNSPVSILPT

BB0238:
                                          (SEQ ID NO:5)
DKQKELAIFYYEVGQRYINVGKIKKGKLFQAKALKIYPDLKKGFDIKLAVKELD
ARIKDDNPKVVMLEDIKLEEIPGIVHEKIEINDFTNAPKIEYIAQRERSKNQDKIIKF
QFGKFARALISRNFDLFDSVIADKVNVMGQFESKNDFISTLSSASSKADADELEY
LSVDDYYDLKSLKISKSNDTSFAVNVNAKKNDVTKNFPFWKERQTLIFTTEDDN
NWFLSSIN

BBA24 (DbpA) with leader sequence underlined:
                                          (SEQ ID NO:12)
MIKCNNKTFNNLLKLTILVNLLISCGLTGATKIRLERSAKDITDEIDAIKKDAALK
GVNFDAFKDKKTGSGVSENPFILEAKVRATTVAEKFVIAIEEEATKLKETGSSGEF
SAMYDLMFEVSKPLQKLGIQEMTKTVSDAAEENPPTTAQGVLEIAKKMREKLQR
VHTKNYCTLKKKENSTFTDEKCKNN BBA24 (DbpA) without the leader sequence:
                                          (SEQ ID NO:13)
TKIRLERSAKDITDEIDAIKKDAALKGVNFDAFKDKKTGSGVSENPFILEAKVRAT
TVAEKFVIAIEEEATKLKETGSSGEFSAMYDLMFEVSKPLQKLGIQEMTKTVSDA
AEENPPTTAQGVLEIAKKMREKLQRVHTKNYCTLKKKENSTFTDEKCKNN BBK19 with leader sequence:
                                          (SEQ ID NO:14)
MKKYIINLSLCLLLLSCNLFSKDSRSRQKYNFKVPAKSVSNPINKENIDTEKGTNT
TLCIKEKDSRIIIKDCINNQELFKVKSKRRYDFKKAMLLGIQTALKVINIGNNNKK
LTSIKKHNDHILLEFKDNKIYIIRLSELKKHLLKSKKKPLLGSPIPGGGDAEFVDDP
DGRIEAELEAEQEQEMLDREDFGDEEDEELEEEIFGKEKPNN BBK19 without leader sequence:
                                          (SEQ ID NO:15)
NLFSKDSRSRQKYNFKVPAKSVSNPINKENIDTEKGTNTTLCIKEKDSRIIIKDCIN
NQELFKVKSKRRYDFKKAMLLGIQTALKVINIGNNNKKLTSIKKHNDHILLEFKD
NKIYIIRLSELKKHLLKSKKKPLLGSPIPGGGDAEFVDDPDGRIEAELEAEQEQEM
LDREDFGDEEDEELEEEIFGKEKPNND VlsE without leader sequence:
                                          (SEQ ID NO:16)
DKDDPTNKFYQSVIQLGNGFLDVFTSFGGLVAEAFGFKSDPKKSDVKTYFTTVA
AKLEKTKTDLNSLPKEKSDISSTTGKPDSTGSVGTAVEGAIKEVSELLDKLVKAV
KTAEGASSGTAAIGEVVADADAAKVADKASVKGIAKGIKEIVEAAGGSEKLKAV
AAAKGENNKGAGKLFGKAGAAAHGDSEAASKAAGAVSAVSGEQILSAIVTAAD
AAEQDGKKPEEAKNPIAAAIGDKDGGAEFGQDEMKKDDQIAAAIALRGMAKDG
KFAVKDGEKEKAEGAIKGAAESAVRKVLGAITGLIGDAVSSGLRKVGDSVKAAS
KETPPALNK BB0141: leader sequence is underlined
                                          (SEQ ID NO:17)
MNLIFNINLYLKKYFLVLFLVLVACVGDNKLDDKNIDKEKESSYRFPVIAMKVK
KGILSDYLSLNGDVDTKVKADIFPDAVGKITSLRIKLGAYVQKGQIVATLDPSRP
GSVYLKSPVRAPISGYILNITKKIGETVNPQSNIAVVGRIDTKQILTYVSEKYISNIK
VGNDAIIEVGAYSNEKFKAKVSEISPILDSKSRTIEVYLTPIGSNLDKLIIGMFSKIK
LITKRFKDVIKISREAVVEREGKKFVFKVDLESKSVQMLPITVLFEIDNIVALSGEV
EENDLIVVEGMSALSNGSLINLVDTKEGLSAESNI
```

BB0147:
(SEQ ID NO:18)
MIINHNTSAINASRNNGINAANLSKTQEKLSSGYRINRASDDAAGMGVSGKINAQ
IRGLSQASRNTSKAINFIQTTEGNLNEVEKVLVRMKELAVQGSNGTYSDADRGSI
QIEIEQLTDEINRIADQAQYNQMHMLSNKSASQNVRTAEELGMQPAKINTPASLS
GSQASWTLRVHVGANQDEAIAVNIYAANVANLFSGEGAQTAQAAPVQEGVQQE
GAQQPAPATAPSQGGVNSPVNVTTTVDANTSLAKIENAIRMISDQRANLGAFQN
RLESIKNSTEYAIENLKASYAQIKDATMTDEVVAATTNSILTQSAMAMIAQANQV
PQYVLSLLR

BB0167:
(SEQ ID NO:19)
MNTKATTPLLLLFLIQSLAFSSEIFEFKYIKGSKFRLEGTDNQKIYFNGHYNSSSNT
NIQISSEIKDIKENFASIKAFFRILKRENINEPYLLNEEFEEIFSVNKQGEYTIGANQK
RPSVRGIPRFPKTPIKINEKWSYLAEEYIEASKIDKSIKDFVVKFNVNYEYKGKEE
HNGKHYHIILSNYESQYNVKNISFYQKVDQKIYFDNEIGNTYKYSDKYIFEINQNN
NQHFKMIGNSLGRIVSIELPNDNLIETEVENYIREKKIKAIEVEKNNKGINLSFDIEF
YPNSFQILQKEYKKIDLIAKLLEKFKKNNILIEGHTEQFGLEEEMHELSEKRARAIG
NYLIKMKVKDKDQILFKGWGSQKPKYPKSSPLKAKNRRVEITILNN

BB0283:
(SEQ ID NO:20)
MMRSLYSGVSGLQNHQTRMDVVGNNIANVNTIGFKKGRVNFQDMISQSISGASR
PTDARGGTNPKQVGLGMNVASIDTIHTQGAFQSTQKASDLGVSGNGFFILKEGK
NLFYTRAGAFDVDSDRHLVNPANGMRIQGWMARDLEGEKVINTASDIEDLIIPIG
DKEGAKSTKNVTFACNLDKRLPLIQEGANPADIARGTWVVNKSLYDSFGNVSVL
ELRVVKDLNTPNLWNATVLINGEQNSNFTLGFDNEGALASLNGQPGQKGDILQIP
ITFNVLGANVGEVGEQQTVNLKLGTVGSYTDSITQFADSSSTKAIIQDGYGMGY
MENYEIDQNGVIVGIYSNGIRRDLGKIALASFMNPGGLAKSGDTNFVETSNSGQV
RIGETGLAGLGDIRSGVLEMANVDLAEQFTDMIVTQRGFQANAKTITTSDQLLQE
LVRLKN

BB0564:
(SEQ ID NO:21)
MQSKNKLIRLLIIITLFFNVENIFTNEKSKNNITGQNSTTDPKIESLKAKTKIKFGFI
LPYPTAIEFSINNFDIGVGVTILSVSEFFPKSPIALLFKIYCDYIFLNLKFKDSNFIFFL
GSSLFFEIGKITSSDLTNVSSGITYKIGVGLPLGIIYEAYYDIIEIIIKTTPSIFIGQMPN
GNLIFPIKGNFSIGIKGSLKI

BB0603:
(SEQ ID NO:22)
MKSHILYKLIIFLTTSAAIFAADALKEKDIFKINPWMPTFGFENTSEFRLDMDELVP
GFENKSKITIKLKPFEANPELGKDDPFSAYIKVEDLALKAEGKKGDQFKIDVGDIT
AQINMYDFFIKISTMTDFDFNKESLFSFAPMTGFKSTYYGFPSNDRAVRGTILARG
WKPIKNLLDQNEDTKSVIAETPFELNFGLSGAYGNETFNNSSITYSLKDKSVVGN
DLLSPTLSNSAILASFGAKYKLGLTKINDKNTYLILQMGTDFGIDPFASDFSIFGHI
SKAANFKKETPSDPNKKAEIFDPNGNALNFSKNTELGIAFSTGASIGFAWNKDTG
EKESWAIKGSDSYSTRLFGEQDKKSGVALGISYGQNLYRSKDTEKRLKTISENAF
QSLNVEISSYEDNKKGIINGLGWITSIGLYDILRQKSVENYPTTISSTTENNQTEQSS
TSTKTTTPNLTFEDAMKLGLALYLDYAIPIASISTEAYVVPYIGA YILGPSNKLSSD
ATKIYLKTGLSLEKLIRFTTISLGWDSNNIIELANKNTNNAAIGSAFLQFKIAYSGS

BB0612: leader sequence is underlined
(SEQ ID NO:23)
<u>MARVKGQKVKECSFCGLSVAELGGNVVISNGVAICPECSKICHNLFKEKLCKPL</u>
DSKSNGLPTPKQLKDHLDMYVVGQEDAKKVLSVAVYNHYKRILKNNKYDNGIE
IEKSNILLVGPTGSGKTLLAKTLAAEMNVPFAIADATTLTEAGYVGEDVENILLKL
IHAAHGDVSLAEKGIIYIDEIDKIAKKNENVSITRDVSGEGVQQALLKIIEGTVANV
PPRGGRKHPYEDTIEINTQNILFICGGAFVGLENIVKNRINKSSIGFSAIEKKNIRED
TSLKYLEMEDLIKFGLIPEFVGRLPVHSYLEKLNKEDLLRILVDPQNSIVKQYYHM
FKMDNVELVFEKDALESIVDEAILKNTGARGLRSILEGLLKDVMFEVPSISKAKK
VVVTKESVLNADVNPLILVGNAIKKPWAKELYEINLKYDKK BB0664: the leader sequence is underlined
(SEQ ID NO:24)
<u>MLIARIMNINTLFYGMIIIIFALISCNHKNIQYDKRIKKFLDKNKIEYKIDSENDFIAF</u>
KDINNNEKEEVIIRSRLNSYKNSKIREIFGIVKVFDINTPKIKEISDSLMSDSYNNRV
FGSWEIIHNAERGINSLVYIVKAEEFANDTFLLDAIDEIASTISIFKKIITTNNENIDN
NEENNNTNESNEQPTLKQEKTNSTKESNNELKEDQIEEELQEIKAQ BB0733:
(SEQ ID NO:25)
MLLSRKIRDYGAKYRGKEIKMSTEINSFLNLRNTIEMRIGSYTAFGVIYSISMDSL
KLIFQEDTVLPALAKNKNLGSIQLKKNSDSKSSAAFPPFLSVKLLSASAYSSLNKE
YNLLTLEFLSPAPEEIAIKVGKLLDLKLGQNQRIHERIIIDKDSIRKLKIDSDKAFIK
FNGAKHKCLIKDLSYGGALVISSFDYGDVEEDAIDLIFSFEFIDGEIFIEGKSKSLSV
IQTPSGKVFALGIAFDEDKIPLEYTMLIHDYFN -continued BBA04: the leader sequence is underlined (SEQ ID NO:26)

<u>MKRVIVSFVVLILGCNLDDNSKMERKGSNKLIRESGSDRRGQENRALGAMNFGL
FSGDSGVVYDLQNYETLKALENKNKFIDYSKIEFLEGTKSINAFIWAVSVRWIKIK</u>
ARDLFGECGDFIKELKGIKYSYLVSPVDGSYISYAMPIIVFETTRESDPLYSVSGFK
LISKGNDINFNENKSGFWGRLPMSEKSVESGLVTAYPFGSSDAKKVIEAFASLYN
NGTWSDMIAEITIKSKQYPKNEKVYRITLDSQLFNVAMKKIIEKYPKIKSASFAFN
SLIN

BBA15: the leader sequence is underlined (SEQ ID NO:27)

<u>MKKYLLGIGLILALIACKQNVSSLDEKNSVSVDLPGEMKVLVSKEKNKDGKYDL</u>
IATVDKLELKGTSDKNNGSGVLEGVKADKSKVKLTISDDLGQTTLEVFKEDGKT
LVSKKVTSKDKSSTEEKFNEKGEVSEKIITRADGTRLEYTGIKSDGSGKAKEVLK
GYVLEGTLTAEKTTLVVKEGTVTLSKNISKSGEVSVELNDTDSSAATKKTAAWN
SGTSTLTITVNSKKTKDLVFTKENTITVQQYDSNGTKLEGSAVEITKLDEIKNALK

BBA16: the leader sequence is underlined (SEQ ID NO:28)

<u>MRLLIGFALALALIGCAQKGAESIGSQKENDLNLEDSSKKSHQNAKQDLPAVTED
SVSLFNGNKIFVSKEKNSSGKYDLRATIDQVELKGTSDKNNGSGTLEGSKPDKSK</u>
VKLTVSADLNTVTLEAFDASNQKISSKVTKKQGSITEETLKANKLDSKKLTRSNG
TTLEYSQITDADNATKAVETLKNSIKLEGSLVGGKTTVEIKEGTVTLKREIEKDGK
VKVFLNDTAGSNKKTGKWEDSTSTLTISADSKKTKDLVFLTDGTITVQQYNTAG
TSLEGSASEIKNLSELKNALK

BBA19:

(SEQ ID NO:29)

MTALLERLKQKQKELKLDADNKPKAKKGKKATVFSKIEEVKGRKIYHTKIFNDF
YTFGISKNEPTKFFISLRGIFNIEDISMFHLFSVREDDEFMGIYYGIRKLDKAFIVKN
FNKKETYTLRKCEYIEFRFKKGSVFCYLNGLHILLKKDRVNSPYYNTLLNIILELE
TELYAFYSKKLSKGGIIPEWIKKRQK

BBA36: the leader sequence is underlined (SEQ ID NO:30)

<u>MQRISILLMLLAVFSCKQFGDVKSLTEIDSGNGIPLVVSDVVKDLIPKEISLTPEEA</u>
EKLESLKVFLKDAMSVNGREEALKAEYEKSYKEFFDWLSKDVNRQKEFISSFDNI
SSIVSKAVDASKKRRPTEQQSLGFKEYVCYKIKNSKGEALSLFFQKVVDAFGADP
YKKDNDESVQKPVKCNEEIFKVIKKVLTESESNNELKNLKNYGNV

BBA57: the leader sequence is underlined (SEQ ID NO:31)

<u>MNGKLRKALKIAIFTTLLLVISCNANMDTNDKNKALNEYKLKNISEVIKNSLQLE</u>
SDPKLKKEPESNINQSTPPILEIEKIEPGKQEMSLKSEFGSESLMPLEEPEEANMAK
SEEEIAKIQEKLLLIGASDEITDQELGENMQKFLNPTTVEFKISTTTNETILTTIEEEE
INNNKDKIFDHKEENVTLGNNSLENATLNKNTITLAQNQKYTTHLKNDDKFITKE
YLKQVRDSLDKALNAIKNLETSKEFRELENLPKDQENSPSAKKESTESNINNTNT
ENIEIIKNRLLEELNKSELIFEDTKDPLGTSTIKKVIDAAKKWQEKENSSQIDWDLG
FKFHPNPKFYNKLTAQEYKVLAEKFTKVKNEYKNTKEQLKAESKLTTNSISKIIN
ATKEFANQVINLILLVEKNYQ

BBA60: the leader sequence is underlined (SEQ ID NO:32)

<u>MSKKVILILLEILILSCDLSINKEQKTKEKTSEKQESEKQNIEKQEPEKQKQNAAKII</u>
PTVSIQTVEIRESNQIPKSIEKYYKQAYPIQTFTLDFSITREKEFLKPEDKILPTQGK
VESLSILINKKLLDFKAPENPKSSTLKNFKEIKNIENFFQNQDLLFVLTLKDKNNN
NTINIMLNPPNDIQKPKDYILKDLKDTIKKGTGEKYLNPIYRFQIKNKKDYHSIDY
NKVTISEKTIELDLLPHEQVFQMNKNFTKILDTITDLNNLKLVIQKELV

BBA64: the leader sequence is underlined (SEQ ID NO:33)

<u>MKNNKLIAIFLLHVLTVLILISCSLEVKDSNESKKHKKEKRKGKVENLLVAINNL</u>
KNPTKPAAGKNKANSKASKQKNNPNANANNAPKKILDPEVAKLIQKILDRSENII
QISEMDSSRGEPNDQFGMRAEIFSKIFFNANSTVHFDSHEYTEERRMLYTSLNFNE
GKIFNLGQILSKLSQDSNYRGLVKETLINRGFSIQLAMEEISAKILNVKDKLQQLN
KPNLETLYNDFEKLTSLKEKWLKDTDDLIDEYNTNPDLQTDVSKLNDTLRSKNS
RAQFANIHDIILDLVNTTTNILAPIQ

BBA66: the leader sequence is underlined (SEQ ID NO:34)

<u>MKIKPLIQLKLLGLFLFSC</u>TIDANLNEDYKNKVKGILNKAADDQETTSADTNSNA
AKNIPIADNDKVAAELKKQSQAAKTVAAAPNKGSQNQPQTTPNKGSQNQQAAP
SPQLQSLSFSADLSNLPKTTAARAASLTKQRIPIQAVTTVPGNTRTFNSRNSGLPTF
ALNYSFSQPTRQQTNSSSAVQTTTSSGSKLQTLKNELIRAISEEKNKTQNNFGFRE
TYDQFKMKDSAFELLDVISSAKVYDRSYAPQLNSNTPEAENERNKFYALMDFDQ
YKIEQFGSIMEALYNENQNHSLIRELMISGLGTQISFELALEEINKKIEIFNQDYLN
AKINSFDFTMKLKELKSKLNQILDKRKEWSRQADGLIANASSNSSLSDSKSLAEYI
KKRYLDNMQNARQSVLEAYISIM

-continued

BBA68: the leader sequence is underlined
(SEQ ID NO:35)
MKKAKLNIIKINIIAMILTLICTSCAPFSKIDPKANANTKPKKITNPGENTQNFEDKS
GDLSTSDEKIMETIASELKAIGKELEDQKKEENIQIAKIAKEKFDFLSTFKVGPYDL
IDEDIQMKIKRTLYSSLDYKKENIEKLKEILEILKKNSEHYNIIGRLIYHISWGIQFQI
EQNLELIQNGVENLSQEESKSLLMQIKSNLEIKQRLKKTLNETLKVYNQNTQDNE
KILAEHFNKYYKDFDTLKPAFY BBA74:
(SEQ ID NO:36)
MTKIFSNLIINGLLFGFVSLNVFADSNNANILKPQSNVLEHSDQKDNKKLDQKDQ
VNQALDTINKVTEDVSSKLEGVRESSLELVESNDAGVVKKFVGSMSLMSDVAK
GTVVASQEATIVAKCSGMVAEGANKVVEMSKKAVQETQKAVSVAGEATFLIEK
QIMLNKSPNNKELELTKEEFAKVEQVKETLMASERALDETVQEAQKVLNMVNG
LNPSNKDQVLAKKDVAKAISNVVKVAQGARDLTKVMAISLYMR BBB07:
(SEQ ID NO:37)
MKEIGISIYPNVSPKNKIIKYLEKSAHFGFTQVFTSLLYINGNEFDIFKELLSIANKN
GMKPIIDVSPEIFKELGIDLSNLRNCPKLDYFKKLGAWAIRLDNTFTGIEESLMTFN
DSDLKIQLNISNINKHIDTIMYFKPNIKNLLGCHNFYPHKYTGLSRNFFKETTKIFK
HYSIPTAAFISSNNAEECARGKEKEGVPTLESHRSKDIETQAKDLFKEGIDTVLISN
CFPSETELKKVSKVNRNILELKADLNPDANSVEKEIILENLHFNRGDINSYRIRST
MPRVYYNNKKFPVHSPNEIKKGDILIDSSEYLGYTGELQIALKDTPNNGLVNVVG
KIINDEIYLLEKIEPWEKFKIIENK BBB09: the leader sequence is underlined
(SEQ ID NO:38)
MKYLKNISLFLLILGCKSIPNGNFNLHDTNHKLGKLKFQEDSIISRNYDNKISIVGV
YNPLTEKENFKVNIFIKKKGLQIDPENILINEEKINYSKYKAELKVKSSFNKSIISISL
TNSRDLLTYIYDKSTGKYINIDFKDNWNVSHSIKFNKEYILAYITDFDKEIKISKNI
LQKRIDNRKIEIEKTELKTEYNEIEDYYIYSMKIPKLFEKSDAPSETYETFVIANYY
PCENLNILFLNLSLYSDKLRFLNSIYDENDRKLKMEPPVRALKNSKTIKETLNIVL
SPQKIIELAKNIEKDITLKLKSYGEKGEFTFEIYKPLLLKFLKEVDHCIKNLQSSRH
KF BBB14: the leader sequence is underlined
(SEQ ID NO:39)
MILYQNQLKFLKLLVFFLLISCTSLNVEHDQFGKTFRIYQSLNKNAELKGIFNYKT
GITKIVLYTRFRNHSITEQNPLLLLDGTKIEGKVSYKRDNNHFFGNWINYSSFVLT
KSLLERMIKEEDASYKNKEVKIRIGLEDLSLKKYKILDFLVMVESIENKDYKS BBB19: the leader sequence is underlined
(SEQ ID NO:40)
MKKNTLSAILMTLFLFISCNNSGKDGNTSANSADESVKGPNLTEISKKITDSNAVL
LAVKEVEALLSSIDEIAAKAIGKKIHQNNGLDTENNHNGSLLAGAYAISTLIKQKL
DGLKNEGLKEKIDAAKKCSETFTNKLKEKHTDLGKEGVTDADAKEAILKTNGTK
TKGAEELGKLFESVEVLSKAAKEMLANSVKELTSPVVAESPKKP BBC10: the leader sequence is underlined
(SEQ ID NO:41)
MQKINIAKLIFILIFSLFVISCELFIIKRRATITETTTIEKKRINWLIMSVSGLNDEADE
VAFKHCREKISLLKEDLKYATNAKEFEEKFLNLQKLFQEKLTSKLNALKAVRVDI
QRFNANDNDDLEKNKLKIRSIALSAGVNTSPIALHAINIKELSEDVVAHIDSIIKYL
EED BBE09: the leader sequence is underlined
(SEQ ID NO:42)
MQKDIYISNIFLYIPLFYSCFLTPPKSLKINSIKTEVFDFKIIEEGDITKYNKNPIKES
NNNICLTFKEPELNEIKEGEVFEILANGYVTWAKSGDLRDIKDKNNNLIEDLRELK
YSYIFSPIRFKTYSLLTFSYTNYSINDNNYKIFGQEVPIAKIIAFESTEEFEKKYEIKS
LKLNSEESNIDFEQNRTGFAKINLKETSREPQYIYSYNFGVFDNSLADYFKLFYKK
SKCNYMPAYLTIKDKQTNKDKTYEIILNLKLFNDAIRLIFDKYSNLSKEKLKLFID
E BBE16: the leader sequence is underlined
(SEQ ID NO:43)
MGKILPFGLLLICIFLGFFFYKQKENNVIYNKIVEKFDDNVFVDETYTYLFKDSNL
KELVFIKSQLIIPELKHKKMIKATGYRADAYKALSTVYRFDFKVHDNKILGFKSVI
FEGFEDAKVSKHENNLPSEKWQQLKDFNIGDPNINEKFFHLEFPFVVKNTLCVTIS
KGFFKKIKKLKRLKIMLISNEDREYKIDIENFLPKYNL BBH06: the leader sequence is underlined
(SEQ ID NO:44)
MKKSFLSIYMLISISLLSCDVSRLNQRNINELKIFVEKAKYYSIKLDAIYNECTGAY
NDIMTYSEGTFSDQSKVNQAISIFKKDNKIVNFKELEKIIEEYKPMFLSKLIDDFA
IELDQAVDNDVSNARHVADSYKKLRKSVVLAYIESFDVISSKFVDSKFVEASKKF
VNKAKEFVEENDLIALECIVKTIGDMVNDREINSRSRYNNFYKKEADELGAAVEL
EGAYKAIKQTLL -continued BBI29:
(SEQ ID NO:45)
MKNNIILCMCVFLLLNSCTANHEAEAKIKKHVDKTKNEYINEIKNLIATTKEIIEK
RKLLQAKPVDQNPVDDTNNKKVFEIDKRAFDFINSFLTDDEFNKFVTIFHKPTLK
SPGKVLNSIAILELNIEQVINHLDSKNETLNKASSLDLEKIKNSLEQLFSIRNFFSTII
KRVLLDHQNNENSIKPDDSKSGTYFDTIYDQFNEKNKEVRNLKKTILSLPN BBI36: the leader sequence is underlined
(SEQ ID NO:46)
MKNFKLNTIKLNVITAILTLICISCAPFGNVNPNKLKNPITSKNLKKTKRSNHSRNL
KKTNSHTNSENSAENNQNLENESQNSKSSNQNPQEETAISKLEKIGKDLEAQKKE
KDTQIEKISSDAQYDFLENFKLHNYDYFMHNTKMTLKKIIYSSLNYEKEKILTLKE
ILEKLDTEDNNRRIAGQFLETSRDIQLQQEDLILKKIQDTLQTLSKEKAEELLQHA
ERDLKIKQNFVKALNATIEAYNKNSDNIKTDVEALANHMEKKYSHPLYLLDQAD BBI39:
(SEQ ID NO:47)
MKNFKLNIIKLNVITAILTSICISCAPFGNVNPNEPKNPTTSKSLKKTKRSNNSRNL
KNTSNHTNSENLTGNSTKNPSENNQNLENESQNSKSSNQNSQEETTISKLKNIGK
DLEAQKKKEDTGITKMSKIDNAKYDFLETFKLKQDDVFMFHAKMKLKRIIYPSL
NYDTKKILVLKEILEKLDTEDNNRRIAGQFLETSRDIQLHLEDTYLKKIQDTLQTL
SEKEAEKLLQGVKLDLKKKQNFAKSLNATIDAYNKNVDNIKIDNKALAKHIKDK
YSHPLYLLNQAD BBJ41:
(SEQ ID NO:48)
MKIKFLTISLAILLANLIIILLNLVLFIVNTSTSSPYIVPSEKIDILHQSNTGAVKFKIS
LINHLGSVAIVYDYNSASERFYLDFEIVTNKKPFNLLDVSLNDVVIKPEVLLASNS
KLRFEEGQYVLNFDDSIEKTGFFVDLDLRNEYLNLAEIARISGINFRVKCIERETG
VLRNVLFKLSVEKGKKFFDLIERYNNNIGKVS BBK01: the leader sequence is underlined
(SEQ ID NO:49)
MRKSLFLYALLMGGLMSCNLDSKLSSNKEQKNNNNVKEVSDSVQEDGLNDLY
NNQEKQKSFTKNFGERKYEDLINPIEPIIPSESPKNKANIPNISIAHTEKKETKKENL
IPSTNEEKEADAAIKYLEENILKNSKFSELIREVRVIKDEYALIKADLYDVIGKINN
KKTSLMENPKNNRDKINKLTQLLQNNLKIDSELEQLINMIDMAENEISSAAFFFD
NAQKRLKESIIKRLESKNNRSYALKLSRQALSDARSALSNLESFASKRIEPMVRKE
EIKELIKHAKTVLESLNKK BBK32: the leader sequence is underlined
(SEQ ID NO:50)
MKKVKSKYLALGLLFGFISCDLFIRYEMKEESPGLFDKGNSILETSEESIKKPMNK
KGKGKIARKKGKSKVSRKEPYIHSLKRDSANKSNFLQKNVILEEESLKTELLKEQ
SETRKEKIQKQQDEYKGMTQGSLNSLSGESGELEEPIESNEIDLTIDSDLRPKSSLQ
GIAGSNSISYTDEIEEEDYDQYYLDEYDEEDEEEIRLSNRYQSYLEGVKYNVDSAI
QTITKIYNTYTLFSTKLTQMYSTRLDNFAKAKAKEEAAKFTKEDLEKNFKTLLNY
IQVSVKTAANFVYINDTHAKRKLENIEAEIKTLIAKIKEQSNLYEAYKAIVTSILLM
RDSLKEVQGIIDKNGVWY BBK45: the leader sequence is underlined
(SEQ ID NO:51)
MNLMIKVLIFSLFLSFISCKLYEAVDKSLIKDNKRSGRKARSISYKEVNNQEQNNE
KNLKEAKESKKNNNLGIQKDGIVNTNPSVASDASEKHTNRQPQQVNNNSRETSE
ARNIIQEIYTSLEEVNKITTDLETIKSRLNNIKSKVDNASSFLNNARKSNKANPTLL
PKLDQAIRKVSSSHAYANSNYSDAVSALKSSKHDFEYANRKAEDALQEALNNSN
TQGYQYARYHYYMNDAKEAMGRAKVSLKTAKQKQEKLKDKMDQANKEFEEL
NKAHEAALSSRES BBK48: the leader sequence is underlined
(SEQ ID NO:52)
MNLINKLFILTILFSSVISCKLYKKITYNADQVIDKLKSNNGSFNTLKSNDDSKRSG
RKPRSVDNTYMDQDTGKKPLMADMQPDMQNDNSSSNHTLQVNIQDNEASEAR
NIMTEIESSKEEYNRINEDLAKVKASLDKIKSLLSTAKSYLEQTRRGVGSSKANLA
LLPSLEEAIAKVKSNHASADTHCNDAIAALKRAKNDFEYAQRKADRALEEALSN
SNASRHESYYYAGYHQPMADAKASMSSTKSLLEVAKNKQKELNENMTKTNKD
FQELNDIYKKLQDMDSR BBK50: the leader sequence is underlined
(SEQ ID NO:53)
MNLIIKVMLISSLFSSFISCKLYEKLINKSQQALAKAFVYDKDIADNKSTNSTSKL
DNSSLDSIKDNNRSGRTSRALDDAEEIGVKESNQNRNDQQQNNESKVKESEKNN
SSGIQADDSVLDTAHSDASEVENKKHDTSRQPQLLNKDSSEAREASKIIQKASTSL
EEAEKVNAALKETRSKLDKIKRLADSAKSYLNNARKNSRTNGSILEILPNLDKAIE
KAISSYASLNVCYTDAIAALAKAKNDFEHAKRKANDALEEALKDIPHFRGYNYL
YHYRINNANDAMESAKSLLEVAKNKQKELNENMTKTNKDFQELNDIYKKLQD
MDSR -continued BBK52: the leader sequence is underlined
(SEQ ID NO:54)
MKKNIYILNIFLYIPLFYSCFLTPPKSSKINSIKTEVLDFKIIEEGNIIKYDKKPIEERN
ENTCLSFKEPELNEIKEGDVLELLAGGYVTWAKSGDLRVLKDKNNNLIEDLREL
RYSYIFSPIRFKTFFSYNYSINDNNYKILGKKAPIVKIIAFESTKEFEKKYEINSLKL
NSEESNIDFEQNRTGLAKINLKETSKEPNYIYSYNFGVFDNSLADYFKLFYKKNN
CNYMPAYLTIKDKETDKYKTYEIILNLKLFNDTIKLLINKYSNLSKEKLKLFTDE BBL39: the leader sequence is underlined
(SEQ ID NO:55)
MEKFMNKKMKMFIICAVFILIGACKIHTSYDEQSNGEVKVKKIEFSEFTVKIKNK
NNSNNWADLGDLVVRKEKDGIETGLNAGGHSATFFSLEEEEINNFIKAMTEGGSF
KTSLYYGYNDEESDKNVIKNKEIKTKIEKINDTEYITFLGDKINNSAGGDKIAEYA
ISLEELKRNLK BBM27: the leader sequence is underlined
(SEQ ID NO:56)
MRNKNIFKLFFASMLFVMACKAYVEEKKEIDSLMEDVLALVNDSSGGKFKDYK
DKINELKENLKDIGNAELKEKLLNLQNSFQDKLAAKLAALKAAKNTIENITDKD
QDISKRKIWSEAKLVGVTVPLLGSNTSGNGDKMSKNAVEQIDKVIKFLEEGTN BBM28: the leader sequence is underlined
(SEQ ID NO:57)
MKIINILFCLFLLLLNSCNSNDNDTLKNNAQQTKSRGKRDLTQKEATPEKPKSKE
ELLREKLSEDQKTHLDWLKEALGNDGEFDKFLGYDESKIKSALNHIKSELDKCT
GDNSEQQKSTFKQTVQGFFSGGNIDNFANNAVSNCNNGGS BBM38: the leader sequence is underlined
(SEQ ID NO:58)
MNKKMFIICAIFALIVSCKNYASGEDVKKSLEQDLKGKVKGFLDTKKEEFFGDFK
KPEAKVQPKDEESMQADEPQEQGEDQVVQGVAEDQKLKEEIEQKIKELKDKIEK
SDPKSVSLKTYSDYEKEIEELKEKLKDKEKFEKELEILEKALNEKIEKRKKELEES
QKKFEELKGQVESAIGITDGERAKNQGKVGIEALRHARGLGFKNISSGNSTSDIA
KELIVSSLKKIEEELEELKKLEKESKDSNKKE BBN38: the leader sequence is underlined
(SEQ ID NO:59)
MNKKMKMFIVCAVFILIGACKIHTSYDEQSSGEINHTLYDEQSNGELKLKKIEFSK
FTVKIKNKDNNSNWTDLGDLVVRKEENGIDTGLNAGGHSATFFSLKESEVNNFI
KAMTKGGSFKTSLYYGYKYEQSSANGIQNKEIITKIESINGAEHIAFLGDKINNGV
GGDKTAEYAIPLEVLKKNLK BBN39: the leader sequence is underlined
(SEQ ID NO:60)
MNKKTLIICAVFALIISCKNFATGKDIKQNSEGKIKGFVNKILDPVKDKIASSGTKV
DEVAKKLQEEEKEELMQGDDPNGSGINPPPVLPENIHNNALVLKAIEQSDGQQEK
KVEEAEAKVEENKEKQENTEEENIKEKEIIDEQNKQELAKAKEEEQQKEQKRHQE
EQQRKAKAEKEKREREEAEQQKRQQEEEEKRQVDNQIKTLIAKIDEINENIDVIK
WQTTVGPQGVIDRITGPVYDDFTNGNNSIRETWEGLEEESEDEGLGKLLKELSDA
RDALRTKLNEGNKPYTGYEEPKLKESVNVSEIKEDLEKLKSKLEEVKKYLKDSS
KFEEIKGYISDSQ BBO39: the leader sequence is underlined
(SEQ ID NO:61)
MNKKMKMFIICAVFALMISCKNYASGENLKNSEQNLESSEQNVKKTEQEIKKQV
EGFLEILETKDLSKLDEKDTKEIEKQIQELKNKIEKLDSKKTSIETYSEYEEKINKIK
EKLKGKGLEDKFKELEESLAKKKGERKKALQEAKQKFEEYKKQVDTSTGKTQG
DRSKNRGGVGVQAWQCANELGLGVSYSNGGSDNSNTDELANKVIDDSLKKIEE
ELKGIEEDKKE BBO40: the leader sequence is underlined
(SEQ ID NO:62)
MNKKILIIFAVFALIISCKNYATGKDIKQNAKGKIKGFLDKVLDPAKDKITSSSSKV
DELAKKLQEEDEDNELMQGDDPNNRAIALLPVLPENSHDNPPVPKVKAAAQSG
GQQEDQKAKESKDKVEEEKEVVEEKKEEQDSKKEKVEKQSQKQKEEERNSKEE
QQKQEEAKARADREREERLKQQEQKRQQEEARVKAEKEKQEREEQQKQEEEKK
VKYKIKTLTDKIDEINKDIDGINGKTIVGAEEVIDKITGPVYDDFTDGNKAIYKTW
GDLEDEEGEELGKLLKELSDTRHNLRTKLNEGNKAYIVLEKEPNLKENVNVSDIQ
SDLEKLKSGLEEVKKYFENEDNFEEIKGYIEDSNSY BBP39: the leader sequence is underlined
(SEQ ID NO:63)
MNKKTIIICAVFALILSCKNYAIKDLEQNAKGKIKGFIDKALDPAKDKITSSSSKVD
ELARKLQEEDKIKGVEENNKDELMQGDDPNSGVINSSPVLPENSQDNTPILKAAE
QSDGQQEEKVKKVEESEAKVEGKEEKQENTEERNKQELAKQEEEQQKRKAEQE
KQKREEEQERQKREEEQERKAKAEKEAKEKAERQKQEEQQKRKAEKEREEQRK
EAEKRQVDNEIRTLTGKIDEINRNIDVIKEQTSVGAQGVIDRITGPVYDDFTDGNK
AIYKTWGDLEDDNDEGLGKLLKELSDTRHNLRTKLNEGNKA YIIDTRSTEPQLKE
NVSVSEIKSDLDELKSKLEEVKEYLEDKDNFEEIKEYVAGSEDNYDEED -continued BBQ47: the leader sequence is underlined
(SEQ ID NO:64)
MNKKMKIFIICAVFVLISSCKIDATGKDATGKDATGKDATGKDATGKNAEQNIK
GKVQGFLEKILDPVKDKIASNGPIADELAKKLQEEEKVNNGEEENDKAVFLGEES
KEDEEENEQAVNLEEKNAEEDKKVVNLEEKELEVKKETEEDEDKEEIEKQKQEV
EKAQERKQRQEEKKRKKQEQQEEKKRKRQEQRKERRAKNKIKKLADKIDEISW
NIDGIESQTSVKPKAVIDKITGPVYDYFTDDNKKAIYKTWGDLEDEEGEGLGKLL
KELSDTRDELRTKLNKDNKKYYAHENEPPLKENVDVSEIKEDLEKVKSGLEKVK
EYLKDNSKFEEIKGYISYSQ BBR28: the leader sequence is underlined
(SEQ ID NO:65)
MKIINILFCLFLLMLNGCNSNDTNNSQTKSRQKRDLTQKEATQEKPKSKEELLRE
KLNDNQKTHLDWLKEALGNDGEFNKFLGYDESKIKSALDHIKSELDSCTGDKVE
NKNTFKQVVQEALKGGIDGFENTASSTCKNS BBR42: the leader sequence is underlined
(SEQ ID NO:66)
MNKKIKMFIICAIFMLISSCKNDVTSKDLEGAVKDLESSEQNVKKTEQEIKKQVE
GFLEILETKDLNTLDTKEIEKQIQELKNKIEKLDSKKTSIETYSGYEEKINKIKEKL
NGKGLEDKLNELSESLKKKKEERKKALQEAKKKFEEYKNQAESATGVTHGSQV
QRQGGVGLQAWQCANSLGFKNMTSGNNTSDMTNEVITNSLKKIEEELKNIGETV
EGKKE BBS30: the leader sequence is underlined
(SEQ ID NO:67)
MKIINILFCLFLLMLNGCNSNDNDTLKNNAQQTKRRGKRDLTQKETTQEKPKSK
EELLREKLSDDQKTHLDWLKPALTGAGEFDKFLENDDDKIKSALDHIKTQLDSC
NGDQAEQQKTTFKTVVTEFFKNGDIDNFATGAVSNCNNGG BBS41: the leader sequence is underlined
(SEQ ID NO:68)
MNKKMKNLIICAVFVLIISCKIDASSEDLKQNVKEKVEGFLDKELMQGDDPNNSL
FNPPPVLPASSHDNTPVLKAVQAKDGGQQEGKEEKEKEIQELKDKIDKRKKELEE
ARKKFQEFKEQVESATGESTEKVKKQGNIGQKALKYAKELGVNGSYSVNDGTN
TNDFVKKVIDDALKNIEEELEKLAEPQNIEDKK DbpB-F2 ("F" stands for "fragment")
(SEQ ID NO:69)
LESSSKDLKNKILKIKKEATGKGVLFEAFTGLKTGSKVTSGGLALNNPINTAERLL
AAKAQIENQLKVVKEKQNIENGGEKKNNKSKKKK BBA73-F5 ("F" stands for "fragment")
(SEQ ID NO:70)
NTEAISELQSSPIKLGKIKVLQKTEKIVSTQNLQNLQQSQFFKNEKEKIIKKIAQEF
DENEKLINKIGPNIEMFAQTINTDIQKIEPNDQFGINKTLFTEKKDNNIDFMLKDNR
LRRLFYSSLNYDENKIKKLATILAQTSSSNDYHYTLIGLIFWTGFKIQEAFESAVNI
LTKDEQKRLIFNFRTKTVKEIQENFEKLM BB0238-F2 ("F" stands for "fragment")
(SEQ ID NO:71)
DKQKELAIFYYEVGQRYINVGKIKKGKLFQAKALKIYPDLKKGFDIKLAVKELD
ARIKDDNPKVVSTLSSASSKADADELEYLSVDDYYDLKSLKISKSNDTSFAVNVN
AKKNDVTKNFPFWKERQTLIFTTEDDNNWFLSSINF
and BBK53-F1 ("F" stands for "fragment")
(SEQ ID NO:72)
NKFFLDLGSEQSKDLIKLFIMVKNEQNNNKFMRIVRWLYSCIEELYSLDIKYSGE
GSHEYNRNMPRPTAYEQYLKVKRYDYNSPVSILPT.

Exemplary chimeric proteins that comprise at least two, and generally 3 or 4, of these sequences include but are not limited to:
i) DCFL4 (SEQ ID NO: 1) which comprises, in order from amino to carboxy terminus, the four proteins: DbpB with the amino terminal A deleted (SEQ ID NO: 76) (wavy underline); BBA73 (SEQ ID NO: 3) (bold); BBK53 (SEQ ID NO: 4) (no underline) and BB0238 (SEQ ID NO: 5) (italics).

DCFL4:
(SEQ ID NO: 1)
LESSSKDLKNKILKIKKEATGKGVLFEAFTGLKTGSKVTSGGLALREAK
VQAIVETGKFLKIIEEEALKLKETGNSGQFLAMFDLMLEVVESLEDVGI

-continued
IGLKARVLEESKNNPINTAERLLAAKAQIENQLKVVKEKQNIENGGEKK
NNKSKKKKNTEAISELQSSPIKLGKIKVLQKTEKIVSTQNLQNLQQSQF
FKNEKEKIIKKIAQEFDENEKLINKIGPNIEMFAQTINTDIQKIEPNDQ
FGINKTLFTEKKDNNIDFMLKDNRLRRLFYSSLNYDENKIKKLATILAQ
TSSSNDYHYTLIGLIFWTGFKIQEAFESAVNILTKDEQKRLIFNFRTKT
VKEIQENFEKLMQERNSWIKIVDNIIGEYDKNTGGCKADGKILGEVIRV
GYEHELDSNKSMQILNNIETPLKTCCDHIHYDKQKELAIFYYEVGQRYI
NVGKIKKGKLFQAKALKIYPDLKKGFDIKLAVKELDARIKDDNPKVVML -continued
EDIKLEEIPGIVHEKIEINDFTNAPKIEYIAQRERSKNQDKIIKFQFGK

FARALISRNFDLFDSVIADKVNVMGQFESKNDFISTLSSASSKADADEL

EYLSVDDYYDLKSLKISKSNDTSFAVNVNAKKNDVTKNFPFWKERQTLI

FTTEDDNNWFLSSINQTFFENSESSSDMGSDEIVTEGIFSSLKLYASEHR

LLVEIKKTLISLKDPNYRDVVRPVSDYNEEYFNKFFLDLGSEQSKDLIK

LFIMVKNEQNNNKFMRIVRWLYSCIEELYSLDIKYSGEGSHEYNRNMPR

PTAYEQYLKVKRYDYNSPVSILPT;

ii) DCFL3A (SEQ ID NO: 6) which comprises, in order from amino to carboxy terminus, the three proteins DbpB with the amino terminal A deleted (SEQ ID NO: 76) (wavy underline), BBA73 (SEQ ID NO: 3) (bold) and BBK53 (SEQ ID NO: 4) (no underline).

DCFL3A:
(SEQ ID NO:6)
LESSSKDLKNKILKIKKEATGKGVLFEAFTGLKTGSKVTSGGLALREAK

VQAIVETGKFLKIIEEEALKLKETGNSGQFLAMEDLMLEVVESLEDVGI

IGLKARVLEESKNNPINTAERLLAAKAQIENQLKVVKEKQNIENGGEKK

NNKSKKKKNTEAISELQSSPIKLGKIKVLQKTEKIVSTQNLQNLQQSQF

FKNEKEKIIKKIAQEFDENEKLINKIGPNIEMFAQTINTDIQKIEPNDQ

FGINKTLFTEKKDNNIDFMLKDNRLRRLFYSSLNYDENKIKKLATILAQ

TSSSNDYHYTLIGLIFWTGFKIQEAFESAVNILTKDEQKRLIFNFRTKT

VKEIQENFEKLMQERNSWIKIVDNIIGEYDKNTGGCKADGKILGEVIRV

GYEHELDSNKSMQILNNIETPLKTCCDHIHYQTFFENSESSDMGSDEIV

TEGIFSSLKLYASEHRLLVEIKKTLISLKDPNYRDVVRPVSDYNEEYFN

KFFLDLGSEQSKDLIKLFIMVKNEQNNNKFMRIVRWLYSCIEELYSLDI

KYSGEGSHEYNRNMPRPTAYEQYLKVKRYDYNSPVSILPT;

and iii) HDFL4 (SEQ ID NO: 10) which comprises, in order from amino to carboxy terminus, the four proteins DbpA (SEQ ID NO: 13) (wavy underline), DbpB, (SEQ ID NO: 2) (bold), BBK19 (SEQ ID NO: 15) (no underline), VlsE (SEQ ID NO: 16) (italics).

HDFL4:
(SEQ ID NO: 10)
TKIRLERSAKDITDEIDAIKKDAALKGVNFDAFKDKKTGSGVSENPFIL

EAKVRATTVAEKFVIAIEEEATKLKETGSSGEFSAMYDLMFEVSKPLQK

LGIQEMTKTVSDAAEENPPTTAQGVLEIAKKMREKLQRVHTKNYCTLKK

KENSTFTDEKCKNNALESSSKDLKNKILKIKKEATGKGVLFEAFTGLKT

GSKVTSGGLALREAKVQAIVETGKFLKIIEEEALKLKETGNSGQFLAMF

DLMLEVVESLEDVGIIGLKARVLEESKNNPINTAERLLAAKAQIENQLK

VVKEKQNIENGGEKKNNKSKKKKNLFSKDSRSRQKYNFKVPAKSVSNPI

NKENIDTEKGTNTTLCIKEKDSRIIIKDCINNQELFKVKSKRRYDFKKA

MLLGIQTALKVINIGNNNKKLTSIKKHNDHILLEFKDNKIYIIRLSELK

KHLLKSKKKPLLGSPIPGGGDAEFVDDPDGRIEAELEAEQEQEMLDRED

FGDEEDEELEEEIFGKEKPNN*DKDDPTNKFYQSVIQLGNGFLDVFTSFG*

*GLVAEAFGFKSDPKKSDVKTYFTTVAAKLEKTKTDLNSLPKEKSDISST*

*TGKPDSTGSVGTAVEGAIKEVSELLDKLVKAVKTAEGASSGTAAIGEVV*

*ADADAAKVADKASVKGIAKGIKEIVEAAGGSEKLKAVAAAKGENNKGAG*

*KLFGKAGAAAHGDSEAASKAAGAVSAVSGEQILSAIVTAADAAEQDGKK*

*PEEAKNPIAAAIGDKDGGAEFGQDEMKKDDQIAAAIALRGMAKDGKFAV*

*KDGEKEKAEGAIKGAAESAVRKVLGAITGLIGDAVSSGLRKVGDSVKAA*

*SKETPPALNK*

TABLE A

Selected constructs and associated components and SEQ ID NOS:

| Name of the chimera | Components |
|---|---|
| DCFL4 (SEQ ID NO: 1) | DbpB (with N terminal A deleted) (SEQ ID NO:76) BBK73 (SEQ ID NO:3) BBA53 (SEQ ID NO:4) BB0238 (SEQ ID NO:5) |
| DCFL3A (SEQ ID NO: 6) | DbpB (with N terminal A deleted) (SEQ ID NO:76) BBA73 (SEQ ID NO:3) BBK53 (SEQ ID NO:4) |
| HDFL4 (SEQ ID NO: 10) | DbpA (SEQ ID NO:13) DbpB (SEQ ID NO:2) BBK19 (SEQ ID NO:15) VlSE (SEQ ID NO:16) |

For comparison, the sequence of another chimera, DCFL3B, is provided below. This chimeric provided low sensitivity for detecting antibody in serum from infected mammals. Note that the genes represented in this construct are also in DCFL4 which has high sensitivity and specificity. It can be concluded that gene order and composition are critical and not obvious. The order of the genes in this construct is: DbpB (SEQ ID NO: 76) (wavy underline), BB0238 (SEQ ID NO: 5) (bold), and BBK53 (SEQ ID NO: 4) (no underline).

DCFL3B:
(SEQ ID NO: 7)
LESSSKDLKNKILKIKKEATGKGVLFEAFTGLKTGSKVTSGGLALREAK

VQAIVETGKFLKIIEEEALKLKETGNSGQFLAMFDLMLEVVESLEDVGI

IGLKARVLEESKNNPINTAERLLAAKAQIENQLKVVKEKQNIENGGEKK

NNKSKKKKDKQKELAIFYYEVGQRYINVGKIKKGKLFQAKALKIYPDLK

KGFDIKLAVKELDARIKDDNPKVVMLEDIKLEEIPGIVHEKIEINDFTN

APKIEYIAQRERSKNQDKIIKFQFGKFARALISRNFDLFDSVIADKVNV

MGQFESKNDFISTLSSASSKADADELEYLSVDDYYDLKSLKISKSNDTS

FAVNVNAKKNDVTKNFPFWKERQTLIFTTEDDNNWFLSSINQTFFENSE

SSDMGSDEIVTEGIFSSLKLYASEHRLLVEIKKTLISLKDPNYRDVVRP

VSDYNEEYFNKFFLDLGSEQSKDLIKLFIMVKNEQNNNKFMRIVRWLYS

CIEELYSLDIKYSGEGSHEYNRNMPRPTAYEQYLKVKRYDYNSPVSILP

T

An example of a construct that did not provide good specificity and sensitivity is REBE. It comprises segments (fragments) of: DbpB-F2 (SEQ ID NO: 69) (wavy underline), BBA73-F5 (SEQ ID NO: 70) (bold), BB0238-F2 (SEQ ID NO: 71) (no underline), and BBK53-F1 (SEQ ID NO: 72) (italics). The "F" stands for "fragment".

REBE:
(SEQ ID NO: 73)
LESSSKDLKNKILKIKKEATGKGVLFEAFTGLKTGSKVTSGGLALNNPI

NTAERLLAAKAQIENQLKVVKEKQNIENGGEKKNNKSKKKKNTEAISEL

QSSPIKLGKIKVLQKTEKIVSTQNLQNLQQSQFFKNEKEKIIKKIAQEF

DENEKLINKIGPNIEMFAQTINTDIQKIEPNDQFGINKTLFTEKKDNNI

DFMLKDNRLRRLFYSSLNYDENKIKKLATILAQTSSSNDYHYTLIGLIF

WTGFKIQEAFESAVNILTKDEQKRLIFNFRTKTVKEIQENFEKLMDKQK

ELAIFYYEVGQRYINVGKIKKGKLFQAKALKIYPDLKKGFDIKLAVKEL

DARIKDDNPKVVSTLSSASSKADADELEYLSVDDYYDLKSLKISKSNDT

SFAVNVNAKKNDVTKNFPFWKERQTLIFTTEDDNNWFLSSINF*NKFFLD*

*LGSEQSKDLIKLFIMVKNEQNNNKFMRIVRWLYSCIEELYSLDIKYSGE*

*GSHEYNRNMPRPTAYEQYLKVKRYDYNSPVSILPT*.

In some aspects, an entire native or wild type protein (with or without its leader peptide and/or lipidation motif) is present in a chimera. In other aspects, a portion of the wildtype sequence is used, e.g. a peptide segment or segments of at least about 20-25 contiguous amino acids of the protein that comprise(s) epitopes recognized by mammalian antibodies. "At least about 20-25 contiguous amino acids" refers to about 20, 21, 22, 23, 24, or 25 amino acids. In some aspects, the portion of the wildtype sequence is longer, e.g. from about 20 to 200 amino acids, such as about 20, 25, 30, 35, 40, 45, 50, 55, 60, 65, 70, 75, 80, 85, 90, 95, 100, 110, 120, 130, 140, 150, 160, 170, 180, 190 or 200 amino acids.

In some aspects, the at least about 25 contiguous amino acids are the amino acids that remain after a deletion of amino acids from the amino terminus of the protein and/or from the carboxy terminus of the protein. In further aspects, the at least about 25 contiguous amino acids are the amino acids that remain after a deletion of amino acids from within the sequence of the protein (internal deletion) but which are joined by a covalent bond. In other aspects, the at least about 50 contiguous amino acids are the amino acids that remain after one or more of these types of deletion, i.e. they remain after a combination of these types of deletions such as one from the amino and/or carboxy terminus and/or one or more internal deletions. Further, in some aspects, for one protein that is represented in a chimera, the polypeptide (e.g. a first polypeptide) may be full-length or a peptide segment or peptide segments of the native protein from which it is derived, while for the other proteins that are represented in the same chimera (e.g. a second, third, fourth, fifth, etc. polypeptide), the polypeptide is, independent from the first polypeptide, either full length or a peptide segment or peptide segments of the native protein from which it is derived.

In addition, the order of the constituent 2-8 proteins and/or variants thereof may be varied. For example, if four different proteins or variants thereof are present, represented by A, B, C and D, their order within the chimera can be: ABCD, BCDA, CDAB, CABC, ABDC, BACD, etc. with all permutations of these orders permitted, as long as the resulting chimeric polypeptide is capable of the specificity and sensitivity for detecting anti-*Borreliella* antibodies as described herein.

Also encompassed as suitable for inclusion in a chimera are forms (variants) of a wild-type Lyme disease spirochetes protein having at least 50% amino acid sequence identity to i) the amino acid sequence of any individual wildtype Lyme disease spirochete protein disclosed herein or to ii) fragments or segments thereof as disclosed herein or to iii) a complete chimera as disclosed herein. In some aspects, the amino acid sequence of a variant (either a variant of an individual *Borreliella* protein, segment thereof or a variant of a chimeric polypeptide) has at least about 85 to about 100% amino acid identity along the length of the query protein (e.g. a native sequence, segment thereof or a chimera) i.e. about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%, or any fractional percentage in this range. Such sequences can be compared, e.g. to a native sequence, using various computer-based algorithms known in the art, e.g. Clustal W alignment using suitable default parameters, an example of which follows: Weight matrix: blossum, Gap opening penalty: 10.0, Gap extension penalty: 0.05, Hydrophilic gaps: On, Hydrophilic residues: GPSNDQERK, Residue-specific gap penalties: On (Thompson, et al (1994) Nucleic Acids Research, 22:4673-4680). Percent amino acid identity is further calculated by the product of 100% multiplied by (amino acid identities/length of subject protein). Other alignment algorithms are also available in the art and provide results similar to those obtained using a clustal W alignment and are contemplated herein, for example, algorithms (including but not limited to GAP, BESTFIT, FASTA, and TFASTA) etc.; or the BLAST family of programs as for example disclosed in the GCG (Genetics Computer Group) product, the Wisconsin Package 11.0 (or later when available), a recognized industry standard for sequence analysis of nucleic acids and protein sequences; and Ausubel et al., Current Protocols in Molecular Biology, John Wiley & Sons Inc, 2012.

Such protein variants may be included in a chimera, as long as they maintain a suitable, useful level of activity, i.e., as long as they react with anti-*Borreliella* antibodies in a sample to a degree or level that results in a high degree of specificity and sensitivity described herein.

In some aspects, sequences or sequence variants that are present in a chimeric polypeptide are separated from one another by intervening sequences that are more or less neutral in character, i.e. they do not in participate in or contribute to binding to anti-*Borreliella* antibodies. However, they also do not interfere with antibody binding. If present, such sequences may be e.g., artifacts of recombinant processing procedures that are included for practical reasons (e.g., they arise from restriction sites), or for convenience, e.g. to identify the stop and start sites of a sequence within a chimera, etc. Such sequences may be e.g., from about 2-10 amino acids in length, and are typically known as linker or spacer peptides, many examples of which are known to those of skill in the art. See, for example, Crasto, C. J. and J. A. Feng. 2000. Such linker sequences may or may not be included in identity calculations.

In addition, other elements may be present in chimeric proteins, for example sequences that "tag" the protein to facilitate visualization, purification and/or detection of the protein, the addition of a tryptophan residue to the sequence or the substitution of an amino acid in the sequence by a tryptophan residue, Hexahistidine tags, S-tags, Flag-tags, various protein stabilizing motifs, or other N- or C-terminal tags that are added for the purpose of facilitating purification and or detection, etc. Such tagging sequences may or may not be included in identity calculations. In addition, the chimeric proteins may be chemically modified, e.g. by amidation, sulfonylation, lipidation, or other techniques that are known to those of skill in the art.

Generally, the naturally occurring leader sequences of the native proteins are not included in the chimera. However, chimeras in which one or more leader sequences are included are also encompassed.

While generally the compositions disclosed herein comprise at least one chimeric recombinant protein as described herein, in other aspects, compositions are provided which comprise at least one protein, and typically a plurality of proteins, e.g., a cocktail of proteins. The protein or proteins that are selected for inclusion in the cocktail are typically those identified herein as exhibiting high specificity and sensitivity in Lyme disease diagnostic assays in humans and/or animals. In other words, combinations of proteins, or antigenic portions thereof as described herein, that are the same as those included in a recombinant chimera are included in a composition, but they are not covalently linked to each other. Or in other aspects, one or more selected proteins may be included in a composition together with one or more chimeric proteins. Such compositions typically include other components as described for chimeric compositions, i.e. a physiologically compatible buffer or carrier (e.g. a phosphate-buffered saline buffer, citrate buffer, a Good's buffer, etc.) and may further comprise, e.g. a blocking agent (e.g., casein, Tween® reagent, etc.), a surfactant, various additives, and other reagents to increase sensitivity of the assay, as known in the art.

Polynucleotides

Polynucleotide encoding the recombinant chimeric polypeptides, or variants thereof, are provided. As used herein, the terms "polynucleotide" or "nucleic acid" refer to deoxyribonucleic acid (DNA), ribonucleic acid (RNA) and DNA/RNA hybrids. Polynucleotides may be single-stranded or double-stranded and either recombinant, synthetic, or isolated. Polynucleotides include, but are not limited to: pre-messenger RNA (pre-mRNA), messenger RNA (mRNA), plus strand RNA (RNA(+)), minus strand RNA (RNA(−)), PCR amplified DNA, complementary DNA (cDNA), synthetic DNA, or recombinant DNA.

In some aspects, polynucleotides may be codon-optimized for gene expression in E. coli or any other suitable expression cell (insect, mammalian, other bacteria). As used herein, the term "codon-optimized" refers to substituting codons in a polynucleotide encoding a polypeptide in order to increase the expression, stability and/or activity of the polypeptide based on e.g. codon biases between two or more organisms or genes or synthetically constructed bias tables, variation in the degree of codon bias within an organism, gene, or set of genes, systematic variation of codons including context, variation of codons according to their decoding tRNAs, variation of codons according to GC %, either overall or in one position of the triplet, variation in degree of similarity to a reference sequence, for example, a naturally occurring sequence, variation in the codon frequency cutoff, structural properties of mRNAs transcribed from the DNA sequence, systematic variation of codon sets for each amino acid, and/or isolated removal of spurious translation initiation sites.

In some aspects, the polynucleotides encode at least one, and usually only one, of the chimeric polypeptides or a variant thereof as disclosed herein. Various illustrative embodiments of such polynucleotides include but are not limited to those set forth in SEQ ID NOS: 8, 9 and 11 etc., and variants thereof.

Exemplary DNA sequence encoding DCFL4, where the DNA sequence encoding the N-terminal tag that is part of the protein to facilitate expression is underlined and may be present or absent or replaced by a different tag in variants of this sequence.

Exemplary DNA sequence encoding DCFL4:
(SEQ ID NO: 8)
<u>ATGGCACATCACCACCACCATCACGTGGGTACCGGTTCGAATGATGACG</u>
<u>ACGACAAGAGTCCGGATCCCGGT</u>AAAGGCGTGCTGTTCGAGGCGTTTAC
CGGTCTGAAAACCGGCAGCAAGGTTACCAGCGGTGGCCTGGCGCTGCGT
GAAGCGAAGGTGCAGGCGATCGTTGAAACCGGCAAGTTCCTGAAAATCA
TTGAGGAAGAGGCGCTGAAGCTGAAAGAAACCGGTAACAGCGGCCAATT
CCTGGCGATGTTTGACCTGATGCTGGAAGTGGTTGAGAGCCTGGAAGAT
GTGGGTATCATTGGCCTGAAAGCGCGTGTTCTGGAAGAGAGCAAGAACA
ACCCGATCAACACCGCGGAACGTCTGCTGGCGGCGAAAGCGCAGATTGA
GAACCAACTGAAGGTGGTTAAACTGCAGAAGACCGAGAAAATCGTGAGC
ACCCAGAACCTGCAAAACCTGCAGCAAAGCCAGTTCTTTAAGAACGAAA
AGGAGAAGATCATTAAGAAAATTGCGCAAGAATTCGACGAAAACGAGAA
ACTGATCAACAAGATTGGTCCGAACATCGAAATGTTTGCGCAGACCATT
AACACCGACATCCAAAAAATTGAGCCGAACGATCAGTTCGGCATCAACA
AGACCCTGTTTACCGAAAAGAAAGACAACAACATTGATTTCATGCTGAA
AGACAACCGTCTGCGTCGTCTGTTTTACAGCAGCCTGAACTATGATGAG
AACAAGATCAAGAAACTGGCGACCATTCTGGCGCAGACCAGCAGCAGCA
ACGACTACCACTATACCCTGATCGGTCTGATTTTCTGGACCGGCTTTAA
AATTCAGGAAGCGTTCGAAAGCGCGGTGAACATCCTGACCAAAGATGAA
CAAAAGCGTCTGATTTTCAACTTTCGTACCAAGACCGTTAAAGAGATCC
AGGAAAACTTCGAGAAACTGATGCAAGAGCGTAACAGCTGGATCAAGAT
TGTGGACAACATCATTGGTGAATACGATAAAAACACCGGTGGCTGCAAA
GCGGACGGCAAGATCCTGGGCGAGGTGATCCGTGTTGGCTATGAACACG
AGCTGGATAGCAACAAGAGCGGTAAAATCAAGAAAGGCAAGCTGTTCCA
GGCGAAGGCGCTGAAAATCTACCCGGACCTGAAGAAAGGTTTTGATATT
AAACTGGCGGTGAAGGAGCTGGACGCGCGTATCAAAGACGATAACCCGA
AGGTGGTTATGCTGGAAGATATTAAACTGGAAGAGATCCCGGGCATTGT
TCACGAAAAGATCGAGATTAACGACTTCACCAACGCGCCGAAAATCGAA
TATATTGCGCAACGTGAGCGTAGCAAGAACCAGGATAAGATCATCAAGT
TCCAATTCGGCAAGTTTGCGCGTGCGCTGATCAGCCGTAACTTCGACCT
GTTTGATAGCGTTATTGCGGACAAAGTGAACGTTATGGGCCAATTCGAG
AGCAAGAACGATTTTATCAGCACCCTGAGCAGCGCGAGCAGCAAGGCGG
ATGCGGATGAACTGGAGTACCTGAGCGTGGACGATTACTATGACCTGAA
GAGCCTGAAAATCAGCAAGAGCAACGATACCAGCTTCGCGGTGAACGTT
AACGCGAAGAAAAACGACGTTACCAAAAACTTCCCGTTTTGGAAGGAAG
GTATCTTTAGCAGCCTGAAACTGTACGCGAGCGAACACCGTCTGCTGGT
TGAGATCAAGAAAACCCTGATTAGCCTGAAGGACCCGAACTATCGTGAT
GTGGTTCGTCCGGTTAGCGATTACAACGAAGAGTACTTCAACAAGTTCT
TTCTGGACCTGGGTAGCGAGCAGAGCAAAGATCTGATCAAGCTGTTCAT
TATGGTGAAGAACGAACAAAACAACAACAAGTTCATGCGTATCGTTCGT
TGGCTGTACAGCTGCATTGAAGAGCTGTACAGCCTGGACATCAAGTATA
GCGGTGAAGGCAGCCACGAGTACAACCGTAACATGCCGCGTCCGACCGC
GTATTAA Exemplary DNA sequence encoding DCFL3A:
(SEQ ID NO: 9)
GCTGGAGAGCAGCAGCAAGGACCTGAAGAACAAGATCCTGAAGATTAAG
AAAGAAGCGACCGGCAAGGGCGTGCTGTTCGAGGCGTTTACCGGTCTGA
AGACCGGCAGCAAAGTTACCAGCGGTGGCCTGGCGCTGCGTGAAGCGAA
AGTGCAAGCGATCGTTGAGACCGGCAAGTTCCTGAAAATCATTGAGGAA
GAGGCGCTGAAGCTGAAAGAGACCGGTAACAGCGGCCAGTTCCTGGCGA
TGTTTGACCTGATGCTGGAAGTGGTTGAGAGCCTGGAAGATGTGGGTAT
CATTGGCCTGAAAGCGCGTGTTCTGGAAGAGAGCAAGAACAACCCGATC
AACACCGCGGAACGTCTGCTGGCGGCGAAAGCGCAGATTGAAACCAAC
TGAAGGTGGTTAAGGAGAAACAAAACATCGAAAACGGTGGCGAGAAGAA
AAACAACAAGAGCAAGAAAAAGAAAACACCGAAGCGATTAGCGAGCTG
CAAAGCAGCCCGATCAAGCTGGGCAAGATTAAAGTGCTGCAGAAGACCG
AGAAAATCGTTAGCACCCAGAACCTGCAAAACCTGCAGCAAAGCCAATT
CTTTAAGAACGAAAAGGAGAAGATCATTAAGAAAATCGCGCAGGAATTC
GACGAAAACGAGAAGCTGATCAACAAAATTGGTCCGAACATCGAAATGT
TTGCGCAGACCATTAACACCGACATCCAAAAAATTGAGCCGAACGATCA
GTTCGGCATTAACAAGACCCTGTTTACCGAAAAGAAAGACAACAACATC
GATTTCATGCTGAAAGACAACCGTCTGCGTCGTCTGTTTTACAGCAGCC
TGAATATGATGAGAACAAGATCAAGAAATGGCGACCATTCTGGCGCA
GACCAGCAGCAACGACTACCACTATACCCTGATCGGTCTGATTTTC
TGGACCGGCTTTAAAATTCAGGAGGCGTTCGAAAGCGCGGTGAACATCC
TGACCAAGGATGAACAGAAACGTCTGATTTTCAACTTTCGTACCAAGAC
CGTTAAAGAGATCCAAGAAAACTTTGAGAAACTGATGCAGGAGCGTAAC
AGCTGGATCAAGATTGTGGACAACATCATTGGTGAATACGATAAGAACA -continued
```
CCGGTGGCTGCAAGGCGGACGGTAAAATCCTGGGCGAGGTGATCCGTGT
TGGCTATGAACACGAGCTGGATAGCAACAAAAGCATGCAAATCCTGAAC
AACATTGAAACCCCGCTGAAGACCTGCTGCGACCACATCCACTACCAGA
CCTTCTTTGAAAACAGCGAGAGCAGCGACATGGGTAGCGATGAAATCGT
GACCGAGGGCATTTTCAGCAGCCTGAAACTGTACGCGAGCGAACACCGT
CTGCTGGTTGAGATCAAGAAAACCCTGATTAGCCTCGAAGGACCCGAACT
ATCGTGATGTGGTTCGTCCGGTTAGCGATTACAACGAAGAGTACTTCAA
CAAGTTCTTTCTGGACCTGGGTAGCGAGCAAAGCAAGGATCTGATCAAA
CTGTTCATTATGGTGAAGAACGAACAGAACAACAACAAATTTATGCGTA
TCGTTCGTTGGCTGTACAGCTGCATTGAAGAGCTGTACAGCCTGGACAT
CAAGTATAGCGGTGAAGGCAGCCACGAGTATAACCGTAACATGCCGCGT
CCGACCGCGTACGAGCAGTATCTGAAGGTGAAACGTTACGATTATAACA
GCCCGGTTAGCATCCTGCCGACCTAA Exemplary DNA sequence encoding HDFL4:
                                            (SEQ ID NO:11)
ACAAAAATTAGATTAGAACGAAGCGCTAAAGACATTACAGATGAAATAG
ATGCAATTAAAAAAGACGCTGCTCTTAAGGGCGTAAATTTTGATGCCTT
TAAAGATAAAAAAACGGGTAGTGGGGTATCAGAAAATCCATTCATACTT
GAAGCAAAAGTGCGAGCTACTACAGTAGCGGAAAAATTCGTAATAGCAA
TAGAAGAGGAAGCTACTAAACTCAAAGAAACTGGAAGTAGTGGTGAATT
TTCAGCAATGTATGATTTAATGTTTGAAGTCTCAAAACCATTACAAAAA
TTGGGAATACAAGAGATGACAAAAACAGTCTCAGATGCAGCTGAAGAGA
ATCCTCCAACTACAGCTCAAGGAGTGCTTGAAATTGCAAAAAAAATGAG
AGAAAAATTACAAAGGGTTCATACAAAAAACTACTGCACCCTTAAAAAG
AAGGAAAATTCTACTTTTACTGATGAAAAATGCAAAAATAACGCTCTTG
AATCGTCCTCTAAGGATTTAAAAAACAAAATTTTAAAAATAAAAAAAGA
AGCCACGGGAAAAGGTGTACTTTTTGAAGCTTTTACAGGTCTTAAAACC
GGTTCCAAGGTAACAAGTGGTGGACTAGCCTTAAGAGAAGCAAAAGTAC
AAGCCATTGTTGAAACAGGAAAGTTCCTTAAGATAATAGAAGAAGAAGC
TTTAAAGCTTAAAGAAACTGGAAACAGTGGTCAATTCTTGGCTATGTTT
GACTTAATGCTTGAGGTTGTAGAATCGCTAGAAGACGTTGGAATAATAG
GCTTAAAAGCCCGTGTTTTAGAGGAATCTAAAAATAATCCTATAAACAC
AGCTGAAAGATTGCTTGCGGCTAAAGCTCAAATAGAAAATCAACTTAAA
GTGGTTAAGGAAAAACAAAATATTGAAAATGGTGGAGAGAAAAAAAATA
ATAAAAGCAAAAAAAGAAAAATCTTTTTTCAAAAGATTCTCGATCACG
CCAAAAATACAATTTTAAAGTACCCGCTAAATCGGTTTCAAATCCTATC
AATAAAGAAAATATAGACACTGAAAAAGGTACTAACACTACACTTTGCA
TAAAAGAAAAAGATAGCAGAATTATAATTAAAGATTGTATTAATAATCA
AGAGCTTTTTAAAGTAAAATCTAAAAGAAGATATGATTTTAAAAAAGCC
ATGCTTCTTGGAATTCAAACAGCTTTAAAAGTTATAAATATTGGCAATA
ATAATAAAAAATTAACTTCCATAAAAAAACATAATGATCATATTTTATT
AGAATTTAAAGATAATAAGATATATATAATTCGATTATCTGAACTTAAA
AAACATTTACTAAAAAGCAAGAAAAAACCACTATTAGGAAGTCCGATAC
CGGGCGCGGAGATGCAGAATTTGTAGATGATCCTGATGGCAGAATAGA
AGCAGAATTAGAGGCAGAACAAGAGCAAGAGATGTTAGATAGAGAAGAT
TTTGGAGCGAAGAAGCAGAAGAACTTAGAGAAGAAATATTTGGAAAAG
AAAAACCTAACAATGATAAGGACGACCCAACAAACAAATTTTACCAATC
TGTCATACAATTAGGTAACGGATTTCTTGATGTATTCACATCTTTTGGT
GGGTTAGTAGCAGAGGCTTTTGGATTTAAATCAGATCCAAAAAAATCTG
ATGTAAAAACCTATTTTACTACTGTAGCTGCCAAATTGGAAAAAACAAA
AACCGATCTTAATAGTTTGCCTAAGGAAAAAAGCGATATAAGTAGTACG
ACGGGGAAACCAGATAGTACAGGTTCTGTTGGAACTGCCGTTGAGGGGG
CTATTAAGGAAGTTAGCGAGTTGTTGGATAAGCTGGTAAAAGCTGTAAA
GACAGCTGAGGGGCTTCAAGTGGTACTGCTGCAATTGGAGAAGTTGTG
GCTGATGCTGATGCTGCAAAGGTTGCTGATAAGGCGAGTGTGAAGGGGA
TTGCTAAGGGGATAAAGGAGATTGTTGAAGCTGCTGGGGGGAGTGAAAA
GCTGAAAGCTGTTGCTGCTGCTAAAGGGGAGAATAATAAAGGGGCAGGG
AAGTTGTTTGGGAAGGCTGGTGCTGCTGCTCATGGGGACAGTGGAGGCTG
CTAGCAAGGCGGCTGGTGCTGTTAGTGCTGTTAGTGGGGAGCAGATATT
AAGTGCGATTGTTACGGCTGCTGATCGGCTGAGCAGGATGGAAAGAAG
CCTGAGGAGGCTAAAAATCCGATTGCTGCTGCTATTGGGGATAAAGATG
GGGGTGCGGAGTTTGGTCAGGATGAGATGAAGAAGGATGATCAGATTGC
TGCTGCTATTGCTTTGAGGGGGATGGCTAAGGATGGAAAGTTTGCTGTG
AAGGATGGTGAGAAAGAGAAGGCTGAGGGGGCTATTAAGGGAGCTGCTG
AGTCTGCAGTTCGCAAAGTTTTAGGGGCTATTACTGGGCTAATAGGAGA
CGCCGTGAGTTCCGGCTAAGGAAAGTCGGTGATTCAGTGAAGGCTGCT
AGTAAAGAAACACCTCCTGCCTTGAATAAGTAA
```

As used herein, the terms "polynucleotide variant" and "variant" and the like refer to polynucleotides displaying substantial sequence identity with a reference polynucleotide sequence or polynucleotides that hybridize with a reference sequence under stringent conditions. These terms also encompass polynucleotides that are distinguished from a reference polynucleotide by the addition, deletion, substitution, or modification of at least one nucleotide. Accordingly, the terms "polynucleotide variant" and "variant" include polynucleotides in which one or more nucleotides have been added or deleted, or modified, or replaced with different nucleotides. In this regard, it is well understood in the art that certain alterations inclusive of mutations, additions, deletions and substitutions can be made to a reference polynucleotide whereby the altered polynucleotide retains the biological function or activity of the reference polynucleotide.

The phrase "sequence identity" or, for example, comprising a "sequence 50% identical to," as used herein, refer to the extent that sequences are identical on a nucleotide-by-nucleotide over a window of comparison, similar to that of amino acid "identity" discussed herein. Thus, a "percentage of sequence identity" may be calculated by comparing two optimally aligned sequences over the window of comparison, determining the number of positions at which the identical nucleic acid base (e.g., A, T, C, G, I) occurs in both sequences to yield the number of matched positions, dividing the number of matched positions by the total number of positions in the window of comparison (i.e., the window size), and multiplying the result by 100 to yield the percentage of sequence identity. Included are nucleotides and polypeptides comprising at least about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% (or even 100%) sequence identity compared to any of the sequences described herein.

Sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (including but not limited to GAP, BESTFIT, FASTA, and TFASTA) etc.; or the BLAST family of programs as for example disclosed in the GCG (Genetics Computer Group) product, the Wisconsin Package 11.0 (or later when available), a recognized industry standard for sequence analysis of nucleic acids and protein sequences; and Ausubel et al., Current Protocols in Molecular Biology, John Wiley & Sons Inc, 2012.

Further, it will be appreciated by those of ordinary skill in the art that, as a result of the degeneracy of the genetic code, there are many nucleotide sequences that may encode a polypeptide, or fragment of variant thereof, as contemplated herein. Some of these polynucleotides bear minimal homology to the nucleotide sequence of any native gene or chimeric polypeptide. All such sequences are encompassed herein.

The polynucleotides encompassed herein may be present in a "nucleic acid cassette" or "expression cassette". The term "nucleic acid cassette" or "expression cassette" as used herein refers to genetic sequences within a vector which can express an RNA, and subsequently a polypeptide. In one embodiment, the nucleic acid cassette contains at least one gene(s)-of-interest, e.g., a polynucleotide(s)-of-interest that encodes at least one chimera as disclosed herein. In another embodiment, the nucleic acid cassette contains one or more expression control sequences, e.g., a promoter (e.g. constitutive or inducible), enhancer, poly(A) sequence, polyadenylation signals, additional restriction enzyme sites, multiple cloning sites, internal ribosomal entry sites (IRES), recombinase recognition sites (e.g., LoxP, FRT, and Att sites), termination codons, transcriptional termination signals, post-transcription response elements, and polynucleotides encoding self-cleaving polypeptides, epitope tags, and a gene(s)-of-interest, e.g., a polynucleotide(s)-of-interest. The nucleic acid cassette is positionally and sequentially oriented within the vector such that the nucleic acid in the cassette can be transcribed into RNA. Generally, the cassette can be removed and inserted into a plasmid or viral vector as a single unit.

In order to express a desired polypeptide, a nucleotide sequence encoding the polypeptide can be inserted into appropriate vector. (However, a desired polypeptide can also be expressed by delivering an mRNA encoding the polypeptide into a cell.) The term "vector" is used herein to refer to a nucleic acid molecule capable transferring or transporting another nucleic acid molecule. Illustrative examples of vectors include, but are not limited to plasmids, autonomously replicating sequences, phagemids, cosmids, artificial chromosomes such as yeast artificial chromosome (YAC), various episomal vectors, bacterial artificial chromosome (BAC), or P1-derived artificial chromosome (PAC), bacteriophages such as lambda phage or M13 phage, and animal viruses. Exemplary viruses useful as vectors include, without limitation, retrovirus (including lentivirus), adenovirus, adeno-associated virus, herpesvirus (e.g., herpes simplex virus), poxvirus, baculovirus, papillomavirus, and papovavirus (e.g., SV40). Exemplary expression vectors include but are not limited to pCIneo vectors (Promega) for expression in mammalian cells; pLenti4N5-DEST™, pLenti6N5-DEST™, and pLenti6.2/V5-GW/lacZ (Invitrogen) for lentivirus-mediated gene transfer and expression in mammalian cells.

Within a vector, a polynucleotide sequence of interest is generally "operably linked" to other elements of the vector so as the intended function of all elements is possible. In some aspects, the phrase refers to a functional linkage between a nucleic acid expression control sequence (such as a promoter, and/or enhancer) and a second polynucleotide sequence, e.g., a polynucleotide-of-interest, wherein the expression control sequence directs transcription of the nucleic acid corresponding to the second sequence.

Exemplary expression control sequences suitable for use according to the present disclosure include but are not limited to: cytomegalovirus (CMV) immediate early promoter, viral simian virus 40 (SV40) (e.g., early or late), Moloney murine leukemia virus (MoMLV) LTR promoter, Rous sarcoma virus (RSV) LTR, herpes simplex virus (HSV) (thymidine kinase) promoter, H5, P7.5, and P11 promoters from vaccinia virus, short elongation factor 1-alpha (EF1a-short) promoter, long elongation factor 1-alpha (EF1a-long) promoter, early growth response 1 (EGR1), ferritin H (FerH), ferritin L (FerL), Glyceraldehyde 3-phosphate dehydrogenase (GAPDH), eukaryotic translation initiation factor 4A1 (EIF4A1), heat shock 70 kDa protein 5 (HSPA5), heat shock protein 90 kDa beta, member 1 (HSP90B1), heat shock protein 70 kDa (HSP70), β-kinesin (β-KIN), the human ROSA 26 locus (Irions et al., Nature Biotechnology 25, 1477-1482 (2007)), a Ubiquitin C promoter (UBC), a phosphoglycerate kinase-1 (PGK) promoter, a cytomegalovirus enhancer/chicken β-actin (CAG) promoter, a β-actin promoter and a myeloproliferative sarcoma virus enhancer, negative control region deleted, d1587rev primer-binding site substituted (MND) U3 promoter (Haas et al. Journal of Virology. 2003; 77(17): 9439-9450).

The chimeric proteins may be produced by any suitable method, many of which are known to those of skill in the art. For example, they may be chemically synthesized, or produced using recombinant DNA technology (e.g. in bacterial cells, in cell culture (mammalian, yeast or insect cells), in plants or plant cells, or by cell-free prokaryotic or eukaryotic-based expression systems, by other in vitro systems, etc.). In some embodiments, the polypeptides are produced using an *E. coli* recombinant expression system. Thus, the disclosure also encompasses bacterial, mammalian, yeast or insect host cells which comprise at least on copy of a nucleotide sequence encoding a recombinant chimeric protein disclosed herein. In some aspects, the host cell is a bacterial cell. In further aspects, the bacterial cell is an *E. coli* host that has been genetically engineered to contain and express at least one nucleic acid sequence disclosed herein in a manner that results is production of the encoded recombinant chimeric protein.

Methods of making the recombinant chimeric proteins are also included. Generally, the methods include genetically engineering a host cell to contain and express a nucleic acid encoding at least one recombinant chimeric protein disclosed herein. The host cell is genetically engineered so that the at least one recombinant chimeric protein is produced by the host cell, either within the host cell or excreted into medium in which the host cell is grown. Methods of making recombinant proteins using various types of host cells are known in the art, e.g. by growing/cultivating the host cell in a medium compatible with growth, and then i) harvesting and lysing the host cells to release the proteins or, for excreted proteins ii) harvesting the growth medium. Various known steps of concentrating, purifying and analyzing the harvested proteins are followed to achieve a desired level of purity for use in the diagnostics disclosed herein, e.g. filtration, centrifugation, various column purification methods (e.g. affinity chromatography), and the like. Purity levels and identity may be determined, e.g. by gel electrophoresis, HPLC, sequencing, mass spectrometry, and/or any combination of these.

Diagnostic Methods, Assays and Devices

This disclosure provides diagnostics and methods for using the diagnostics to identify individuals who have antibodies to the epitopes contained within the chimeric proteins described herein. In general, a biological sample from an individual (e.g., a human, deer, dog or other mammal susceptible to infection by *Borreliella*) that has been exposed to *Borreliella*, or is suspected of having been exposed to *Borreliella*, or at risk for being exposed to *Borreliella*, is contacted with at least one of the chimeric proteins of the invention. In some aspects, the sample may be contacted with a plurality (e.g., 2 or more) of the chimeric proteins. At least one control protein that is known to not react with antibodies to *Borreliella* proteins is generally included in the assay. The presence or absence of a binding reaction between the chimeric proteins and antibodies in the biological sample (formation of antibody-chimeric protein complexes) is detected. A positive result (i.e., binding occurs and antibody-chimeric protein complexes are detected, thus anti-*Borreliella* antibodies are present) indicates that the individual has been exposed to and/or is infected with *Borreliella*. A negative result (i.e., binding does not occur and antibody-chimeric protein complexes do not form, thus anti-*Borreliella* antibodies are not present) indicates that the individual is not infected with *Borreliella* and has not been previously exposed. For the control proteins, a negative result is expected.

The assays disclosed herein provide both high specificity and sensitivity with respect to detecting anti-*Borreliella* antibodies, as described elsewhere herein.

Accordingly, methods, assays and devices for detecting the presence of anti-*Borreliella* antibodies in a sample are provided. The assays are useful for diagnosing a *Borreliella* infection in a human subject or a non-human mammalian subject. In general, the assays are performed by contacting (mixing, etc.) at least one of the chimeric proteins disclosed herein with a biological sample obtained from a subject who is at risk of having contracted Lyme disease or is suspected of having Lyme disease or is known to have Lyme disease. The test sample is typically blood, plasma, or serum.

The assay used to detect antibodies may be any type of immunoassay, examples of which include but are not limited to: an enzyme-linked immunosorbent assay (ELISA) (e.g., a sandwich ELISA, or a competitive ELISA), a radioimmunoassay, an immunoprecipitation, a fluorescence immunoassay, a chemiluminescent assay, an immunoblot assay, a lateral flow based assays, a flow cytometry assay, a multiplex immunoassay, a mass spectrometry assay, or a particulate-based assay, immunostaining, latex agglutination, indirect hemagglutination assay (IHA) and indirect immunofluorescent assay (FA). Exemplary methods of detecting the binding of an anti-*Borreliella* antibody to an immunoreactive chimeric polypeptide as disclosed herein may include, for example, an ELISA performed in a microplate, a lateral flow test performed using a dipstick or lateral flow device, or a particulate-based suspension array assay, e.g performed using the Bio-Plex® system (Bio-Rad Laboratories, Hercules, Calif., USA). In some aspects, the diagnostic is an immunoblot, an enzyme-linked immunosorbent assay (ELISA) or a lateral flow assay, all three of which were used in the Examples described herein. Generally, immunoblots and ELISAs are conducted in a laboratory setting, such as in a commercial or research diagnostic lab, whereas lateral flow assays can be conducted rapidly e.g., at the point of care, such as in a physician's or veterinarian's office. However, the diagnostic aspects of the disclosure are not confined to clinical use or home use, but may also be valuable for use in the laboratory as a research tool, e.g. to identify Lyme disease spirochetes isolated from ticks, screen for the presence of antibodies in sentinel animals such as wildlife, to investigate the geographical distribution of *Borreliella* species and strains, etc. The diagnostic tools detailed here can also be used for epidemiological analyses.

ELISA

In certain embodiments, the detection of a chimera-antibody complex described herein is accomplished using an enzyme-linked immunosorbent assay (ELISA). This assay may be performed by first contacting a chimeric polypeptide that has been immobilized on a solid support, commonly the well of a microtiter plate, with a sample, such that antibodies specific for the chimeric polypeptide within the sample are allowed to bind to the immobilized chimeric polypeptide. Unbound sample is then removed from the immobilized chimeric polypeptide and a detection reagent capable of binding to the immobilized antibody-chimeric polypeptide complex is added. Typically, the reagent is capable of detecting IgG and IgG that have bound to the diagnostic antigen. The amount of detection reagent that remains bound to the solid support is then determined using a method appropriate for the specific detection reagent.

In some embodiments, the detection reagent contains a binding agent (such as, for example, Protein A, Protein G, immunoglobulin, lectin or free antigen) conjugated or covalently attached to a reporter group or label. Exemplary reporter groups or labels include enzymes (such as horseradish peroxidase), substrates, cofactors, inhibitors, dyes, radionuclides, luminescent groups, fluorescent groups and biotin. The conjugation of binding agent to reporter group or label may be achieved using standard methods known to those of ordinary skill in the art. Common binding agents may also be purchased conjugated to a variety of reporter groups from many commercial sources (e.g., Zymed Laboratories, San Francisco, Calif.; and Pierce, Rockford, Ill.).

In an aspect of the present disclosure, the presence or absence of *Borreliella* specific antibodies may be determined in the sample by comparing the level of a signal detected from a reporter group or label in the sample with the level of a signal that corresponds to a control sample or predetermined cut-off value. In certain embodiments, the cut-off value may be the average mean signal obtained when the immobilized *Borreliella* immunoreactive chimera is incubated with samples from an uninfected subject. The cut-off value may be determined using a statistical method or computer program.

In related aspects, an ELISA assay as described above may be performed in a rapid flow-through, lateral flow, or strip test format, wherein the antigen is immobilized on a membrane, such as a nitrocellulose membrane. In this flow-through test, *Borreliella* antibodies within the sample bind to the immobilized *Borreliella* immunoreactive chimera as the sample passes through the membrane. A detection reagent, such as protein A labeled with gold, a fluorophore, or a chromophore, binds to the chimera-antibody complex as the solution containing the detection reagent flows through the membrane. Chimera-antibody complexes bound to the detection reagent may then be detected, as appropriate for the detection reagent used (e.g., based on the presence or absence of a visibly detectable color or fluorescent label, a nanoparticle, a luminescent rare earth nanoparticle, a luminous nanoparticle, a strontium aluminate nanoparticle (e.g., see Paterson et al., 2014; and Wang et al., 2017, etc.).

In an aspect, a flow-through format ELISA may be performed in which one end of the membrane to which a *Borreliella* immunoreactive chimera is immobilized may be immersed in a solution containing the sample, or the sample may be added to an area (i.e., a sample zone) at one end of the membrane. The sample migrates along the membrane through a region (i.e., a labeling zone) comprising the detection reagent, and flows to the area (i.e., a binding zone) comprising the immobilized *Borreliella* immunoreactive chimera. An accumulation of detection reagent at the binding zone indicates the presence of *Borreliella* specific antibodies in the sample.

Typically, a flow-through ELISA may feature a detection reagent applied to a test strip in a pattern, such as a line, that can be read visually. As with other lateral flow tests, the absence of such a pattern typically indicates a negative result. It is within the ability of an ordinarily skilled artisan to select an amount of the *Borreliella* immunoreactive chimeric polypeptide for immobilization on the membrane that can generate a visually discernible pattern when the biological sample contains a level of antibodies that would be sufficient to generate a positive signal in a standard format ELISA. Preferably, the amount of chimeric polypeptide immobilized on the membrane ranges from about 25 ng to about 1 mg.

Particulate-Based Assays

In general, particle-based assays use a capture-binding partner, such as an antibody or an antigen in the case of an immunoassay, coated on the surface of particles, such as microbeads, crystals, chips, or nanoparticles. Particle-based assays may be effectively multiplexed or modified to assay numerous variables of interest by incorporating fluorescently labeled particles or particles of different sizes in a single assay, each coated or conjugated to one or more labeled capture-binding partners. The use of sensitive detection and amplification technologies with particle-based assay platforms known in the art has resulted in numerous flexible and sensitive assay systems to choose from in performing a method described herein. For example, a multiplex particle-based assay such as the suspension array Bio-Plex® assay system available from Bio-Rad Laboratories, Inc. (Hercules, Calif.) and Luminex, Inc. (Austin, Tex.) may be useful in identifying *Borreliella* antibodies in a sample.

In an aspect, the present disclosure contemplates the immobilization of an isolated *Borreliella* immunoreactive chimeric polypeptide on a surface of a particle for use in a particle-based immunoassay. As described herein, methods of peptide immobilization onto support surfaces are well-known in the art. In a preferred aspect, a labeled *Borreliella* immunoreactive chimeric polypeptide disclosed herein is immobilized onto a surface of a particle and the polypeptide-particle complex is employed in an ELISA or in a flow cytometry assay according to established protocols.

Lateral Flow Assay

Lateral flow tests may also be referred to as immunochromatographic strip (ICS) tests or simply strip-tests. In general, a lateral flow test is a form of assay in which the test sample flows laterally along a solid substrate via capillary action, or alternatively, under fluidic control. Such tests are often inexpensive, require a very small amount (e.g., one drop) of sample, and can typically be performed reproducibly with minimal training. The economical simplicity and robustness of many lateral flow assay formats makes these types of tests ideal for identifying a *Borreliella* infection at the point of care, which can be particularly important when the subject is, for example, a human or pet exhibiting detectable antibodies during a treatable phase of infection.

Exemplary lateral flow device formats include, but are not limited to, a dipstick, a card, a chip, a microslide, and a cassette, and it is widely demonstrated in the art that the choice of format is largely dependent upon the features of a particular assay. Lateral flow devices are now ubiquitous in human and veterinarian medicine and quite varied, providing many options to the ordinarily skilled artisan for detecting a polypeptide-antibody complex in a sample. (See any of U.S. Pat. Nos. 7,344,893, 7,371,582, 6,136,610, and U.S. Patent Applications, 2005/0250141 and 2005/0047972, or Koczula et al. (2016) each incorporated herein by reference in entirety.) By way of a nonlimiting example, a sample from a subject suspected of having an *Borreliella* infection is applied to a lateral flow device comprising at least a sample zone and a binding zone. The sample may be a serum sample and may be drawn laterally from the sample zone to the binding zone which comprises an *Borreliella* immunoreactive chimeric polypeptide disclosed herein immobilized to a surface of the lateral flow device. In this example, the binding of the immobilized *Borreliella* immunoreactive chimeric polypeptide on the lateral flow device is an indication that *Borreliella*-specific antibodies are present in the sample from the subject, indicating a *Borreliella* infection in the subject.

Figure 13:
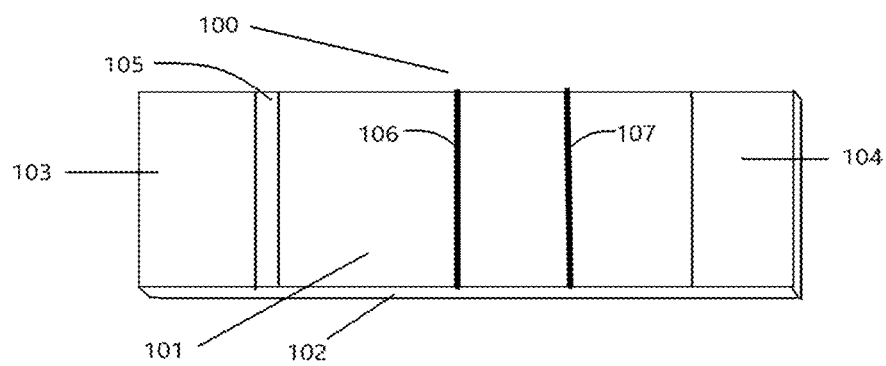
FIG. 13. Schematic representation of a lateral flow device. Shown are test line 106 which comprises immobilized capture molecules (e.g., antibodies specific for binding to complexes that comprise anti-*Borreliella* antibodies bound to chimeric proteins), control line 107 which lacks capture molecules and sample application pad 103, which receives a sample to be tested. Other features are discussed elsewhere herein.

Accordingly, the chimeric proteins as described herein may be used in a device for detecting anti-*Borreliella* antibodies, i.e., antibodies raised against one or more *Borreliella* proteins upon and/or after and/or during infection of a subject with Lyme disease spirochetes. The devices can be used to detect *Borreliella* infections such as Lyme disease. FIG. 13 shows an example of a lateral flow device. Lateral flow device 100 comprises a membrane substrate 101 supported on backing 102, which may be a solid backing. Generally, membrane substrate 101 comprises, for example, a woven mesh, a cellulose fiber, glass fiber, mixed glass and cellulose fiber, synthetic fiber, mixed fiber, surface modified plastic (polyester, polypropylene, or polyethylene), graded density polyethersulfone (PES), nitrocellulose, or combinations thereof. The membrane substrate can be of any suitable form, e.g., a strip, circle, etc. The solid backing may comprise any suitable material including, but not limited to, plastic, fiber, and glass. In some instances, the backing comprises an adhesive. Lateral flow device 100 generally further comprise a sample application pad 103 to receive a sample and absorbent pad 104 (e.g., a cellulose filter) to prevent backflow and conjugate release pad 105 which contains e.g., chimeric proteins that are specific to the antibodies to be detected. In some aspects, the chimeric proteins are conjugated to detectable particles, such as colored or fluorescent particles, e.g. colloidal gold or latex microspheres.

In most aspects, membrane substrate 101 further comprises at least one test line 106 and at least one control line 107. Test line 106 comprises immobilized capture molecules (e.g. antibodies) specific for binding to complexes that comprise anti-*Borreliella* antibodies bound to chimeric proteins. Control line 107 lacks capture molecules. In some aspects, test line 106 is placed upstream of at least one control line 107. In other aspects, test line 106 is placed downstream of at least one control line 107.

To use the device, a suitable quantity of sample is applied to sample application pad 103. The sample then travels by capillary action across conjugate release pad 105 in the direction of the test lines. If antibodies are present in the sample, they encounter and bind to chimeric proteins in conjugate release pad 105, forming antibody-antigen complexes or conjugates. The complexes or conjugates continue to migrate along the device and reach test line 106 where they are captured and immobilized on the test line. Detection of binding at test line 109 indicates that antibodies are present in the sample. If no binding is detected at test line 109, this indicates that antibodies are not present in the sample.

The binding is rendered detectable by any of a variety of methods, e.g., by a chemical reaction that causes a color change at the test line but not at the control line, or by the chimeras having been tagged with a detectable marker, etc. In some aspects, the change may be detectable with the naked eye. In other aspects, results from the device are transferred e.g., wirelessly or through a cable, to a computerized device to process and display information about the change. In some aspects, the result is transmitted to a software program on a computerized device, where the computerized device has a graphical user interface that displays the assay results. In some instances, the results are transferred to a database. In some instances, the results from the database are used e.g., for bioinformatics applications.

Generally, the lateral flow device comprises a buffer which may be referred to as a running or chase buffer. In some aspects, the buffer is a physiologically compatible buffer or carrier (e.g. a phosphate-buffered saline buffer, citrate buffer, a Good's buffer, etc.) and may further comprise, e.g. a blocking agent (e.g., casein, Tween® reagent, etc.), a surfactant, various additives, and other reagents to increase sensitivity of the assay. In some instances, the buffer is or comprises a phosphate-based buffer with a divalent cation.

In some aspects, lateral flow device 100 further comprises a housing (not shown) that covers at least a portion of the device. The housing may comprise, for example, a sample application port to allow sample application and an optic opening to allow signal visualization. The housing can comprise any suitable material. For example, the housing can comprise a plastic material. In some instances, the housing comprises an opaque, translucent, or transparent material.

Other examples of lateral flow devices and features thereof are found in published US patent applications 20220196560, 20220221452, 20220178943 and 20220176371, the complete contents of each of which is hereby incorporated by reference in entirety.

Generally, a small volume of sample is required to utilize the devices described herein e.g., an volume of from about 1 µL to about 1000 µL, such as from about 5 µL to about 500 µL, or about 10 µL to about 100 µL. In some aspects, about 10, 20, 30, 40, 50, 60, 70, 80 90 or 100 µL of sample is applied to the device.

Use of the Devices

In some aspects, the disclosure provides a method to detect the presence of antibodies to at least one of *Borreliella* proteins DbpA, DbpB, BBK19, BBK73, BBA53, VlsE and BB0238, or to detect antibodies which react with *Borreliella* proteins having epitopes in common with or epitopes similar enough to those of DbpA, DbpB, BBK19, BBK73, BBA53, VlsE and BB0238 so as to bind to the chimeras.

Devices and systems comprising the devices as described herein can detect *Borreliella* antibodies in a rapid and reliable manner. In some instances, the device provides a read out in about 1 minute to about 30 minutes (min). In some aspects, a read out is provided in about 20 minutes.

Methods as described herein have a sensitivity of at least about 70% of detecting anti-*Borreliella* antibodies. In some instances, the methods and systems as described herein are at least about 75%, 80%, 85%, 90%, 95% or more than 95% sensitive in detecting anti-*Borreliella* antibodies. Using an ELISA format the sensitivity can be even greater than 95%, such as about 96, 97, 98 or 99%. Methods as described herein may have a specificity of at least about 90% for detecting anti-*Borreliella* antibodies e.g. as compared to other antibodies. In some instances, the methods and systems as described herein are at least about 90%, 91, 92, 93, 94, 95% or more than 95% specific (such as about 96, 97, 98 or 99%) for detecting anti-*Borreliella* antibodies. Methods and systems as described herein may have an accuracy of at least about 70% of detecting anti-*Borreliella* antibodies. In some instances, the methods and systems as described herein are at least about 75%, 80%, 85%, 90%, 95% or more than 95% accuracy in detecting anti-*Borreliella* antibodies. In some aspects, no false positives occur. Methods and systems as described herein may have a reliability of at least about 70% of detecting anti-*Borreliella* antibodies. In some instances, the methods and systems as described herein are at least about 75%, 80%, 85%, 90%, 95% or more than 95% reliable in detecting the anti-*Borreliella* antibodies Samples that are analyzed as described herein may be from any mammal that is susceptible to infection by *Borreliella*. Examples include but are not limited to humans, companion animals (dogs, cats), food sources, livestock (cattle, horses, oxen, sheep, pigs, goats) wild-life and zoo animals (mice, deer, rats, raccoons, opossum, coyotes, bears, vultures, gophers, groundhogs, squirrels, etc.).

The present disclosure also encompasses methods which include 1) diagnosing the infection in a subject as described herein and then ii) treating the subject who is diagnosed or identified as having *Borreliella* antibodies by administering a suitable treatment. Subjects diagnosed as having a *Borreliella* infection (which may be Lyme disease) are typically treated with antibiotics. For example, in dogs treatment usually involves a course of antibiotics which will last for 4 weeks or longer. The antibiotic doxycycline is typically a first-choice option. In humans, for early Lyme disease, a short course of oral antibiotics, such as doxycycline or amoxicillin, is generally used. In more complicated cases, Lyme disease is usually treated with three to four weeks of antibiotic therapy. Oral antibiotics are the standard treatment for early-stage Lyme disease. These usually include doxycycline for adults and children older than 8, or amoxicillin or cefuroxime for adults, younger children, and pregnant or breast-feeding women. A 14- to 21-day course of antibiotics is usually recommended, but some studies suggest that courses lasting 10 to 14 days are equally effective. Intravenous antibiotics may be administered if the disease involves the central nervous system, e.g., typically for 14 to 28 days. Intravenous antibiotics can cause various side effects, including a lower white blood cell count, mild to severe diarrhea, or colonization or infection with other antibiotic-resistant organisms unrelated to Lyme, and other treatment measures may be used to prevent, combat or control such side effects.

Kits

Devices as described herein, especially lateral flow devices, may be included in a kit. In some instances, kits are provided to an administering physician, veterinarian, other health care professional, a patient, or a caregiver. In some instances, a kit comprises a container which contains a testing device and instructions for using the device. In some instances, the container contains more than one testing device. Generally, the testing devices are individually wrapped.

Such a kit may comprise chimeric polypeptides immobilized to one or more separate lateral flow assay devices, such as a nitrocellulose test strips. In these embodiments, each of the test strips may further comprise a detection reagent. Such a kit may further comprise one or more containers for sample material, one or more diluents for sample dilution, and one or more control indicator strips for comparison.

The assay kit can also include an amount of a chase buffer, e.g., PBS, sufficient to enable proper flow of the tracer reagent on each of the first and second test lines to the control line. The kit may comprise solutions, agents, and chase buffers that may be required to operate the device.

In some aspects, reagents and/or components comprising a kit are provided in a lyophilized form (lyophilisate) or as a dry powder. The lyophilisate or powder can be reconstituted by the addition of a suitable solvent. In particular embodiments, the solvent may be a sterile, pharmaceutically acceptable buffer and/or other diluent. It is envisioned that such a solvent may also be provided as part of a kit.

When the components of a kit are provided in one and/or more liquid solutions, the liquid solution may be, by way of non-limiting example, a sterile, aqueous solution.

Additional kit components can include, e.g., an instrument for sample collection, e.g., a sharp instrument for drawing blood, or a swab for collecting mucosal swabs and an instrument for applying the sample to the sample pad, e.g., a dropper.

The kit can optionally also contain one or more other testing devices and diagnostic tools. The kit may also optionally contain therapeutic or other agents. In some cases, the kit comprises an assisted vision tool to help visually observe the readout such as a light source, a light filter, or a magnifier.

The assay kit can further include instructions for use, which can comprise a description of test pattern interpretation, and recommendations for action based on the result obtained. In some embodiments, the instructions for use include a cautionary warning based on the result interpretation. In embodiments, a mobile phone application is made available to the user, so that test results is provided to a practitioner and/or epidemiologist.

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

EXAMPLES

Bacterial Cultivation.

*Borreliella* isolates were cultivated in standard BSK-II media supplemented with 6% rabbit serum at 34° C. (without gelatin). Growth was monitored using wet-mounts and dark-field microscopy. Cells were harvested from late-log phase cultures by low speed centrifugation.

Preparation of Recombinant *Borreliella* Proteins.

Sixty genes from *B. burgdorferi* strain B31 were selected for analysis. The gene sequences were codon-optimized for expression in *Escherichia coli*, synthesized (minus the leader sequence) on a fee for service basis, and inserted into the vector pET45b(+) at its BamHI and EagI restriction sites (GenScript). The sequences of the cloned DNA were confirmed by DNA sequence analyses on a fee for service basis. The plasmids were purified and transformed into *E. coli* BL21(DE3) cells. Protein expression was induced by auto-induction or by the addition of IPTG (1 mM) and the cells were lysed using a high-pressure homogenizer. The His-tagged proteins were purified using nickel affinity chromatography on an ÄKTA™ FPLC platform (Cytvia) or through the use of Ni affinity gravity flow columns (FIG. 1). Some proteins were subjected to a second round of FPLC purification using a cobalt column on the ÄKTA platform. As detailed below, the chimeric diagnostic antigens that were designed based on the data detailed within were produced and purified in the same manner. FIG. 1 presents an SDS-PAGE gel that demonstrates the purity of representative recombinant proteins.

SDS-PAGE, Immunoblot and Dot-Blot Analyses.

Cells were recovered by centrifugation, washed with phosphate buffered saline (PBS) and cell lysates generated by sonication. The cell lysates and recombinant proteins were fractionated by SDS-PAGE using precast AnykD™ Criterion™ Gels purchased from Biorad. Equal loading of proteins and cell lysates was confirmed by staining representative gels with Coomassie Brilliant Blue. The proteins were transferred to PVDF membranes for immunoblot analyses. Horseradish peroxidase (HRP)-conjugated anti-rat IgG was used at a 1:40,000 dilution. Antibody binding was detected using Clarity™ Western ECL substrate and chemiluminescence. Images were captured using a Biorad Chemi-Doc™ imaging System. For dot-blot analyses, recombinant proteins (125 ng) were spotted onto 0.2 µm nitrocellulose membranes, and probed with sera and IgG binding detected as above. Protein loading on the dot-blots was assessed by staining with MemCode™ stain.

ELISA analyses. ELISA plate wells were coated with 500 ng of protein (individual recombinant proteins or chimeric recombinant proteins) in bicarbonate buffer overnight at 4°

C. Antisera were used at dilutions indicated in the figures with secondary Antibodies used at a 1:15000 dilution. ABTS (chromogenic substrate) was added, the plates were incubated for 20 min and the absorbance was measured at 405 nm. Preimmune serum served as a negative control serum sample and BSA or the FhbB protein served as the immobilized negative control for non-specific antibody binding.

Results

Detection of Antibodies in the Serum of Infected Mammals

Serum samples from *B. burgdorferi* infected humans, client-owned dogs, horses, laboratory mice, and wildlife have been collected and catalogued over the past decade. Human serum samples were obtained from the CDC, NIH, and the Lyme disease Biobank. Serum samples from wildlife (eastern coyotes, red foxes, gray foxes, eastern black bears, pocket gophers, ground hogs, black vultures and squirrels were obtained from the USDA, Pennsylvania Game Commission, Pennsylvania State University and others). The samples from client-owned dogs were tested for antibodies to the panel of recombinant proteins (Tables 1 and 2).

TABLE 1

Identification of Lyme disease spirochete proteins that are antigenic during infection in canines. Serum from client-owned dogs (naturally infected; i.e., bitten by an Ixodes tick) was screened by ELISA using the representative proteins indicated above. The results demonstrate that no single protein is sufficient for diagnosis. We concluded that an effective diagnostic antigen must contain segments of multiple antigens.

| Protein designations | # Ab (+) Samples (%) |
| --- | --- |
| BBA24 (DbpA) | 83/94 (88) |
| BBA25 (DbpB) | 84/94 (89) |
| BBA36 | 76/94 (81) |
| BBK53 | 51/94 (54) |
| BBA04 | 21/77 (27) |
| BBR42 (OspF) | 11/44 (25) |
| BBM38 (OspF) | 17/44 (39) |
| BBO39 (OspF) | 17/44 (39) |
| OspB | 11/45 (24) |
| BBA73 | 79/94 (84) |
| BBA74 | 55/94 (59) |
| BBB07 | 6/45 (13) |
| BB0238 | 56/94 (60) |

TABLE 2

Demonstration that a multi-protein (chimeric) approach is required to verify infection. Serum from 7 dogs (canine 3 = negative control) was screened for antibodies to several proteins. Proteins that were immunoreactive with a given serum sample are indicated by +. No single protein detected antibodies to the Lyme disease spirochetes in all confirmed samples further demonstrating the necessity of a multi-protein or chimeric approach to diagnosis.

| | BBA73 | BB0238 | BBA24 | BBA25 | BBA36 | BBB14 | BBK53 |
| --- | --- | --- | --- | --- | --- | --- | --- |
| Dog1 | + | − | − | − | − | − | − |
| Dog2 | + | + | + | + | + | − | + |
| Dog3 | − | − | − | − | − | − | − |
| Dog4 | + | − | − | − | − | − | − |
| Dog5 | + | + | + | + | + | + | + |
| Dog6 | + | − | − | + | − | − | − |
| Dog7 | + | − | + | − | + | − | − |

Figure 2A:
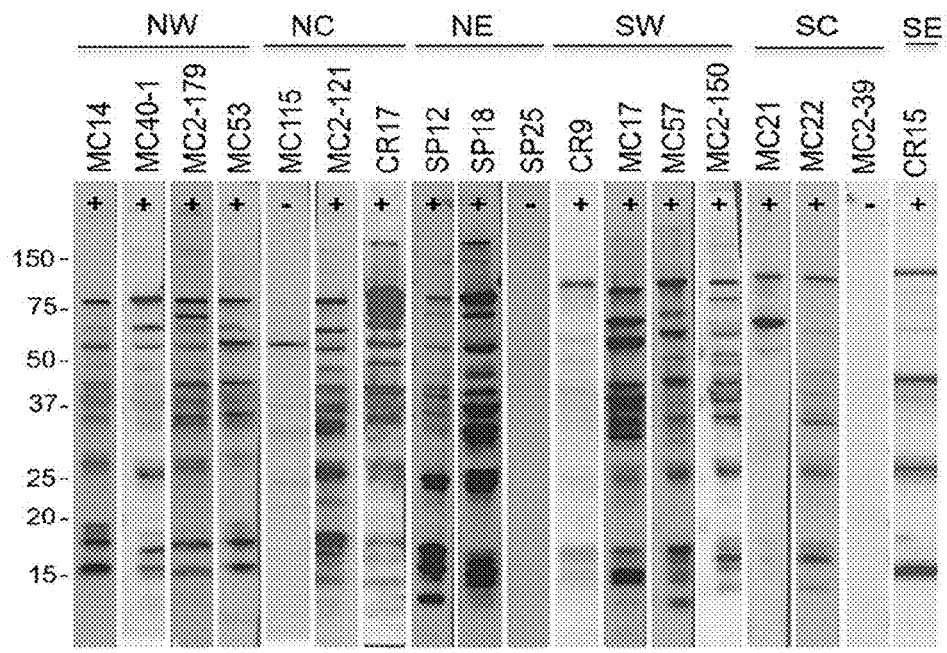
FIGS. 2A and B. Analysis of antibody responses to Lyme disease spirochete proteins in wildlife (*Canis latrans*; Eastern coyotes). In A, *B. burgdorferi* cell lysates were immunoblotted and screened with serum collected from Lyme disease-infected eastern coyotes from the commonwealth of Pennsylvania. The results demonstrated that the antibody responses that develop vary among individual animals (as evidenced by the immunoreactive protein profiles). In B, the coyote sera were used to screen recombinant proteins using a dot-blot format. As can be seen, no single protein was sufficient to confirm infection in all animals. The labels above each panel indicate the geographic sector of Pennsylvania from which the animals and serum samples were collected, Abbreviations are as follows: NW, northwest; NC, north central; NE, northeast; SW, southwest; SC, southcentral, southeast.
Figures 2B, 3A:
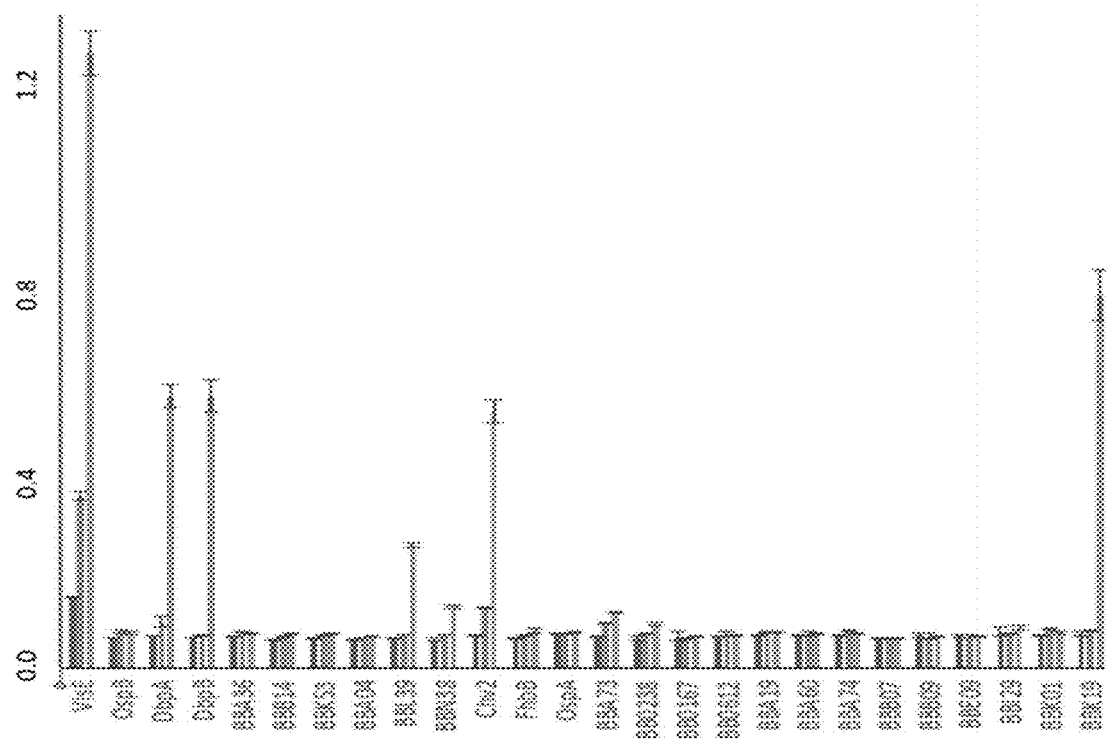
FIGS. 3A and B. Identification of *B. burgdorferi* proteins that elicit antibodies by day 12 of infection in mice. A, first set of 30 proteins; B, second set of 30 proteins. Mice were infected and serum recovered from each on days 7, 8, and 12 (left to right in each data set). The proteins listed on the x-axis were screened with the serum samples by ELISA.

While some proteins detected antibodies in a majority of serum samples tested, these analyses demonstrated that no single protein is sufficient for detecting antibodies in all serum samples from animals infected with the Lyme disease spirochetes. As noted above, this finding was validated by screening serum from other mammals including wildlife and humans. FIG. 2 presents screening results obtained when serum from Eastern coyotes were screened against *B. burgdorferi* whole cell lysates or individual recombinant proteins. As can again be seen, no single protein was sufficient for detecting antibodies in all serum samples. The results were further confirmed by screening serum collected from squirrels, red foxes, grey foxes, gophers and groundhogs.

Infection of Mice with *B. burgdorferi* and Temporal Analysis of Antibody Responses to Specific Recombinant Antigens.

Figure 3B:
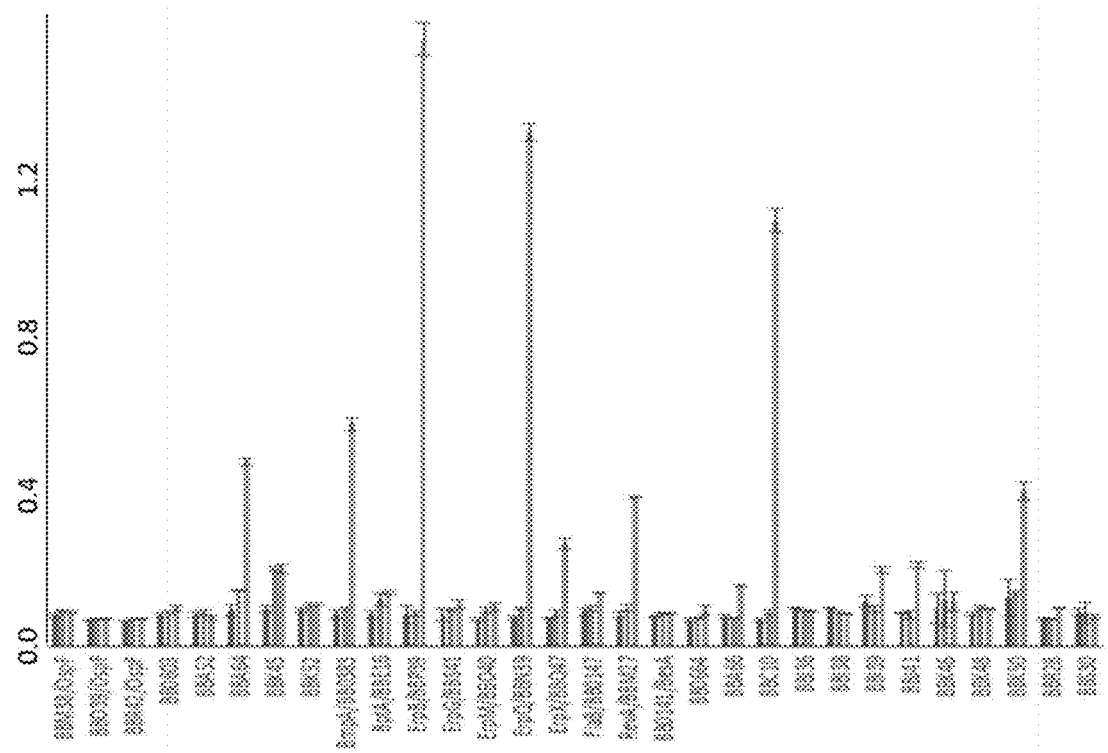

Mice were infected by needle inoculation (subcutaneous) with $10^4$ live *B. burgdorferi* cells. The spirochetes were administered subcutaneously between the shoulder blades. Serum was harvested from groups of 5 mice on days 0, 7, 8 and 12. The sera were screened against several recombinant proteins (FIG. 3) using an ELISA format. Representative data are shown. Select proteins were effective at detecting IgG antibodies as early as day 12 of infection (bottom bar). Proteins that detected specific IgG responses included VlsE, DbpA, DbpB, BBK19, BBA64, BB0383, BBP39, BBN38, BBM27, BBC10, and BBK50. These proteins were selected as candidates for inclusion in chimeric diagnostic antigens as detailed below.

Infection of Dogs with *B. burgdorferi* and Temporal Analysis of Antibody Responses to Specific Recombinant Antigens.

Figure 4:
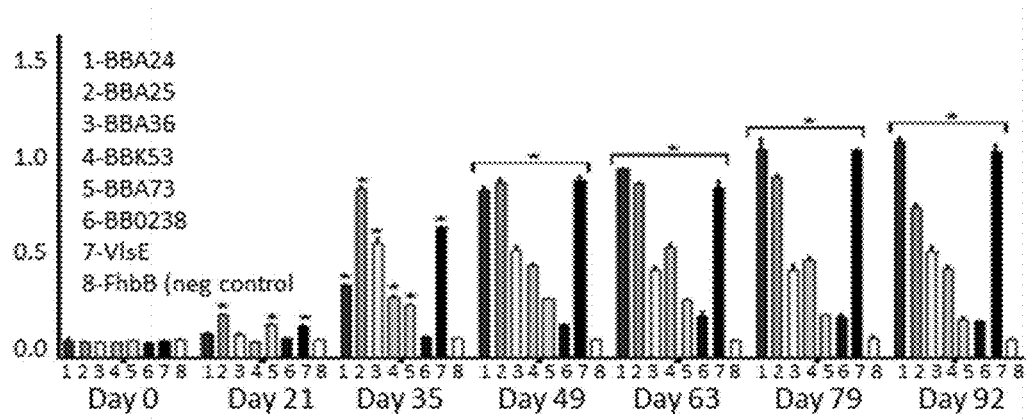
FIG. 4. Identification of proteins that can detect antibodies to Lyme disease spirochetes during early infection. Recombinant proteins (as indicated in the key) were screened by ELISA with serum collected over time from experimentally infected dogs. Approximately 60 different proteins were screened (representative data are shown).

To assess antibody responses to specific recombinant proteins over time, purpose bred dogs were infected experimentally infected using field collected ticks obtained from the northeastern US. Blood samples were collected 0, 21, 35, 63, 79 and 92 days later. Serum was harvested and screened for antibodies to several different Lyme disease spirochete proteins. The recombinant proteins DbpA, DbpB, BBA36, BBK53, BBA73, BB0238, VlsE and FhbB 35405 (negative control) were immobilized in the wells of ELISA plates and screened with the serum. The results are presented in FIG. 4. As can be seen, several proteins readily detected antibodies during early infection starting at day 35. The data presented above demonstrate that antibodies in mice can be detected as early as 12 days after infection whereas in dogs antibodies were detected after 35 days. This is due in part to differences in the inoculum dose (relative to body mass) and the general differences in the immune response in mice versus dogs.

Identification of the Immunodominant Domains of Lyme Disease Spirochete Proteins.

Figure 5:
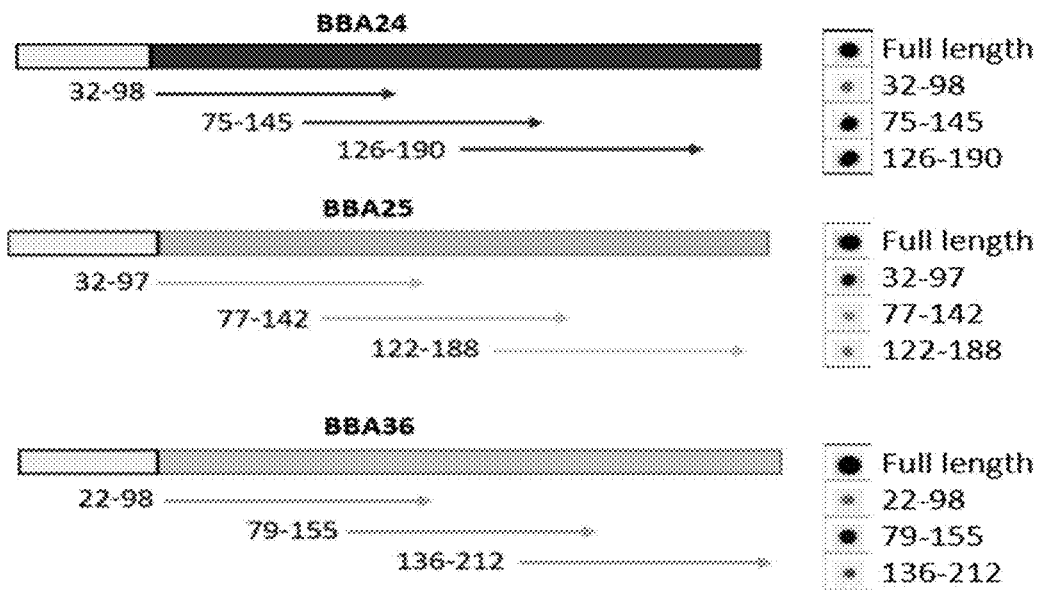
FIG. 5. Identification of the immunodominant region of candidate diagnostic antigens. Data for three representative proteins are shown (BBA24, BBA25, and BBA36). Full-length proteins (minus the leader peptide) and subfragments of each protein (indicated in the schematic), were synthesized, produced, and purified. The proteins were dot-blotted onto nitrocellulose membranes (images on the right) and screened with serum from infected animals. The immunodominant regions of BBA24, BBA25, and BBA36 mapped within residues 75-190, 32-97, and 79-155, respectively. The same mapping strategy was applied to several other proteins. These analyses were central in informing the choice of antigens and specific protein fragments to use in the generation of chimeric diagnostic antigens.

Identification of the immunodominant domains of an antigen is a key step forward in developing chimeric diagnostic proteins. Full length proteins (minus the leader and/or lipidation motifs) and overlapping fragments of each protein were synthesized, cloned, expressed in *E. coli* and purified using FPLC. The fragments were tested for their ability to bind protein specific antibody by multiple independent approaches (dot blot and ELISA). FIG. 5 presents a schematic of the general strategy used to map epitope containing domains using three different proteins as examples (BBA24, BBA25 and BBA36). The proteins were dot-blotted onto nitrocellulose membranes and screened with serum from infected animals. The immunodominant regions of BBA24, BBA25 and BBA36 mapped within residues 75-190, 32-97, and 79-155, respectively. The same mapping strategy was applied to several other proteins including but not limited to BBK19, BBA73, BB0238, BBK53, OspC, VlsE and BBG01. These analyses were central in informing the choice of antigens and specific protein fragments to use in the generation of chimeric diagnostic antigens.

Construction of Chimeric Diagnostic Antigens.

Figure 6:
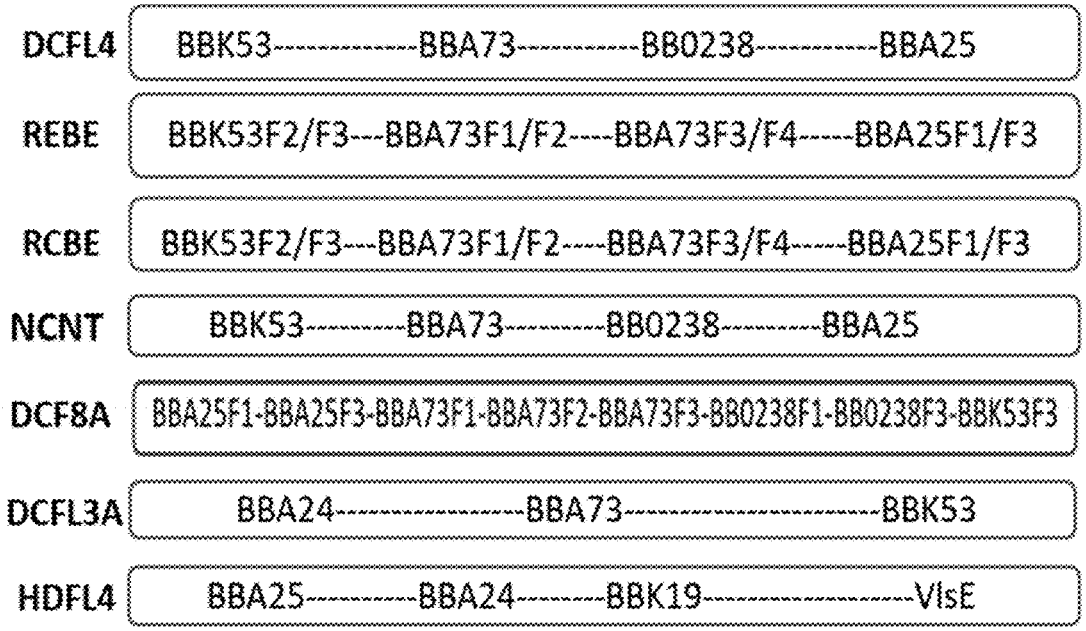
FIG. 6. Schematic depiction of representative chimeric diagnostic antigens. The identity of each chimeric is indicated to the left and the proteins, or protein segments, that comprise each are indicated above or within each schematic. The varying segments of the N and C terminal domains of the proteins that comprise REBE and RCBE have been deleted in these constructs, as detailed in the sequences. The schematics are not drawn to scale.

Based on the immunological studies and epitope mapping analyses detailed above, a series or chimeric diagnostic antigens were designed, modified by codon optimization and by insertion of Trp residues (for easy detection), cloned into pET45 expression vector, autoinduced and purified by FPLC. FIG. 6 presents schematic representations of a subset of the proteins that were generated. All were successfully purified to homogeneity. Initial immunological screening of the chimerics using immunoblots, dot blots or ELISAs revealed that DCFL4, DCFL3A and HDFL4 were leading candidates as they demonstrated higher sensitivity than REBE, RCBE, NCNT and DCF8A. Table 3 summarizes some of the results obtained with DCFL4. The protein was immobilized in ELISA wells and then screened with the serum samples indicated in Table 3. Sera from "specific pathogen free dogs", dogs infected with *Leptospira* and dogs infected with *Anaplasma* served as controls to measure specificity. Sensitivity was assessed using serum obtained from dogs that were naturally or experimentally infected. DCFL4 demonstrated high specificity.

TABLE 3

Summary of ELISA results obtained using DCFL4 as the detection antigen. Serum from the study groups indicated above were screened for antibodies to the Lyme disease spirochetes using DCFL4 as the detection antigen. DCFL4 proved to be highly specific with high sensitivity.

| Serum description | #+/#total | % Ab + |
|---|---|---|
| Specific pathogen free dog | 1/50 | 2.0 |
| Leptospira Ab + | 2/27 | 7.4 |
| Anaplasma Ab + | 0/40 | 0.0 |
| Lyme Ab + (Experimentally Infected) | 60/60 | 100.0 |
| Lyme Ab + (Naturally infected client-owned dogs) | 51/58 | 87.9 |

Figure 7:
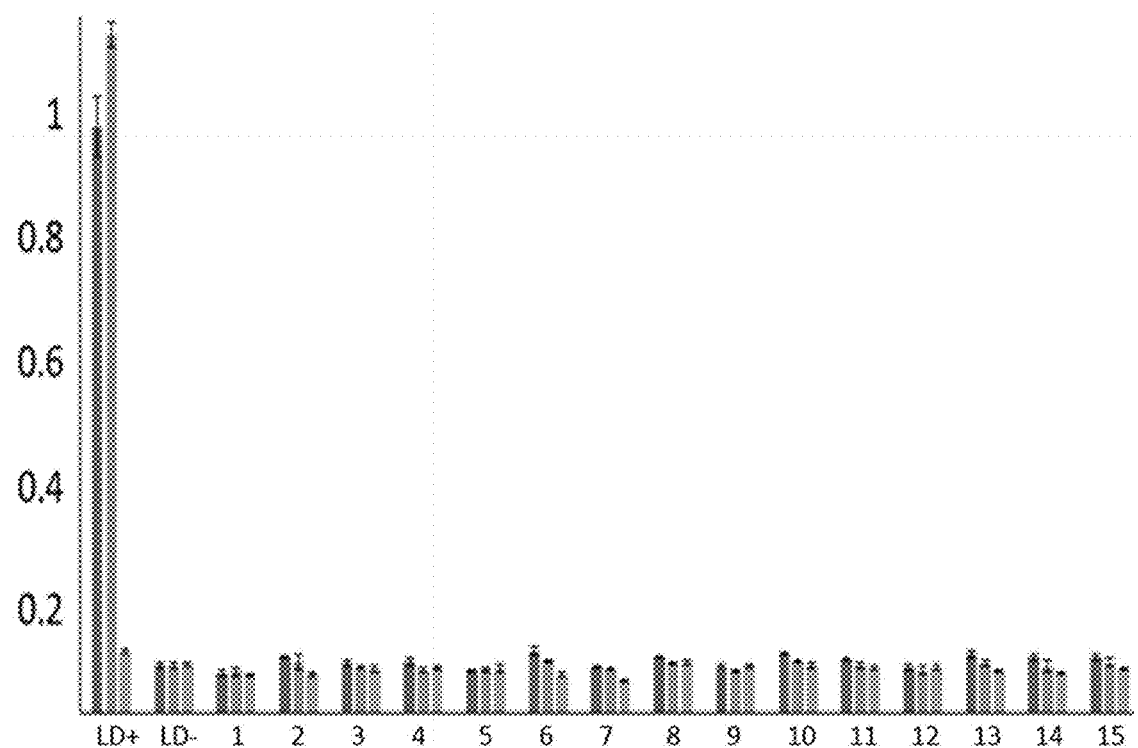
FIG. 7. DCFL4 does not yield false positives with sera from dogs infected with other pathogens. Recombinant DCFL4, VlsE and FhbB (left, middle and right bars in each data set) were immobilized in ELISA plate wells and screened with serum from dogs verified to be infected with *Leptospira* (1-5), *Anaplasma* (6-10), or *Ehrlichia* (11-15). Positive controls included serum from dogs infected with Lyme disease (LD+) and infection-free dogs (LD−).

Specificity of DCFL4 was further verified using additional serum samples derived from dogs infected with *Leptospira*, *Anaplasma* and *Ehrlichia* (FIG. 7). The results demonstrate the effectiveness of DCFL4 to serve as a diagnostic antigen.

Figure 8:
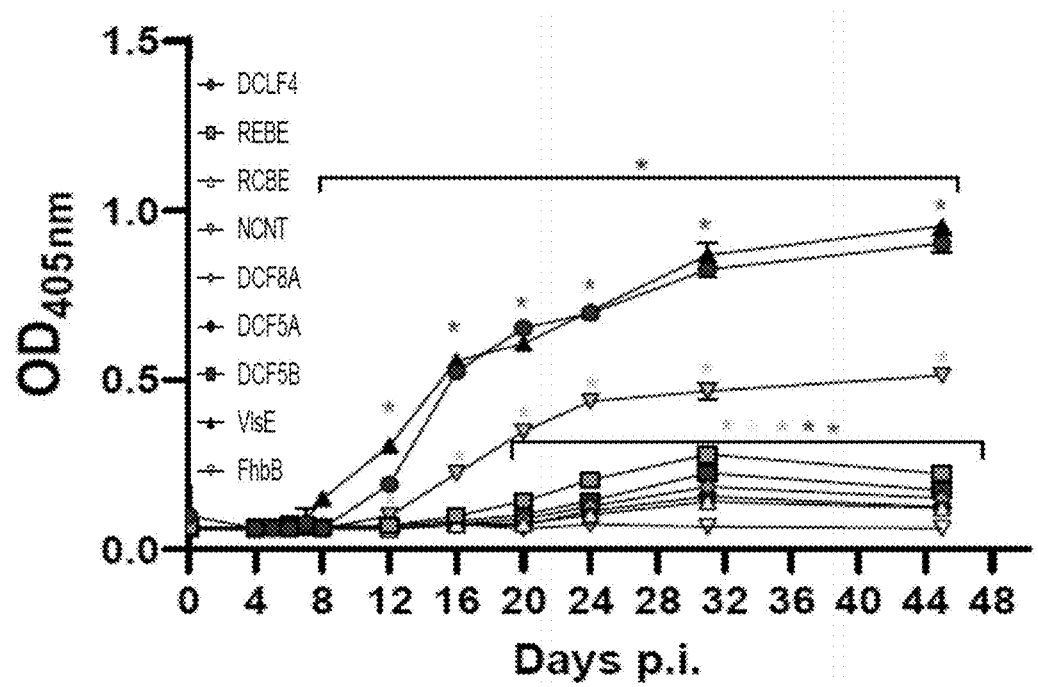
FIG. 8. Analysis of the ability of representative chimeric antigens (recombinant chimeric proteins) to detect antibody responses elicited by infection with Lyme disease spirochetes over time. Mice were infected with *B. burgdorferi*, blood was collected at the timepoints indicated and used to screen the recombinant chimerics by ELISA. Of those tested, DCFL4 performed the best. Subsequent analyses revealed that HDFL4 and DCFL3a (data not shown) were also highly effective at detecting early antibody responses.

The sensitivity of DCFL4 was then compared with several other chimerics. Mice were infected with *B. burgdorferi* and then sera was collected over time. The chimerics indicated in FIG. 8 were used to coat wells of ELISA plates and then were screened with the serum samples. Of the chimerics tested, as shown in FIG. 8, DCFL4 displayed the best results. These data indicate that the organization of the constructs is critical and not obvious. Subsequently we test two additional chimerics, DCFL3a and HDFL4. Both yielded strong results that are described below.

Comparative Analysis of the Diagnostic Chimeric Antigens to Detect Antibodies of the Course of Infection in Canines.

Each of the chimerics indicated in FIG. 9 were screened with serum from experimentally infected dogs. Sera harvested at 21 days post-infection from 10 dogs were screened by ELISA (FIG. 9A). DCFL4 displayed the highest sensitivity. VlsE was used as a positive control and FhbB as a negative control. The sera were collected at the time points post tick bite indicated. The proteins were then screened with serum collected over time from infected dogs (FIG. 9B) and, as above, DCFL4 yielded the best results.

Diagnostic Chimeric Antigens do not Yield False Positives for Vaccinated Dogs.

There are several Lyme disease vaccines currently on the market for dogs and there is an OspA based vaccine in phase III clinical trials for humans (Valneva/Pfizer). To determine if a false positive result can occur with the chimeric antigens, the chimerics were screened using an ELISA format and serum from dogs vaccinated with each of the currently available vaccines (FIG. 10). No false positives were observed indicating that the chimerics will be effective at diagnosing break-through infections in vaccinated animals.

Optimization of the Serum Dilution and Chromogenic Substrate Exposure Time for the Diagnostic ELISA Using Chimeric Proteins.

Figures 11, 12:
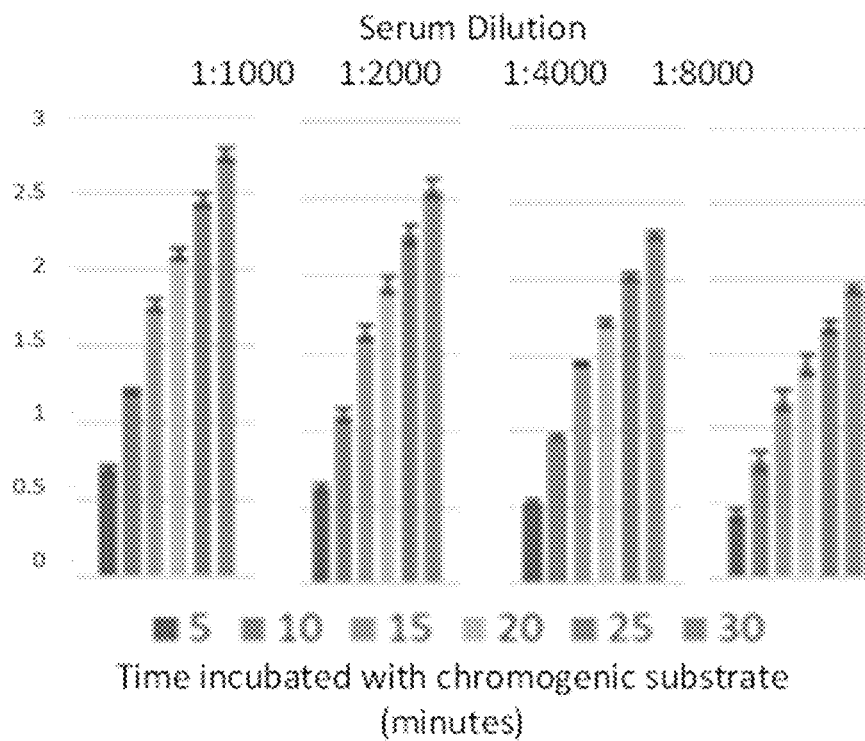
FIG. 11. Optimization of ELISA conditions for diagnostic applications. A serum sample from a dog confirmed to be infected with *B. burgdorferi* was diluted as indicated and then incubated with a chromogenic substrate for increasing lengths of time (as indicated). It can be concluded that about 1:1000 is an optimal dilution for diagnostic assays. An optimal timeframe for incubation with the chromogenic substrate is about 20 minutes (based on convenience and keeping the OD readings from maxing out).
FIG. 12. Screening of the Lyme Disease Biobank Test Serum panel. The Lyme Disease Biobank has generated a well-characterized serum panel of human sera that can be used to validate and compare the sensitivity and specificity of diagnostic antigens. A dot blot format was used. The chimerics and control proteins shown to the left were screened with the serum samples. The serum ID numbers assigned by the Biobank are indicated. Across the top of the image, the two-tier (2TT) scoring results for both IgM and IgG as determined by others are indicated. DCFL4 displayed high sensitivity and specificity. This panel was screened specifically for IgG. DCFL4 proved highly effective in detecting antibodies in human Lyme disease patients with well-characterized disease. The use of a single protein (e.g., DCFL4) offers advantages over the two-tier testing system in terms of speed, cost, sensitivity, and specificity and eliminates the need to test for IgM which can yield false positive results.

To optimize the ELISA conditions and to ensure reproducibility, the following variables were tested: serum dilution, exposure time to the chromogenic substrate, ELISA plates from different manufacturers, and concentration of Tween® 20 in the blocking and wash buffers. FIG. 11 presents the results in which serum dilution and substrate exposure time were assessed using a well-characterized serum sample from an infected dog. The optimal serum dilution proved to be 1:1000. Given that serum is not typically limiting, this dilution is appropriate. Chromogenic substrate exposure time need not be absolute but must be consistent and allow for rapid testing. We determined 20 minutes to be ideal as it keeps the absorbance reading in the linear part of the plot.

Screening of the Lyme Disease Biobank Test Serum Panel.

The Lyme Disease Biobank has generated a well-characterized serum panel that can be used to validate and compare the sensitivity and specificity of diagnostic antigens. An initial test serum panel provided by the Biobank was screened against the chimeric proteins using a dot blot format (FIG. 12). The chimerics and control proteins used are shown on the left. The serum ID numbers are indicated along the top (as assigned by the Biobank). Across the top of the image, the two-tier (2TT) scoring results for both IgM and IgG as determined by others are indicated. DCFL4 displayed high sensitivity and specificity. This panel was screened specifically for IgG. DCFL4 proved highly effective in detecting antibody in Lyme disease patients with well-characterized disease. The use of a single protein (DCFL4) offers advantages over the two-tier testing system in terms of speed, cost, sensitivity, and specificity and eliminates the need to test for IgM which can yield false positive results.

HDFL4: A Highly Sensitive Diagnostic Antigen for Lyme Disease Infections in Humans.

The sensitivity of HDFL4 was independently assessed by a third party using a commercially available serum panel (SeraCare; S1-S15) and a proprietary lateral flow test that is in development. The samples are designated as S1-S15 and they have been tested by SeraCare for both Lyme specific IgG and IgM antibodies. The test employs a proprietary lateral flow approach. Additional human serum samples (ID numbers are shown) were also tested. The sensitivity and specificity of HDFL4 were compared against a multiplex assay that uses 4 antigens (Ag1-Ag4; undisclosed identity). Samples scored as positive are underlined, bolded, and italicized in Table 4 below. The results indicate that HDFL4 detects antibodies with high sensitivity and can be used in place of multiple independent antigens.

TABLE 4

HDFL4: A highly sensitive diagnostic antigen for Lyme disease infections in humans.

| | HDFL4 | Ag1 | Ag2 | Ag3 | Ag4 |
|---|---|---|---|---|---|
| S1 | 24 | 79 | 28 | 161 | 4 |
| S2 | 6.7 | 28 | 4.2 | 12 | 1 |
| S3 | 42 | 66 | 23 | 155 | 4.5 |
| S4 | 22 | 68 | 39 | 116 | 17 |
| S5 | 69 | 25 | 3.7 | 76 | 1.5 |
| S6 | 24 | 28 | 5 | 71 | 0.3 |
| S7 | 18 | 84 | 27 | 74 | 3.4 |

TABLE 4-continued

HDFL4: A highly sensitive diagnostic antigen for Lyme disease infections in humans.

| HDFL4 | Ag1 | Ag2 | Ag3 | Ag4 |
|---|---|---|---|---|
| S8 | 50 | 4.7 | 21 | 48 | 75 |
| S9 | 81 | 158 | 20 | 157 | 6.9 |
| S10 | 79 | 18 | 48 | 96 | 132 |
| S11 | 122 | 4.6 | 3.3 | 88 | 144 |
| S12 | 2 | 4.3 | 3.2 | 9.7 | 1.1 |
| S13 | 14 | 2.6 | 3.9 | 50 | 7.4 |
| S14 | 89 | 11 | 4 | 108 | 40 |
| S15 | 1 | 2.4 | 3.7 | 2.1 | 1.3 |
| 492 | 18 | 0.7 | 6.6 | 110 | 0.6 |
| 524 | 22 | 2.4 | 8.6 | 65 | 0.3 |
| 413 | 104 | 1.3 | 25 | 181 | 0 |
| 417 | 23 | 1.8 | 7.5 | 102 | 0.6 |
| 446 | 0.9 | 2 | 5.8 | 28 | 0.1 |
| 448 | 22 | 0.5 | 8.4 | 34 | 0.3 |
| 449 | 12 | 2 | 11 | 96 | 0.5 |
| 349 | 66 | 2.7 | 9.2 | 5 | 94 |

While the invention has been described in terms of its several exemplary embodiments, those skilled in the art will recognize that the invention can be practiced with modification within the spirit and scope of the appended claims. Accordingly, the present invention should not be limited to the embodiments as described above but should further include all modifications and equivalents thereof within the spirit and scope of the description provided herein.

I claim:

1. A recombinant chimeric polypeptide comprising, in order from amino to carboxy terminus:

i) DbpB without N terminal A (SEQ ID NO: 76) or a variant thereof having at least 95% identity to SEQ ID NO: 76,
   BBA73 (SEQ ID NO: 3) or a variant thereof having at least 95% identity to SEQ ID NO: 73,
   BBK53 (SEQ ID NO: 4) or a variant thereof having at least 95% identity to SEQ ID NO: 4, and
   BBO238 (SEQ ID NO: 5) or a variant thereof having at least 95% identity to SEQ ID NO: 5;
   or
   ii) DbpB without N terminal A (SEQ ID NO: 76) or a variant thereof having at least 95% identity to SEQ ID NO:76,
   BBA73 (SEQ ID NO: 3) or a variant thereof having at least 95% identity to SEQ ID NO: 3, and
   BBK53 (SEQ ID NO: 4) or a variant thereof having at least 95% identity to SEQ ID NO:4;
   or
   iii) BBA24 (SEQ ID NO: 13) or a variant thereof having at least 95% identity to SEQ ID NO:13,
   DbpB (SEQ ID NO: 2) or a variant thereof having at least 95% identity to SEQ ID NO: 2,
   BBK19 (SEQ ID NO: 15) or a variant thereof having at least 95% identity to SEQ ID NO: 15, and
   VlsE (SEQ ID NO: 16) or a variant thereof having at least 95% identity to SEQ ID NO:16.

2. The recombinant chimeric polypeptide of claim 1, wherein the recombinant chimeric polypeptide comprises an amino acid sequence set forth as SEQ ID NO: 1, SEQ ID NO: 6 or SEQ ID NO: 10.

3. The recombinant chimeric polypeptide of claim 1, further comprising an amino or carboxy terminal tag for identifying or purifying the recombinant protein.

* * * * *

SEQUENCE LISTING

```
Sequence total quantity: 76
SEQ ID NO: 1          moltype = AA  length = 808
FEATURE               Location/Qualifiers
source                1..808
                      mol_type = protein
                      organism = synthetic construct
SEQUENCE: 1
LESSSKDLKN KILKIKKEAT GKGVLFEAFT GLKTGSKVTS GGLALREAKV QAIVETGKFL   60
KIIEEEALKL KETGNSGQFL AMFDLMLEVV ESLEDVGIIG LKARVLEESK NNPINTAERL  120
LAAKAQIENQ LKVVKEKQNI ENGGEKKNNK SKKKKNTEAI SELQSSPIKL GKIKVLQKTE  180
KIVSTQNLQN LQQSQFFKNE KEKIIKKIAQ EFDENEKLIN KIGPNIEMFA QTINTDIQKI  240
EPNDQFGINK TLFTEKKDNN IDFMLKDNRL RRLFYSSLNY DENKIKKLAT ILAQTSSSND  300
YHYTLIGLIF WTGFKIQEAF ESAVNILTKD EQKRLIFNFR TKTVKEIQEN FEKLMQERNS  360
WIKIVDNIIG EYDKNTGGCK ADGKILGEVI RVGYEHELDS NKSMQILNNI ETPLKTCCDH  420
IHYDKQKELA IFYYEVGQRY INVGKIKKGK LFQAKALKIY PDLKKGFDIK LAVKELDARI  480
KDDNPKVVML EDIKLEEIPG IVHEKIEIND FTNAPKIEYI AQRERSKNQD KIIKFQFGKF  540
ARALISRNFD LFDSVIADKV NVMGQFESKN DFISTLSSAS SKADADELEY LSVDDYYDLK  600
SLKISKSNDT SFAVNVNAKK NDVTKNFPFW KERQTLIFTT EDDNNWFLSS INQTFFENSE  660
SSDMGSDEIV TEGIFSSLKL YASEHRLLVE IKKTLISLKD PNYRDVVRPV SDYNEEYFNK  720
FFLDLGSEQS KDLIKLFIMV KNEQNNNKFM RIVRWLYSCI EELYSLDIKY SGEGSHEYNR  780
NMPRPTAYEQ YLKVKRYDYN SPVSILPT                                     808

SEQ ID NO: 2          moltype = AA  length = 156
FEATURE               Location/Qualifiers
source                1..156
                      mol_type = protein
                      organism = Borreliella burgdorferi
SEQUENCE: 2
ALESSSKDLK NKILKIKKEA TGKGVLFEAF TGLKTGSKVT SGGLALREAK VQAIVETGKF   60
LKIIEEEALK LKETGNSGQF LAMFDLMLEV VESLEDVGII GLKARVLEES KNNPINTAER  120
LLAAKAQIEN QLKVVKEKQN IENGGEKKNN KSKKKK                            156

SEQ ID NO: 3          moltype = AA  length = 268
FEATURE               Location/Qualifiers
source                1..268
                      mol_type = protein
                      organism = Borreliella burgdorferi
SEQUENCE: 3
NTEAISELQS SPIKLGKIKV LQKTEKIVST QNLQNLQQSQ FFKNEKEKII KKIAQEFDEN   60
EKLINKIGPN IEMFAQTINT DIQKIEPNDQ FGINKTLFTE KKDNNIDFML KDNRLRRLFY  120
SSLNYDENKI KKLATILAQT SSSNDYHYTL IGLIFWTGFK IQEAFESAVN ILTKDEQKRL  180
IFNFRTKTVK EIQENFEKLM QERNSWIKIV DNIIGEYDKN TGGCKADGKI LGEVIRVGYE  240
HELDSNKSMQ ILNNIETPLK TCCDHIHY                                    268

SEQ ID NO: 4          moltype = AA  length = 156
FEATURE               Location/Qualifiers
source                1..156
                      mol_type = protein
                      organism = Borreliella burgdorferi
SEQUENCE: 4
QTFFENSESS DMGSDEIVTE GIFSSLKLYA SEHRLLVEIK KTLISLKDPN YRDVVRPVSD   60
YNEEYFNKFF LDLGSEQSKD LIKLFIMVKN EQNNNKFMRI VRWLYSCIEE LYSLDIKYSG  120
EGSHEYNRNM PRPTAYEQYL KVKRYDYNSP VSILPT                            156
```

```
SEQ ID NO: 5            moltype = AA  length = 156
FEATURE                 Location/Qualifiers
source                  1..156
                        mol_type = protein
                        organism = Borreliella burgdorferi
SEQUENCE: 5
QTFFENSESS DMGSDEIVTE GIFSSLKLYA SEHRLLVEIK KTLISLKDPN YRDVVRPVSD    60
YNEEYFNKFF LDLGSEQSKD LIKLFIMVKN EQNNNKFMRI VRWLYSCIEE LYSLDIKYSG   120
EGSHEYNRNM PRPTAYEQYL KVKRYDYNSP VSILPT                             156

SEQ ID NO: 6            moltype = AA  length = 579
FEATURE                 Location/Qualifiers
source                  1..579
                        mol_type = protein
                        organism = synthetic construct
SEQUENCE: 6
LESSSKDLKN KILKIKKEAT GKGVLFEAFT GLKTGSKVTS GGLALREAKV QAIVETGKFL    60
KIIEEEALKL KETGNSGQFL AMFDLMLEVV ESLEDVGIIG LKARVLEESK NNPINTAERL   120
LAAKAQIENQ LKVVKEKQNI ENGGEKKNNK SKKKKNTEAI SELQSSPIKL GKIKVLQKTE   180
KIVSTQNLQN LQQSQFFKNE KEKIIKKIAQ EFDENEKLIN KIGPNIEMFA QTINTDIQKI   240
EPNDQFGINK TLFTEKKDNN IDFMLKDNRL RRLFYSSLNY DENKIKKLAT ILAQTSSSND   300
YHYTLIGLIF WTGFKIQEAF ESAVNILTKD EQKRLIFNFR TKTVKEIQEN FEKLMQERNS   360
WIKIVDNIIG EYDKNTGGCK ADGKILGEVI RVGYEHELDS NKSMQILNNI ETPLKTCCDH   420
IHYQTFFENS ESSDMGSDEI VTEGIFSSLK LYASEHRLLV EIKKTLISLK DPNYRDVVRP   480
VSDYNEEYFN KFFLDLGSEQ SKDLIKLFIM VKNEQNNNKF MRIVRWLYSC IEELYSLDIK   540
YSGEGSHEYN RNMPRPTAYE QYLKVKRYDY NSPVSILPT                          579

SEQ ID NO: 7            moltype = AA  length = 540
FEATURE                 Location/Qualifiers
source                  1..540
                        mol_type = protein
                        organism = synthetic construct
SEQUENCE: 7
LESSSKDLKN KILKIKKEAT GKGVLFEAFT GLKTGSKVTS GGLALREAKV QAIVETGKFL    60
KIIEEEALKL KETGNSGQFL AMFDLMLEVV ESLEDVGIIG LKARVLEESK NNPINTAERL   120
LAAKAQIENQ LKVVKEKQNI ENGGEKKNNK SKKKKDKQKE LAIFYYEVGQ RYINVGKIKK   180
GKLFQAKALK IYPDLKKGFD IKLAVKELDA RIKDDNPKVV MLEDIKLEEI PGIVHEKIEI   240
NDFTNAPKIE YIAQRERSKN QDKIIKFQPG KFARALISRN PDLFDSVIAD KVNVMGQFES   300
KNDFISTLSS ASSKADADEL EYLSVDDYYD LKSLKISKSN DTSFAVNVNA KKNDVTKNFP   360
FWKERQTLIF TTEDDNNWFL SSINQTFFEN SESSDMGSDE IVTEGIFSSL KLYASEHRLL   420
VEIKKTLISL KDPNYRDVVR PVSDYNEEYF NKFFLDLGSE QSKDLIKLFI MVKNEQNNNK   480
FMRIVRWLYS CIEELYSLDI KYSGEGSHEY NRNMPRPTAY EQYLKVKRYD YNSPVSILPT   540

SEQ ID NO: 8            moltype = DNA  length = 2016
FEATURE                 Location/Qualifiers
source                  1..2016
                        mol_type = other DNA
                        organism = synthetic construct
SEQUENCE: 8
atggcacatc accaccaca tcacgtgggt accggttcga atgatgacga cgacaagagt     60
ccggatcccg gtaaaggcgt gctgttcgag gcgtttaccg gtctgaaaac cggcagcaag   120
gttaccagcg gtggcctggc gctgcgtgaa gcgaaggtgc aggcgatcgt tgaaaccggc   180
aagttcctga aaatcattga ggaagaggcg ctgaagctga agaaaccgg taacagcggc   240
caattcctgg cgatgtttga cctgatgctg aagtggttg agagcctgga agatgtgggt   300
atcattggcc tgaaagcgcg tgttctggaa gagagcaaga caaacccgat caacaccgcg   360
gaacgtctgc tggcggcgaa agcgcagatt gagaaccaac tgaaggtggt taaactgcag   420
aagaccgaga aaatcgtgag cacccagaac ctgcaaaacc tgcagcaaag ccagttcttt   480
aagaacgaaa aggagaagat cattaagaaa attgcgcaag aattcgacga aaacgagaaa   540
ctgatcaaca agattggtcc gaacatcgaa atgtttgcgc agaccattaa caccgacatc   600
caaaaaattg agccgaacga tcagttcggc atcaacaaga ccctgtttac cgaaaagaaa   660
gacaacaaca ttgatttcat gctgaaagac aaccgtctgc gtcgtctgtt ttacagcagc   720
ctgaactatg atgagaacaa gatcaagaaa ctggcgacca ttctggcgca gaccagcagc   780
agcaacgact accactatac cctgatcggt ctgatttttct ggaccggctt taaaattcag   840
gaagcgttcg aaagcgcggt gaacatcctg accaaagatg aacaaaagcg tctgatttc   900
aactttcgta ccaagaccgt taaagagatc aggaaaact cgagaaact gatgcaagag   960
cgtaacagct ggatcaagat tgtggacaac atcattggtg aatacgataa aaacaccggt  1020
ggctgcaaag cggacggcaa gatcctgggc gaggtgatcc gtgttggcta tgaacacgag  1080
ctggatagca acaagagcgg taaaatcaag aaggtcaagc tgttccaggc gaaggcgctg  1140
aaaatctacc cggacctgaa gaaaggtttt gatattaaac tggcggtgaa ggagctggac  1200
gcgcgtatca agacgataa cccgaaggtg ttatgctgg aagatattaa actggaagag  1260
atcccgggca ttgttcacga aaagatcgag attaacgact tcaccaacgc gccgaaaatc  1320
gaatatattg cgcaacgtga gcgtagcaag aaccaggata gatcatcaa gttccaattc  1380
ggcaagtttg cgcgtgcgct gatcagccgt aacttcgacc tgtttgatag cgttattgcg  1440
gacaaagtga acgttatggg ccaattcgag agcaagaacg attttatcag cacccgttgt  1500
agcgcgagca gcaaggcgga tgcgatgaa ctgagtacc tgagcgtgga cgattactat  1560
gacctgaaga gcctgaaaat cagcaagagc aacgatacca gcttcgcggt gaacgttaac  1620
gcgaagaaaa acgacgttac caaaaacttc ccgttttgga ggaaggtat ctttagcagc  1680
ctgaaactgt acgcgagcga acaccgtctg ctggttgaga tcaagaaaac cctgattagc  1740
ctgaaggacc cgaactatcg tgatgtggtt cgtccggtta gcgattacaa cgaagagtac  1800
```

```
ttcaacaagt tctttctgga cctgggtagc gagcagagca aagatctgat caagctgttc   1860
attatggtga agaacgaaca aaacaacaac aagttcatgc gtatcgttcg ttggctgtac   1920
agctgcattg aagagctgta cagcctggac atcaagtata gcggtgaagg cagccacgag   1980
tacaaccgta acatgccgcg tccgaccgcg tattaa                              2016

SEQ ID NO: 9            moltype = DNA   length = 1741
FEATURE                 Location/Qualifiers
source                  1..1741
                        mol_type = other DNA
                        organism = synthetic construct
SEQUENCE: 9
gctggagagc agcagcaagg acctgaagaa caagatcctg aagattaaga agaagcgac    60
cggcaagggc gtgctgttcg aggcgtttac cggtctgaag accggcagca aagttaccag   120
cggtggcctg gcgctgcgtg aagcgaaagt gcaagcgatc gttgagaccg gcaagttcct   180
gaaaatcatt gaggaagagg cgctgaagct gaaagagacc ggtaacagcg gccagttcct   240
ggcgatgttt gacctgatgc tggaagtggt tgagagcctg gaagatgtgg gtatcattgg   300
cctgaaagcg cgtgttctgg aagagagcaa gaacaacccg atcaacaccg cggaacgtct   360
gctggcgaaa aagcgcagag ttgaaaaacca actgaaggtg gttaaggaga aacaaaaacat   420
cgaaaacggt ggcgagaaga aaaacaacaa gagcaagaaa aagaaaaaca ccgaagcgat   480
tagcgagctg caaagcagcc cgatcaagct gggcaagatt aaagtgctgc agaagaccga   540
gaaaatcgtt agcacccaga acctgcaaaa cctgcagcaa agccaattct ttaagaacga   600
aaaggagaag atcattaaga aaatcgcgca ggaattcgac gaaaacgaaa agctgatcaa   660
caaaattggt ccgaacatcg aaatgtttgc gcagaccatt aacaccgaca tccaaaaaat   720
tgagccgaac gatcagttcg gcattaacaa gaccctgttt accgaaaaga agacaacaa    780
catcgatttc atgctgaaag acaaccgtct gcgtcgtctg ttttacagca gcctgaacta   840
tgatgaacaa aagatcaaga aactggcgca cattctggac cagaccagca gcagcaacga   900
ctaccactat accctgatcg gtctgatttt ctggaccggc tttaaaattc aagaggcgtt   960
cgaaagcgcg gtgaacatcc tgaccaagga tgaacagaaa cgtctgattt tcaactttcg  1020
taccaagacc gttaaagaga tccaagaaaa cttgagaaa ctgatgcagg agcgtaacag   1080
ctggatcaag attgtggaca acattgttgg tgaatacgat aagaacaccg gtggctgcaa  1140
ggcggacggt aaaatcctgg gcgaggtgat ccgtgttggc tatgaacacg agctggatag  1200
caacaaaagc atgcaaatcc tgaacaacat gaaacccg ctgaagacct gctgccgcca     1260
catccactac cagaccttct tgaaaaacag cgagagcagc gacatgggta gcgatgaat   1320
cgtgaccgag gcattttca gcagcctgaa actgtacgcg agcgaacaccg gtctgctggt  1380
tgagatcaag aaaaacctga ttagcctgaa ggacccgtga tatcgtgatg tggttcgtcc   1440
ggttagcgat tacaacgaag agtacttcaa caagttcttt ctggacctgg gtagcgagca  1500
aagcaaggat ctgatcaaac tgttcattat ggtgaagaac gaacagaaca acaacaaatt   1560
tatgcgtatc gttcgttggc tgtacagctg cattgaagag ctgtacagcc tggacatcaa  1620
gtatagcggt gaaggcagcc acgagtataa ccgtaacatg ccgcgtccga ccgcgtacga  1680
gcagtatctg aaggtgaaac gttacgatta taacagcccg gttagcatcc tgccgaccta  1740
a                                                                  1741

SEQ ID NO: 10           moltype = AA    length = 843
FEATURE                 Location/Qualifiers
source                  1..843
                        mol_type = protein
                        organism = synthetic construct
SEQUENCE: 10
TKIRLERSAK DITDEIDAIK KDAALKGVNF DAFKDKKTGS GVSENPFILE AKVRATTVAE    60
KFVIAIEEEA TKLKETGSSG EFSAMYDLMF EVSKPLQKLG IQEMTKTVSD AAEENPPTTA   120
QGVLEIAKKM REKLQRVHTK NYCTLKKKEN STFTDEKCKN NALESSSKDL KNKILKIKKE   180
ATGKGVLFEA FTGLKTGSKV TSGGLALREA KVQAIVETGK FLKIIEEEAL KLKETGNSGQ   240
FLAMFDLMLE VVESLEDVGI IGLKARVLEE SKNNPINTAE RLLAAKAQIE NQLKVVEKQ    300
NIENGGEKKN NKSKKKKNLF SKDSRSRQKY NFKVPAKSVS NPINKENIDT EKGTNTTLCI   360
KEKDSRIIIK DCINNQELFK VKSKRRYDFK KAMLLGIQTA LKVINIGNNN KKLTSIKKHN   420
DHILLEFKDN KIYIIRLSEL KKHLLKSKKK PLLGSPIPGG GDAEFVDDPD GRIEAELEAE   480
QEQEMLDRED FGDEEDEELE EEIFGKEKPN NDKDDPTNKF YQSVIQLGNG FLDVFTSFGG   540
LVAEAFGFKS DPKKSDVKTY FTTVAAKLEK TKTDLNSLPK EKSDISSTTG KPDSTGSVGT   600
AVEGAIKEVS ELLDKLVKAV KTAEGASSGT AAIGEVVADA AKAVADKAS VKGIAKGIKE    660
IVEAAGGSEK LKAVAAAKGE NNKGAGKLFG KAGAAAHGDS EAASKAAGAV SAVSGEQILS   720
AIVTAADAEE QDGKKPEEAK NPIAAAIGDK DGGAEFGQDE MKKDDQIAAA IALRGMAKDG   780
KFAVKDGEKE KAEGAIKGAA ESAVRKVLGA ITGLIGDAVS SGLRKVGDSV KAASKETPPA   840
LNK                                                                843

SEQ ID NO: 11           moltype = DNA   length = 2532
FEATURE                 Location/Qualifiers
source                  1..2532
                        mol_type = other DNA
                        organism = synthetic construct
SEQUENCE: 11
acaaaaatta gattagaacg aagcgctaaa gacattacag atgaaataga tgcaattaaa    60
aaagacgctg ctcttaaggg cgtaaatttt gatgccttta agataaaaa aacgggtagt    120
ggggtatcag aaaatccatt catacttgaa gcaaagtgc gagctactac agtagcggaa   180
aaattcgtaa tagcaataga agaggaagct actaaactca aagaaactgg aagtagtagt   240
gaattttcag caatgtatga tttaatgttt gaagtctcaa aaccattaca aaaattggga   300
atacaagaga tgcaaaaaac agtctcagat gcagctgaag agaatcctcc aactacagct   360
caaggagtgc ttgaaattgc aaaaaaaatg agagaaaaat acaaagggt tcatacaaaa   420
aactactgca cccttaaaaa gaaggaaaat tctacttttac ctgatgaaaa atgcaaaaat   480
aacgctcttg aatcgtcctc taaggattta aaaaacaaaa ttttaaaaat aaaaaaagaa   540
```

```
gccacgggaa aaggtgtact ttttgaagct tttacaggtc ttaaaaccgg ttccaaggta    600
acaagtggtg gactagcctt aagagaagca aaagtacaag ccattgttga aacaggaaag    660
ttccttaaga aatagaagaa agaagcttta aagcttaaag aaactggaaa cagtggtcaa    720
ttcttggcta tgtttgactt aatgcttgag gttgtagaat cgctagaaga cgttggaata    780
ataggcttaa aagcccgtgt tttagaggaa tctaaaaata atcctataaa cacagctgaa    840
agattgcttg cggctaaagc tcaaatagaa aatcaactta aagtggttaa ggaaaaacaa    900
aatattgaaa atggtggaga gaaaaaaaat aataaaagca aaaaaaagaa aaatcttttt    960
tcaaaagatt ctcgatcacg ccaaaaatac aattttaaag tacccgctaa atcggtttca   1020
aatcctatca ataaagaaaa tatagacact gaaaaagcta ctaacactac actttgcata   1080
aaagaaaaag atagcagaat tataattaaa gattgtatta ataatcaaga cttttttaaa   1140
gtaaaatcta aaagaagata tgattttaaa aaagccatgc ttcttggaat tcaaacagct   1200
ttaaaagtta taaatattgg caataataat aaaaaattaa cttccataaa aaaacataat   1260
gatcatattt tattagaatt taaagataat aagatatata taattcgatt atctgaactt   1320
aaaaaacatt tactaaaaag caagaaaaaa ccactattag gaagtccgat accgggcggc   1380
ggagatgcag aatttgtaga tgatcctgat ggcagaatag aagcagaatt agaggcagaa   1440
caagagcaag agatgttaga tagagaagat tttggagacg aagaagacga agaattagaa   1500
gaagaaatat ttggaaaaga aaaacctaac aatgataagg acgacccaac aaacaaattt   1560
taccaatctg tcatacaatt aggtaacgga tttcttgatg tattcacatc ttttggtggg   1620
ttagtagcag aggcttttgg atttaaatca gatccaaaaa aatctgatgt aaaaacctat   1680
tttactactg tagctgccaa attggaaaca acaaaaaccg atcttaatag tttgcctaag   1740
gaaaaaagcg atataagtag tacgacgggg aaaccagata gtacaggttc tgttggaact   1800
gccgttgagg gggctattaa ggaagttagc gagttgttgg ataagctggt aaaagctgta   1860
aagacagctg aggggggcttc aagtggtact gctgcaattg gagaagttgt ggctgatgct   1920
gatgctgcaa aaggttgctga taaggcgagt gtgaagggga ttgctaaggg gataaaggag   1980
attgttgaag ctgctggggg gagtgaaaag ctgaaagctg ttgctgctgc taaggggag   2040
aataataaag gggcagggaa gttgtttggg aaggctgagg ctgctgctca tggggacagt   2100
gaggctgcta gcaaggcggc tggtgctgtt agtgctgtta gtggggagca gatattaagt   2160
gcgattgtta cggctgctga tgcggctgag caggatggaa agaagcctga ggaggctaaa   2220
aatccgattg ctgctgctat tggggataaa gatggggtg cggagtttgg tcaggatgag   2280
atgaagaagg atgatcagat tgctgctgct attgctttga ggggatggc taaggatgga   2340
aagtttgctg tgaaggatgg tgagaaagag aaggctgagg gggctattaa gggagctgct   2400
gagtctgcag ttcgcaaagt tttagggggct attactgggc taataggaga cgccgtgagt   2460
tccgggctaa ggaaagtcgg tgattcagtg aaggctgcta gtaaagaaac acctcctgcc   2520
ttgaataagt aa                                                       2532

SEQ ID NO: 12            moltype = AA   length = 191
FEATURE                  Location/Qualifiers
source                   1..191
                         mol_type = protein
                         organism = Borreliella burgdorferi
SEQUENCE: 12
MIKCNNKTFN NLLKLTILVN LLISCGLTGA TKIRLERSAK DITDEIDAIK KDAALKGVNF    60
DAFKDKKTGS GVSENPFILE AKVRATTVAE KFVIAIEEEA TKLKETGSSG EFSAMYDLMF   120
EVSKPLQKLG IQEMTKTVSD AAEENPPTTA QGVLEIAKKM REKLQRVHTK NYCTLKKKEN   180
STFTDEKCKN N                                                       191

SEQ ID NO: 13            moltype = AA   length = 161
FEATURE                  Location/Qualifiers
source                   1..161
                         mol_type = protein
                         organism = Borreliella burgdorferi
SEQUENCE: 13
TKIRLERSAK DITDEIDAIK KDAALKGVNF DAFKDKKTGS GVSENPFILE AKVRATTVAE    60
KFVIAIEEEA TKLKETGSSG EFSAMYDLMF EVSKPLQKLG IQEMTKTVSD AAEENPPTTA   120
QGVLEIAKKM REKLQRVHTK NYCTLKKKEN STFTDEKCKN N                      161

SEQ ID NO: 14            moltype = AA   length = 211
FEATURE                  Location/Qualifiers
source                   1..211
                         mol_type = protein
                         organism = Borreliella burgdorferi
SEQUENCE: 14
MKKYIINLSL CLLLLSCNLF SKDSRSRQKY NFKVPAKSVS NPINKENIDT EKGTNTTLCI    60
KEKDSRIIIK DCINNQELFK VKSKRRYDFK KAMLLGIQTA LKVINIGNNN KKLTSIKKHN   120
DHILLEFKDN KIYIIRLSEL KKHLLKSKKK PLLGSPIPGG GDAEFVDDPD GRIEAELEAE   180
QEQEMLDRED FGDEEDEELE EEIFGKEKPN N                                 211

SEQ ID NO: 15            moltype = AA   length = 194
FEATURE                  Location/Qualifiers
source                   1..194
                         mol_type = protein
                         organism = Borreliella burgdorferi
SEQUENCE: 15
NLFSKDSRSR QKYNFKVPAK SVSNPINKEN IDTEKGTNTT LCIKEKDSRI IIKDCINNQE    60
LFKVKSKRRY DFKKAMLLGI QTALKVINIG NNNKKLTSIK KHNDHILLEF KDNKIYIIRL   120
SELKKHLLKS KKKPLLGSPI PGGGDAEFVD DPDGRIEAEL EAEQEQEMLD REDFGDEEDE   180
ELEEEIFGKE KPNN                                                    194
```

-continued

```
SEQ ID NO: 16          moltype = AA  length = 332
FEATURE                Location/Qualifiers
source                 1..332
                       mol_type = protein
                       organism = Borreliella burgdorferi
SEQUENCE: 16
DKDDPTNKFY QSVIQLGNGF LDVFTSFGGL VAEAFGFKSD PKKSDVKTYF TTVAAKLEKT  60
KTDLNSLPKE KSDISSTTGK PDSTGSVGTA VEGAIKEVSE LLDKLVKAVK TAEGASSGTA  120
AIGEVVADAD AAKVADKASV KGIAKGIKEI VEAAGGSEKL KAVAAAKGEN NKGAGKLFGK  180
AGAAAHGDSE AASKAAGAVS AVSGEQILSA IVTAADAAEQ DGKKPEEAKN PIAAAIGDKD  240
GGAEFGQDEM KKDDQIAAAI ALRGMAKDGK FAVKDGEKEK AEGAIKGAAE SAVRKVLGAI  300
TGLIGDAVSS GLRKVGDSVK AASKETPPAL NK                              332

SEQ ID NO: 17          moltype = AA  length = 317
FEATURE                Location/Qualifiers
source                 1..317
                       mol_type = protein
                       organism = Borreliella burgdorferi
SEQUENCE: 17
MNLIFNINLY LKKYFLVLFL VLVACVGDNK LDDKNIDKEK ESSYRFPVIA MKVKKGILSD  60
YLSLNGDVDT KVKADIFPDA VGKITSLRIK LGAYVQKGQI VATLDPSRPG SVYLKSPVRA  120
PISGYILNIT KKIGETVNPQ SNIAVVGRID TKQILTYVSE KYISNIKVGN DAIIEVGAYS  180
NEKFKAKVSE ISPILDSKSR TIEVYLTPIG SNLDKLIIGM FSKIKLITKR FKDVIKISRE  240
AVVEREGKKF VFKVDLESKS VQMLPITVLF EIDNIVALSG EVEENDLIVV EGMSALSNGS  300
LINLVDTKEG LSAESNI                                               317

SEQ ID NO: 18          moltype = AA  length = 336
FEATURE                Location/Qualifiers
source                 1..336
                       mol_type = protein
                       organism = Borreliella burgdorferi
SEQUENCE: 18
MIINHNTSAI NASRNNGINA ANLSKTQEKL SSGYRINRAS DDAAGMGVSG KINAQIRGLS  60
QASRNTSKAI NFIQTTEGNL NEVEKVLVRM KELAVQSGNG TYSDADRGSI QIEIEQLTDE  120
INRIADQAQY NQMHMLSNKS ASQNVRTAEE LGMQPAKINT PASLSGSQAS WTLRVHVGAN  180
QDEAIAVNIY AANVANLFSG EGAQTAQAAP VQEGVQQEGA QQPAPATAPS QGGVNSPVNV  240
TTTVDANTSL AKIENAIRMI SDQRANLGAF QNRLESIKNS TEYAIENLKA SYAQIKDATM  300
TDEVVAATTN SILTQSAMAM IAQANQVPQY VLSLLR                          336

SEQ ID NO: 19          moltype = AA  length = 389
FEATURE                Location/Qualifiers
source                 1..389
                       mol_type = protein
                       organism = Borreliella burgdorferi
SEQUENCE: 19
MNTKATTPLL LLFLIQSLAF SSEIFEFKYI KGSKFRLEGT DNQKIYFNGH YNSSSNTNIQ  60
ISSEIKDIKE NFASIKAFFR ILKRENINEP YLLNEEFEEI FSVNKQGEYT IGANQKRPSV  120
RGIPRFPKTP IKINEKWSYL AEEYIEASKI DKSIKDFVVK FNVNYEYKGK EEHNGKHYHI  180
ILSNYESQYN VKNISFYQKV DQKIYFDNEI GNTYKYSDKY IFEINQNNNQ HFKMIGNSLG  240
RIVSIELPND NLIETEVENY IREKKIKAIE VEKNNKGINL SFDIEFYPNS FQILQKEYKK  300
IDLIAKLLEK FKKNNILIEG HTEQFGLEEE MHELSEKRAR AIGNYLIKMK VKDKDQILFK  360
GWGSQKPKYP KSSPLKAKNR RVEITILNN                                  389

SEQ ID NO: 20          moltype = AA  length = 442
FEATURE                Location/Qualifiers
source                 1..442
                       mol_type = protein
                       organism = Borreliella burgdorferi
SEQUENCE: 20
MMRSLYSGVS GLQNHQTRMD VVGNNIANVN TIGFKKGRVN FQDMISQSIS GASRPTDARG  60
GTNPKQVGLG MNVASIDTIH TQGAFQSTQK ASDLGVSGNG FFILKEGKNL FYTRAGAFDV  120
DSDRHLVNPA NGMRIQGWMA RDLEGEKVIN TASDIEDLII PIGDKEGAKS TKNVTFACNL  180
DKRLPLIQEG ANPADIARGT WVVNKSLYDS FGNVSVLELR VVKDLNTPNL WNATVLINGE  240
QNSNFTLGFD NEGALASLNG QPGQKGDILQ IPITFNVLGA NVGEVGEQQT VNLKLGTVGS  300
YTDSITQFAD SSSTKAIIQD GYGMGYMENY EIDQNGVIVG IYSNGIRRDL GKIALASFMN  360
PGGLAKSGDT NFVETSNSGQ VRIGETGLAG LGDIRSGVLE MANVDLAEQF TDMIVTQRGF  420
QANAKTITTS DQLLQELVRL KN                                         442

SEQ ID NO: 21          moltype = AA  length = 201
FEATURE                Location/Qualifiers
source                 1..201
                       mol_type = protein
                       organism = Borreliella burgdorferi
SEQUENCE: 21
MQSKNKLIRL LIIIITLFFN VENIFTNEKS KNNITGQNST TDPKIESLKA KTKIKFGFIL  60
PYPTAIEFSI NNFDIGVGVT ILSVSEFFPK SPIALLFKIY CDYIFLNLKF KDSNFIFFLG  120
SSLFFEIGKI TSSDLTNVSS GITYKIGVGL PLGIIYEAYY DIIEIIIKTT PSIFIGQMPN  180
GNLIFPIKGN FSIGIKGSLK I                                          201
```

```
SEQ ID NO: 22            moltype = AA   length = 618
FEATURE                  Location/Qualifiers
source                   1..618
                         mol_type = protein
                         organism = Borreliella burgdorferi
SEQUENCE: 22
MKSHILYKLI IFLTTSAAIF AADALKEKDI FKINPWMPTF GFENTSEFRL DMDELVPGFE   60
NKSKITIKLK PFEANPELGK DDPFSAYIKV EDLALKAEGK KGDQFKIDVG DITAQINMYD  120
FFIKISTMTD FDFNKESLFS FAPMTGFKST YYGFPSNDRA VRGTILARGT SKNIGTIQLG  180
YKLPKLDLTF AIGGTGTGNR NQENDKDTPY NKTYQGILYG IQATWKPIKN LLDQNEDTKS  240
VIAETPFELN FGLSGAYGNE TFNNSSITYS LKDKSVVGND LLSPTLSNSA ILASFGAKYK  300
LGLTKINDKN TYLILQMGTD FGIDPFASDF SIFGHISKAA NFKKETPSDP NKKAEIFDPN  360
GNALNFSKNT ELGIAFSTGA SDSIGFAWNKDT GEKESWAIKG SDSYSTRLFG EQDKKSGVAL  420
GISYGQNLYR SKDTEKRLKT ISENAFQSLN VEISSYEDNK KGIINGLGWI TSIGLYDILR  480
QKSVENYPTT ISSTTENNQT EQSSTSTKTT TPNLTFEDAM KLGLALYLDY AIPIASISTE  540
AYVVPYIGAY ILGPSNKLSS DATKIYLKTG LSLEKLIRFT TISLGWDSNN IIELANKNTN  600
NAAIGSAFLQ FKIAYSGS                                                618

SEQ ID NO: 23            moltype = AA   length = 430
FEATURE                  Location/Qualifiers
source                   1..430
                         mol_type = protein
                         organism = Borreliella burgdorferi
SEQUENCE: 23
MARVKGQKVK ECSFCGLSVA ELGGNVVISN GVAICPECSK ICHNLFKEKL CKPLDSKSNG   60
LPTPKQLKDH LDMYVVGQED AKKVLSVAVY NHYKRILKNN KYDNGIEIEK SNILLVGPTG  120
SGKTLLAKTL AAEMNVPFAI ADATTLTEAG YVGEDVENIL LKLIHAAHGD VSLAEKGIIY  180
IDEIDKIAKK NENVSITRDV SGEGVQQALL KIIEGTVANV PPRGGRKHPY EDTIEINTQN  240
ILFICGGAFV GLENIVKNRI NKSSIGFSAI EKKNIREDTS LKYLEMEDLI KFGLIPEFVG  300
RLPVHSYLEK LNKEDLLRIL VDPQNSIVKQ YYHMFKMDNV ELVFEKDALE SIVDEAILKN  360
TGARGLRSIL EGLLKDVMFE VPSISKAKKV VVTKESVLNA DVNPLILVGN AIKKPWAKEL  420
YEINLKYDKK                                                         430

SEQ ID NO: 24            moltype = AA   length = 222
FEATURE                  Location/Qualifiers
source                   1..222
                         mol_type = protein
                         organism = Borreliella burgdorferi
SEQUENCE: 24
MLIARIMNIN TLFYGMIIII FALISCNHKN IQYDKRIKKF LDKNKIEYKI DSENDFIAFK   60
DINNNEKEEV IIRSRLNSYK NSKIREIFGI VKVFDINTPK IKEISDSLMS DSYNNRVFGS  120
WEIIHNAERG INSLVYIVKA EEFANDTFLL DAIDEIASTI SIFKKIITTN NENIDNNEEN  180
NNTNESNEQP TLKQEKTNST KESNNELKED QIEEELQEIK AQ                     222

SEQ ID NO: 25            moltype = AA   length = 261
FEATURE                  Location/Qualifiers
source                   1..261
                         mol_type = protein
                         organism = Borreliella burgdorferi
SEQUENCE: 25
MLLSRKIRDY GAKYRGKEIK MSTEINSFLN LRNTIEMRIG SYTAFGVIYS ISMDSLKLIF   60
QEDTVLPALA KNKNLGSIQL KKNSDSKSSA AFFPFLSVKL LSASAYSSLN KEYNLLTLEF  120
LSPAPEEIAI KVGKLLDLKL GQNQRIHERI IIDKDSIRKL KIDSDKAFIK FNGAKHKCLI  180
KDLSYGGALV ISSFDYGDVE EDAIDLIFSF EFIDGEIFIE GKSKSLSVIQ TPSGKVFALG  240
IAFDEDKIPL EYTMLIHDYF N                                            261

SEQ ID NO: 26            moltype = AA   length = 282
FEATURE                  Location/Qualifiers
source                   1..282
                         mol_type = protein
                         organism = Borreliella burgdorferi
SEQUENCE: 26
MKRVIVSFVV LILGCNLDDN SKMERKGSNK LIRESGSDRR GQENRALGAM NFGLFSGDSG   60
VVYDLQNYET LKALENKNKF IDYSKIEFLE GTKSINAFIW AVSVRWIKIK ARDLFGECGD  120
FIKELKGIKY SYLVSPVDGS YISYAMPIIV FETTRESDPL YSVSGFKLIS KGNDINFNEN  180
KSGFWGRLPM SEKSVESGLV TAYPFGSSDA KKVIEAFASL YNNGTWSDMI AEITIKSKQY  240
PKNEKVYRIT LDSQLFNVAM KKIIEKYPKI KSASAFAFNSL IN                    282

SEQ ID NO: 27            moltype = AA   length = 273
FEATURE                  Location/Qualifiers
source                   1..273
                         mol_type = protein
                         organism = Borreliella burgdorferi
SEQUENCE: 27
MKKYLLGIGL ILALIACKQN VSSLDEKNSV SVDLPGEMKV LVSKEKNKDG KYDLIATVDK   60
LELKGTSDKN NGSGVLEGVK ADKSKVKLTI SDDLGQTTLE VFKEDGKTLV SKKVTSKDKS  120
STEEKFNEKG EVSEKIITRA DGTRLEYTGI KSDGSGKAKE VLKGYVLEGT LTAEKTTLVV  180
KEGTVTLSKN ISKSGEVSVE LNDTSSAAT KKTAAWNSGT STLTITVNSK KTKDLVFTKE  240
NTITVQQYDS NGTKLEGSAV EITKLDEIKN ALK                               273
```

```
SEQ ID NO: 28              moltype = AA  length = 296
FEATURE                    Location/Qualifiers
source                     1..296
                           mol_type = protein
                           organism = Borreliella burgdorferi
SEQUENCE: 28
MRLLIGFALA LALIGCAQKG AESIGSQKEN DLNLEDSSKK SHQNAKQDLP AVTEDSVSLF    60
NGNKIFVSKE KNSSGKYDLR ATIDQVELKG TSDKNNGSGT LEGSKPDKSK VKLTVSADLN   120
TVTLEAFDAS NQKISSKVTK KQGSITEETL KANKLDSKKL TRSNGTTLEY SQITDADNAT   180
KAVETLKNSI KLEGSLVGGK TTVEIKEGTV TLKREIEKDG KVKVFLNDTA GSNKKTGKWE   240
DSTSTLTISA DSKKTKDLVF LTDGTITVQQ YNTAGTSLEG SASEIKNLSE LKNALK       296

SEQ ID NO: 29              moltype = AA  length = 194
FEATURE                    Location/Qualifiers
source                     1..194
                           mol_type = protein
                           organism = Borreliella burgdorferi
SEQUENCE: 29
MTALLERLKQ KQKELKLDAD NKPKAKKGKK ATVFSKIEEV KGRKIYHTKI FNDFYTFGIS    60
KNEPTKFFIS LRGIFNIEDI SMFHLFSVRE DDEFMGIYYG IRKLDKAFIV KNFNKKETYT   120
LRKCEYIEFR FKKGSVFCYL NGLHILLKKD RVNSPYYNTL LNIILELETE LYAFYSKKLS   180
KGGIIPEWIK KRQK                                                    194

SEQ ID NO: 30              moltype = AA  length = 212
FEATURE                    Location/Qualifiers
source                     1..212
                           mol_type = protein
                           organism = Borreliella burgdorferi
SEQUENCE: 30
MQRISILLML LAVFSCKQFG DVKSLTEIDS GNGIPLVVSD VVKDLIPKEI SLTPEEAEKL    60
ESLKVFLKDA MSVNGREEAL KAEYEKSYKE FFDWLSKDVN RQKEFISSFD NISSIVSKAV   120
DASKKRRPTE QQSLGFKEYV CYKIKNSKGE ALSLFFQKVV DAFGADPYKK DNDESVQKPV   180
KCNEEIFKVI KKVLTESESN NELKNLKNYG NV                                212

SEQ ID NO: 31              moltype = AA  length = 414
FEATURE                    Location/Qualifiers
source                     1..414
                           mol_type = protein
                           organism = Borreliella burgdorferi
SEQUENCE: 31
MNGKLRKALK IAIFTTLLLV ISCNANMDTN DKNKALNEYK LKNISEVIKN SLQLESDPKL    60
KKEPESNINQ STPPILEIEK IEPGKQEMSL KSEFGSESLM PLEEPEEANM AKSEEEIAKI   120
QEKLLLIGAS DEITDQELGE NMQKFLNPTT VEFKISTTTN ETILTTIEEE EINNNKDKIF   180
DHKEENVTLG NNSLENATLN KNTITLAQNQ KYTTHLKNDD KFITKEYLKQ VRDSLDKALN   240
AIKNLETSKE FRELENLPKD QENSPSAKKE STESNINNTN TENIEIIKNR LLEELNKSEL   300
IFEDTKDPLG TSTIKKVIDA AKKWQEKENS SQIDWDLGFK FHPNPKFYNK LTAQEYKVLA   360
EKFTKVKNEY KNTKEQLKAE SKLTTNSISK IINATKEFAN QVINLILLVE KNYQ         414

SEQ ID NO: 32              moltype = AA  length = 277
FEATURE                    Location/Qualifiers
source                     1..277
                           mol_type = protein
                           organism = Borreliella burgdorferi
SEQUENCE: 32
MSKKVILILL EILILSCDLS INKEQKTKEK TSEKQESEKQ NIEKQEPEKQ KQNAAKIIPT    60
VSIQTVEIRE SNQIPKSIEK YYKQAYPIQT FTLDFSITRE KEFLKPEDKI LPTQGKVESL   120
SILINKKLLD FKAPENPKSS TLKNFKEIKN IENFFQNQDL LFVLTLKDKN NNNTINIMLN   180
PPNDIQKPKD YILKDLKDTI KKGTGEKYLN PIYRFQIKNK KDYHSIDYNK VTISEKTIEL   240
DLLPHEQVFQ MNKNFTKILD TITDLNNLKL VIQKELV                           277

SEQ ID NO: 33              moltype = AA  length = 302
FEATURE                    Location/Qualifiers
source                     1..302
                           mol_type = protein
                           organism = Borreliella burgdorferi
SEQUENCE: 33
MKNNKLIAIF LLHVLTVLIL ISCSLEVKDS NESKKHKKEK RKGKVENLLV AINNLKNPTK    60
PAAGKNKANS KASKQKNNPN ANANNAPKKI LDPEVAKLIQ KILDRSENII QISEMDSSRG   120
EPNDQFGMRA EIFSKIFFNA NSTVHFDSHE YTEERRMLYT SLNFNEGKIF NLGQILSKLS   180
QDSNYRGLVK ETLINRGFSI QLAMEEISAK ILNVKDKLQQ LNKPNLETLY NDFEKLTSLK   240
EKWLKDTDDL IDEYNTNPDL QTDVSKLNDT LRSKNSRAQF ANIHDIILDL VNTTTNILAP   300
IQ                                                                 302
```

```
SEQ ID NO: 34              moltype = AA   length = 411
FEATURE                    Location/Qualifiers
source                     1..411
                           mol_type = protein
                           organism = Borreliella burgdorferi
SEQUENCE: 34
MKIKPLIQLK LLGLFLFSCT IDANLNEDYK NKVKGILNKA ADDQETTSAD TNSNAAKNIP    60
IADNDKVAAE LKKQSQAAKT VAAAPNKGSQ NQPQTTPNKG SQNQQAAPSP QLQSLSFSAD   120
LSNLPKTTAA RAASLTKQRI PIQAVTTVPG NTRTFNSRNS GLPTFALNYS FSQPTRQQTN   180
SSSAVQTTTS SGSKLQTLKN ELIRAISEEK NKTQNNFGFR ETYDQFKMKD SAFELLDVIS   240
SAKVYDRSYA PQLNSNTPEA ENERNKFYAL MDFDQYKIEQ FGSIMEALYN ENQNHSLIRE   300
LMISGLGTQI SFELALEEIN KKIEIFNQDY LNAKINSFDF TMKLKELKSK LNQILDKRKE   360
WSRQADGLIA NASSNSSLSD SKSLAEYIKK RYLDNMQNAR QSVLEAYISI M            411

SEQ ID NO: 35              moltype = AA   length = 251
FEATURE                    Location/Qualifiers
source                     1..251
                           mol_type = protein
                           organism = Borreliella burgdorferi
SEQUENCE: 35
MKKAKLNIIK INIIAMILTL ICTSCAPFSK IDPKANANTK PKKITNPGEN TQNFEDKSGD    60
LSTSDEKIME TIASELKAIG KELEDQKKEE NIQIAKIAKE KFDFLSTFKV GPYDLIDEDI   120
QMKIKRTLYS SLDYKKENIE KLKEILEILK KNSEHYNIIG RLIYHISWGI QFQIEQNLEL   180
IQNGVENLSQ EESKSLLMQI KSNLEIKQRL KKTLNETLKV YNQNTQDNEK ILAEHFNKYY   240
KDFDTLKPAF Y                                                        251

SEQ ID NO: 36              moltype = AA   length = 257
FEATURE                    Location/Qualifiers
source                     1..257
                           mol_type = protein
                           organism = Borreliella burgdorferi
SEQUENCE: 36
MTKIFSNLII NGLLFGFVSL NVFADSNNAN ILKPQSNVLE HSDQKDNKKL DQKDQVNQAL    60
DTINKVTEDV SSKLEGVRES SLELVESNDA GVVKKFVGSM SLMSDVAKGT VVASQEATIV   120
AKCSGMVAEG ANKVVEMSKK AVQETQKAVS VAGEATFLIE KQIMLNKSPN NKELELTKEE   180
FAKVEQVKET LMASERALDE TVQEAQKVLN MVNGLNPSNK DQVLAKKDVA KAISNVVKVA   240
QGARDLTKVM AISLYMR                                                  257

SEQ ID NO: 37              moltype = AA   length = 365
FEATURE                    Location/Qualifiers
source                     1..365
                           mol_type = protein
                           organism = Borreliella burgdorferi
SEQUENCE: 37
MKEIGISIYP NVSPKNKIIK YLEKSAHFGF TQVFTSLLYI NGNEFDIFKE LLSIANKNGM    60
KPIIDVSPEI FKELGIDLSN LRNCPKLDYF KKLGAWAIRL DNTFTGIEES LMTFNDSDLK   120
IQLNISNINK HIDTIMYFKP NIKNLLGCHN FYPHKYTGLS RNFFKETTKI FKHYSIPTAA   180
FISSNNAEEC ARGKEKEGVP TLESHRSKDI ETQAKDLFKE GIDTVLISNC FPSETELKKV   240
SKVNRNILEL KADLNPDANS VEKEIILENL HFNRGDINSY RIRSTMPRVY YNNKKFPVHS   300
PNEIKKGDIL IDSSEYLGYT GELQIALKDT PNNGLVNVVG KIINDEIYLL EKIEPWEKFK   360
IIENK                                                               365

SEQ ID NO: 38              moltype = AA   length = 345
FEATURE                    Location/Qualifiers
source                     1..345
                           mol_type = protein
                           organism = Borreliella burgdorferi
SEQUENCE: 38
MKYLKNISLF LLILGCKSIP NGNFNLHDTN HKLGKLKFQE DSIISRNYDN KISIVGVYNP    60
LTEKENFKVN IFIKKKGLQI DPENILINEE KINYSKYKAE LKVKSSFNKS IISISLTNSR   120
DLLTYIYDKS TGKYINIDFK DNWNVSHSIK FNKEYILAYI TDFDKEIKIS KNILQKRIDN   180
RKIEIEKTEL KTEYNEIEDY YIYSMKIPKL FEKSDAPSET YETFVIANYY PCENLNILFL   240
NLSLYSDKLR FLNSIYDEND RKLKMEPPVR ALKNSKTIKE TLNIVLSPQK IIELAKNIEK   300
DITLKLKSYG EKGEFTFEIY KPLLLKFLKE VDHCIKNLQS SRHKF                   345

SEQ ID NO: 39              moltype = AA   length = 165
FEATURE                    Location/Qualifiers
source                     1..165
                           mol_type = protein
                           organism = Borreliella burgdorferi
SEQUENCE: 39
MILYQNQLKF LKLLVFFLLI SCTSLNVEHD QFGKTFRIYQ SLNKNAELKG IFNYKTGITK    60
IVLYTRFRNH SITEQNPLLL LDGTKIEGKV SYKRDNNHFF GNWINYSSFV LTKSLLERMI   120
KEEDASYKNK EVKIRIGLED LSLKKYKILD FLVMVESIEN KDYKS                   165
```

```
SEQ ID NO: 40           moltype = AA  length = 210
FEATURE                 Location/Qualifiers
source                  1..210
                        mol_type = protein
                        organism = Borreliella burgdorferi
SEQUENCE: 40
MKKNTLSAIL MTLFLFISCN NSGKDGNTSA NSADESVKGP NLTEISKKIT DSNAVLLAVK    60
EVEALLSSID EIAAKAIGKK IHQNNGLDTE NNHNGSLLAG AYAISTLIKQ KLDGLKNEGL   120
KEKIDAAKKC SETFTNKLKE KHTDLGKEGV TDADAKEAIL KTNGTKTKGA EELGKLFESV   180
EVLSKAAKEM LANSVKELTS PVVAESPKKP                                   210

SEQ ID NO: 41           moltype = AA  length = 175
FEATURE                 Location/Qualifiers
source                  1..175
                        mol_type = protein
                        organism = Borreliella burgdorferi
SEQUENCE: 41
MQKINIAKLI FILIFSLFVI SCELFIIKRR ATITETTTIE KKRINWLIMS VSGLNDEADE    60
VAFKHCREKI SLLKEDLKYA TNAKEFEEKF LNLQKLFQEK LTSKLNALKA VRVDIQRFNA   120
NDNDDLEKNK LKIRSIALSA GVNTSPIALH AINIKELSED VVAHIDSIIK YLEED        175

SEQ ID NO: 42           moltype = AA  length = 287
FEATURE                 Location/Qualifiers
source                  1..287
                        mol_type = protein
                        organism = Borreliella burgdorferi
SEQUENCE: 42
MQKDIYISNI FLYIPLFYSC FLTPPKSLKI NSIKTEVFDF KIIEEGDITK YNKNPIKESN    60
NNICLTFKEP ELNEIKEGEV FEILANGYVT WAKSGDLRDI KDKNNNLIED LRELKYSYIF   120
SPIRFKTYSL LTFSYTNYSI NDNNYKIFGQ EVPIAKIIAF ESTEEFEKKY EIKSLKLNSE   180
ESNIDFEQNR TGFAKINLKE TSREPQYIYS YNFGVFDNSL ADYFKLFYKK SKCNYMPAYL   240
TIKDKQTNKD KTYEIILNLK LFNDAIRLIF DKYSNLSKEK LKLFIDE                287

SEQ ID NO: 43           moltype = AA  length = 206
FEATURE                 Location/Qualifiers
source                  1..206
                        mol_type = protein
                        organism = Borreliella burgdorferi
SEQUENCE: 43
MGKILFFGLL LICIFLGFFF YKQKENNVIY NKIVEKFDDN VFVDETYTYL FKDSNLKELV    60
FIKSQLIIPE LKHKKMIKAT GYRADAYKAL STVYRFDFKV HDNKILGFKS VIFEGFEDAK   120
VSKHENNLPS EKWQQLKDFN IGDPNINEKF FHLEPFVVK NTLCVTISKG FFKKIKKLKR    180
LKIMLISNED REYKIDIENF LPKYNL                                       206

SEQ ID NO: 44           moltype = AA  length = 236
FEATURE                 Location/Qualifiers
source                  1..236
                        mol_type = protein
                        organism = Borreliella burgdorferi
SEQUENCE: 44
MKKSFLSIYM LISISLLSCD VSRLNQRNIN ELKIFVEKAK YYSIKLDAIY NECTGAYNDI    60
MTYSEGTFSD QSKVNQAISI FKKDNKIVNK FKELEKIIEE YKPMFLSKLI DDFAIELDQA   120
VDNDVSNARH VADSYKKLRK SVVLAYIESF DVISSKFVDS KPVEASKKFV NKAKEFVEEN   180
DLIALECIVK TIGDMVNDRE INSRSRYNNF YKKEADFLGA AVELEGAYKA IKQTLL       236

SEQ ID NO: 45           moltype = AA  length = 221
FEATURE                 Location/Qualifiers
source                  1..221
                        mol_type = protein
                        organism = Borreliella burgdorferi
SEQUENCE: 45
MKNNIILCMC VFLLLNSCTA NHEAEAKIKK HVDKTKNEYI NEIKNLIATT KEIIEKRKLL    60
QAKPVDQNPV DDTNNKKVFE IDKRAFDFIN SFLTDDEFNK FVTIFHKPTL KSPGKVLNSI   120
AILELNIEQV INHLDSKNET LNKASSLDLE KIKNSLEQLF SIRNFFSTII KRVLLDHQNN   180
ENSIKPDDSK SGTYFDTIYD QFNEKNKEVR NLKKTILSLP N                      221

SEQ ID NO: 46           moltype = AA  length = 278
FEATURE                 Location/Qualifiers
source                  1..278
                        mol_type = protein
                        organism = Borreliella burgdorferi
SEQUENCE: 46
MKNFKLNTIK LNVITAILTL ICISCAPFGN VNPNKLKNPI TSKNLKKTKR SNHSRNLKKT    60
NSHTNSENSA ENNQNLENES QNSKSSNQNP QEETAISKLE KIGKDLEAQK KEKDTQIEKI   120
SSDAQYDFLE NFKLHNYDYF MHNTKMTLKK IIYSSLNYEK EKILTLKEIL EKLDTEDNNR   180
RIAGGQFLETS RDIQLQQEDL ILKKIQDTLQ TLSKEKAEEL LQHAERDLKI KQNFVKALNA  240
TIEAYNKNSD NIKTDVEALA NHMEKKYSHP LYLLDQAD                          278
```

```
SEQ ID NO: 47           moltype = AA   length = 288
FEATURE                 Location/Qualifiers
source                  1..288
                        mol_type = protein
                        organism = Borreliella burgdorferi
SEQUENCE: 47
MKNFKLNIIK LNVITAILTS ICISCAPFGN VNPNEPKNPT TSKSLKKTKR SNNSRNLKNT    60
SNHTNSENLT GNSTKNPSEN NQNLENESQN SKSSNQNSQE ETTISKLKNI GKDLEAQKKK   120
EDTGITKMSK IDNAKYDFLE TFKLKQDDVF MFHAKMKLKR IIYPSLNYDT KKILVLKEIL   180
EKLDTEDNNR RIAGQFLETS RDIQLHLEDT YLKKIQDTLQ TLSEKEAEKL LQGVKLDLKK   240
KQNFAKSLNA TIDAYNKNVD NIKIDNKALA KHIKDKYSHP LYLLNQAD              288

SEQ ID NO: 48           moltype = AA   length = 204
FEATURE                 Location/Qualifiers
source                  1..204
                        mol_type = protein
                        organism = Borreliella burgdorferi
SEQUENCE: 48
MKIKFLTISL AILLANLIII LLNLVLFIVN TSTSSPYIVP SEKIDILHQS NTGAVKFKIS    60
LINHLGSVAI VYDYNSASER FYLDFEIVTN KKPFNLLDVS LNDVVIKPEV LLASNSKLRF   120
EEGQYVLNFD DSIEKTGFFV DLDLRNEYLN LAEIARISGI NFRVKCIERE TGVLRNVLFK   180
LSVEKGKKFF DLIERYNNNI GKVS                                        204

SEQ ID NO: 49           moltype = AA   length = 297
FEATURE                 Location/Qualifiers
source                  1..297
                        mol_type = protein
                        organism = Borreliella burgdorferi
SEQUENCE: 49
MRKSLFLYAL LMGGLMSCNL DSKLSSNKEQ KNNNNVKEVS DSVQEDGLND LYNNQEKQKS    60
FTKNFGERKY EDLINPIEPI IPSESPKNKA NIPNISIAHT EKKETKKENL IPSTNEEKEA   120
DAAIKYLEEN ILKNSKFSEL IREVRVIKDE YALIKADLYD VIGKINNKKT SLMENPKNNR   180
DKINKLTQLL QNNLKIDSEL EQLINMIDMA ENEISSAAFF FDNAQKRLKE SIIKRLESKN   240
NRSYALKLSR QALSDARSAL SNLESFASKR IEPMVRKEEI KELIKHAKTV LESLNKK     297

SEQ ID NO: 50           moltype = AA   length = 354
FEATURE                 Location/Qualifiers
source                  1..354
                        mol_type = protein
                        organism = Borreliella burgdorferi
SEQUENCE: 50
MKKVKSKYLA LGLLFGFISC DLFIRYEMKE ESPGLFDKGN SILETSEEST KKPMNKKGKG    60
KIARKKGKSK VSRKEPYIHS LKRDSANKSN FLQKNVILEE ESLKTELLKE QSETRKEKIQ   120
KQQDEYKGMT QGSLNSLSGE SGELEEPIES NEIDLTIDSD LRPKSSLQGI AGSNSISYTD   180
EIEEEDYDQY YLDEYDEEDE EEIRLSNRYQ SYLEGVKYNV DSAIQTITKI YNTYTLFSTK   240
LTQMYSTRLD NFAKAKAKEE AAKFTKEDLE KNFKTLLNYI QVSVKTAANF VYINDTHAKR   300
KLENIEAEIK TLIAKIKEQS NLYEAYKAIV TSILLMRDSL KEVQGIIDKN GVWY        354

SEQ ID NO: 51           moltype = AA   length = 285
FEATURE                 Location/Qualifiers
source                  1..285
                        mol_type = protein
                        organism = Borreliella burgdorferi
SEQUENCE: 51
MNLMIKVLIF SLFLSFISCK LYEAVDKSLI KDNKRSGRKA RSISYKEVNN QEQNNEKNLK    60
EAKESKKNNN LGIQKDGIVN TNPSVASDAS EKHTNRQPQQ VNNNSRETSE ARNIIQEIYT   120
SLEEVNKITT DLETIKSRLN NIKSKVDNAS SFLNNARKSN KANPTLLPKL DQAIRKVSSS   180
HAYANSNYSD AVSALKSSKH DFEYANRKAE DALQEALNNS NTQGYQYARY HYYMNDAKEA   240
MGRAKVSLKT AKQKQEKLKD KMDQANKEFE ELNKAHEAAL SSRES                 285

SEQ ID NO: 52           moltype = AA   length = 288
FEATURE                 Location/Qualifiers
source                  1..288
                        mol_type = protein
                        organism = Borreliella burgdorferi
SEQUENCE: 52
MNLINKLFIL TILFSSVISC KLYKKITYNA DQVIDKLKSN NGSFNTLKSN DDSKRSGRKP    60
RSVDNTYMDQ DTGKKPLMAD MQPDMQNDNS SSNHTLQVNI QDNEASEARN IMTEIESSKE   120
EYNRINEDLA KVKASLDKIK SLLSTAKSYL EQTRRGVGSS KANLALLPSL EEAIAKVKSN   180
HASADTHCND AIAALKRAKN DFEYAQRKAD RALEEALSNS NASRHESYYY AGYHQFMADA   240
KASMSSTKSL LEVAKNKQKE LNENMTKTNK DFQELNDIYK KLQDMDSR              288
```

| SEQ ID NO: 53 | moltype = AA   length = 332 |
|---|---|
| FEATURE | Location/Qualifiers |
| source | 1..332 |
| | mol_type = protein |
| | organism = Borreliella burgdorferi |

SEQUENCE: 53

```
MNLIIKVMLI SSLFSSFISC KLYEKLTNKS QQALAKAFVY DKDIADNKST NSTSKLDNSS   60
LDSIKDNNRS GRTSRALDDA EEIGVKESNQ NRNDQQQNNE SKVKESEKNN SSGIQADDSV  120
LDTAHSDASE VENKKHDTSR QPQLLNKDSS EAREASKIIQ KASTSLEEAE KVNAALKETR  180
SKLDKIKRLA DSAKSYLNNA RKNSRTNGSI LEILPNLDKA IEKAISSYAS LNVCYTDAIA  240
ALAKAKNDFE HAKRKANDAL EEALKDIPHF RGYNYLYHYR INNANDAMES AKSLLEVAKN  300
KQKELNENMT KTNKDFQELN DIYKKLQDMD SR                                332
```

| SEQ ID NO: 54 | moltype = AA   length = 282 |
|---|---|
| FEATURE | Location/Qualifiers |
| source | 1..282 |
| | mol_type = protein |
| | organism = Borreliella burgdorferi |

SEQUENCE: 54

```
MKKNIYILNI FLYIPLFYSC FLTPPKSSKI NSIKTEVLDF KIIEEGNIIK YDKKPIEERN   60
ENTCLSFKEP ELNEIKEGDV LELLAGGYVT WAKSGDLRVL KDKNNNLIED LRELRYSYIF  120
SPIRFKTFFS YNYSINDNNY KILGKKAPIV KIIAFESTKE FEKKYEINSL KLNSEESNID  180
FEQNRTGLAK INLKETSKEP NYIYSYNFGV FDNSLADYFK LFYKKNNCNY MPAYLTIKDK  240
ETDKYKTYEI ILNLKLFNDT IKLLINKYSN LSKEKLKLFT DE                     282
```

| SEQ ID NO: 55 | moltype = AA   length = 177 |
|---|---|
| FEATURE | Location/Qualifiers |
| source | 1..177 |
| | mol_type = protein |
| | organism = Borreliella burgdorferi |

SEQUENCE: 55

```
MEKFMNKKMK MFIICAVFIL IGACKIHTSY DEQSNGEVKV KKIEFSEFTV KIKNKNNSNN   60
WADLGDLVVR KEKDGIETGL NAGGHSATFF SLEEEEINNF IKAMTEGGSF KTSLYYGYND  120
EESDKNVIKN KEIKTKIEKI NDTEYITFLG DKINNSAGGD KIAEYAISLE ELKRNLK     177
```

| SEQ ID NO: 56 | moltype = AA   length = 160 |
|---|---|
| FEATURE | Location/Qualifiers |
| source | 1..160 |
| | mol_type = protein |
| | organism = Borreliella burgdorferi |

SEQUENCE: 56

```
MRNKNIFKLF FASMLFVMAC KAYVEEKKEI DSLMEDVLAL VNDSSGGKFK DYKDKINELK   60
ENLKDIGNAE LKEKLLNLQN SFQDKLAAKL AALKAAKNTI ENITDKDQDI SKRKIWSEAK  120
LVGVTVPLLG SNTSGNGDKM SKNAVEQIDK VIKFLEEGTN                        160
```

| SEQ ID NO: 57 | moltype = AA   length = 149 |
|---|---|
| FEATURE | Location/Qualifiers |
| source | 1..149 |
| | mol_type = protein |
| | organism = Borreliella burgdorferi |

SEQUENCE: 57

```
MKIINILFCL FLLLLNSCNS NDNDTLKNNA QQTKSRGKRD LTQKEATPEK PKSEELLRE    60
KLSEDQKTHL DWLKEALGND GEFDKFLGYD ESKIKSALNH IKSELDKCTG DNSEQQKSTF  120
KQTVQGFFSG GNIDNFANNA VSNCNNGGS                                    149
```

| SEQ ID NO: 58 | moltype = AA   length = 252 |
|---|---|
| FEATURE | Location/Qualifiers |
| source | 1..252 |
| | mol_type = protein |
| | organism = Borreliella burgdorferi |

SEQUENCE: 58

```
MNKKMFIICA IFALIVSCKN YASGEDVKKS LEQDLKGKVK GFLDTKKEEF FGDFKKPEAK   60
VQPKDEESMQ ADEPQEQGED QVVQGVAEDQ KLKEEIEQKI KELKDKIEKS DPKSVSLKTY  120
SDYEKEIEEL KEKLKDKEKF EKELEILEKA LNEKIEKRKK ELEESQKKFE ELKGQVESAI  180
GITDGERAKN QGKVGIEALR HARGLGFKNI SSGNSTSDIA KEIIVSSLKK IEEELEELKK  240
LEKESKDSNK KE                                                      252
```

| SEQ ID NO: 59 | moltype = AA   length = 186 |
|---|---|
| FEATURE | Location/Qualifiers |
| source | 1..186 |
| | mol_type = protein |
| | organism = Borreliella burgdorferi |

SEQUENCE: 59

```
MNKKMKMFIV CAVFILIGAC KIHTSYDEQS SGEINHTLYD EQSNGELKLK KIEFSKFTVK   60
IKNKDNNSNW TDLGDLVVRK EENGIDTGLN AGGHSATFFS LKESEVNNFI KAMTKGGSFK  120
TSLYYGKYE QSSANGIQNK EIITKIESIN GAEHIAFLGD KINNGVGGDK TAEYAIPLEV   180
LKKNLK                                                             186
```

```
SEQ ID NO: 60              moltype = AA   length = 343
FEATURE                    Location/Qualifiers
source                     1..343
                           mol_type = protein
                           organism = Borreliella burgdorferi
SEQUENCE: 60
MNKKTLIICA VFALIISCKN FATGKDIKQN SEGKIKGFVN KILDPVKDKI ASSGTKVDEV    60
AKKLQEEEKE ELMQGDDPNG SGINPPPVLP ENIHNNALVL KAIEQSDGQQ EKKVEEAEAK   120
VEENKEKQEN TEENIKEKEI IDEQNKQELA KAKEEEQQKE QKRHQEEQQR KAKAEKEKRE   180
REEAEQQKRQ QEEEKRQVD  NQIKTLIAKI DEINENEDVI KWQTTVGPQG VIDRITGPVY   240
DDFTNGNNSI RETWEGLEEE SEDEGLGKLL KELSDARDAL RTKLNEGNKP YTGYEEPKLK   300
ESVNVSEIKE DLEKLKSKLE EVKKYLKDSS KFEEIKGYIS DSQ                     343

SEQ ID NO: 61              moltype = AA   length = 229
FEATURE                    Location/Qualifiers
source                     1..229
                           mol_type = protein
                           organism = Borreliella burgdorferi
SEQUENCE: 61
MNKKMKMFII CAVFALMISC KNYASGENLK NSEQNLESSE QNVKKTEQEI KKQVEGFLEI    60
LETKDLSKLD EKDTKEIEKQ IQEELKNKIEK LDSKKTSIET YSEYEEKINK IKEKLKGKGL  120
EDKFKELEES LAKKKGERKK ALQEAKQKFE EYKKQVDTST GKTQGDRSKN RGGVGVQAWQ   180
CANELGLGVS YSNGGSDNSN TDELANKVID DSLKKIEEEL KGIEEDKKE               229

SEQ ID NO: 62              moltype = AA   length = 363
FEATURE                    Location/Qualifiers
source                     1..363
                           mol_type = protein
                           organism = Borreliella burgdorferi
SEQUENCE: 62
MNKKILIIFA VFALIISCKN YATGKDIKQN AKGKIKGFLD KVLDPAKDKI TSSSSKVDEL    60
AKKLQEEDED NELMQGDDPN NRAIALLPVL PENSHDNPPV PKVKAAAQSG GQQEDQKAKE   120
SKDKVEEEKE VVEEKKEEQD SKKEKVEKQS QKQKEEERNS KEEQKQEEA  KARADREREE   180
RLKQQEQKRQ QEEARVKAEK EKQEREEQQK QEEEKKVKYK IKTLTDKIDE INKDIDGING   240
KTIVGAEEVI DKITGPVYDD FTDGNKAIYK TWGDLEDEEG EELGKLLKEL SDTRHNLRTK   300
LNEGNKAYIV LEKEPNLKEN VNVSDIQSDL EKLKSGLEEV KKYFENEDNF EEIKGYIEDS   360
NSY                                                                 363

SEQ ID NO: 63              moltype = AA   length = 378
FEATURE                    Location/Qualifiers
source                     1..378
                           mol_type = protein
                           organism = Borreliella burgdorferi
SEQUENCE: 63
MNKKTIIICA VFALILSCKN YAIKDLEQNA KGKIKGFIDK ALDPAKDKIT SSSSKVDELA    60
RKLQEEDKIK GVEENNKDEL MQGDDPNSGV INSSPVLPEN SQDNTPILKA AEQSDGQQEE   120
KVKKVEESEA KVEGKEEKQE NTEERNKQEL AKQEEEQQKR KAEQEKQKRE EEQERQKREE   180
EQERKAKAEK EAKEKAERQK QEEQQKRKAE KEREEQRKEA EKRQVDNEIR TLTGKIDEIN   240
RNIDVIKEQT SVGAQGVIDR ITGPVYDDFT DGNKAIYKTW GDLEDDNDEG LGKLLKELSD   300
TRHNLRTKLN EGNKAYIIDT RSTEPQLKEN VSVSEIKSDL DELKSKLEEV KEYLEDKDNF   360
EEIKEYVAGS EDNYDEED                                                 378

SEQ ID NO: 64              moltype = AA   length = 345
FEATURE                    Location/Qualifiers
source                     1..345
                           mol_type = protein
                           organism = Borreliella burgdorferi
SEQUENCE: 64
MNKKMKIFII CAVFVLISSC KIDATGKDAT GKDATGKDAT GKDATGKNAE QNIKGKVQGF    60
LEKILDPVKD KIASNGPIAD ELAKKLQEEE KVNNGEEEND KAVFLGEESK EDEEENEQAV   120
NLEEKNAEED KKVVNLEEKE LEVKKETEED EDKEEIEKQK QEVEKAQERK QRQEEKKRKK   180
QEQQEEKKRK RQEQRKERRA KNKIKKLADK IDEISWNIDG IESQTSVPK  AVIDKITGPV   240
YDYFTDDNKK AIYKTWGDLE DEEGEGLGKL LKELSDTRDE LRTKLNKDNK KYYAHENEPP   300
LKENVDVSEI KEDLEKVKSG LEKVKEYLKD NSKFEEIKGY ISYSQ                   345

SEQ ID NO: 65              moltype = AA   length = 140
FEATURE                    Location/Qualifiers
source                     1..140
                           mol_type = protein
                           organism = Borreliella burgdorferi
SEQUENCE: 65
MKIINILFCL FLLMLNGCNS NDTNNSQTKS RQKRDLTQKE ATQEKPKSKE ELLREKLNDN    60
QKTHLDWLKE ALGNDEFNK  FLGYDESKIK SALDHIKSEL DSCTGDKVEN KNTFKQVVQE   120
ALKGGIDGFE NTASSTCKNS                                               140
```

```
SEQ ID NO: 66          moltype = AA   length = 224
FEATURE                Location/Qualifiers
source                 1..224
                       mol_type = protein
                       organism = Borreliella burgdorferi
SEQUENCE: 66
MNKKIKMFII CAIFMLISSC KNDVTSKDLE GAVKDLESSE QNVKKTEQEI KKQVEGFLEI   60
LETKDLNTLD TKEIEKQIQE LKNKIEKLDS KKTSIETYSG YEEKINKIKE KLNGKGLEDK  120
LNELSESLKK KKEERKKALQ EAKKKFEEYK NQAESATGVT HGSQVQRQGG VGLQAWQCAN  180
SLGFKNMTSG NNTSDMTNEV ITNSLKKIEE ELKNIGETVE GKKE                   224

SEQ ID NO: 67          moltype = AA   length = 148
FEATURE                Location/Qualifiers
source                 1..148
                       mol_type = protein
                       organism = Borreliella burgdorferi
SEQUENCE: 67
MKIINILFCL FLLMLNGCNS NDNDTLKNNA QQTKRRGKRD LTQKETTQEK PKSKEELLRE   60
KLSDDQKTHL DWLKPALTGA GEFDKFLEND DDKIKSALDH IKTQLDSCNG DQAEQQKTTF  120
KTVVTEFFKN GDIDNFATGA VSNCNNGG                                     148

SEQ ID NO: 68          moltype = AA   length = 196
FEATURE                Location/Qualifiers
source                 1..196
                       mol_type = protein
                       organism = Borreliella burgdorferi
SEQUENCE: 68
MNKKMKNLII CAVFVLIISC KIDASSEDLK QNVKEKVEGF LDKELMQGDD PNNSLFNPPP   60
VLPASSHDNT PVLKAVQAKD GGQQEGKEEK EKEIQELKDK IDKRKKELEE ARKKFQEFKE  120
QVESATGEST EKVKKQGNIG QKALKYAKEL GVNGSYSVND GTNTNDFVKK VIDDALKNIE  180
EELEKLAEPQ NIEDKK                                                  196

SEQ ID NO: 69          moltype = AA   length = 90
FEATURE                Location/Qualifiers
source                 1..90
                       mol_type = protein
                       organism = synthetic construct
SEQUENCE: 69
LESSSKDLKN KILKIKKEAT GKGVLFEAFT GLKTGSKVTS GGLALNNPIN TAERLLAAKA   60
QIENQLKVVK EKQNIENGGE KKNNKSKKKK                                    90

SEQ ID NO: 70          moltype = AA   length = 200
FEATURE                Location/Qualifiers
source                 1..200
                       mol_type = protein
                       organism = synthetic construct
SEQUENCE: 70
NTEAISELQS SPIKLGKIKV LQKTEKIVST QNLQNLQQSQ FFKNEKEKII KKIAQEFDEN   60
EKLINKIGPN IEMFAQTINT DIQKIEPNDQ FGINKTLFTE KKDNNIDFML KDNRLRRLFY  120
SSLNYDENKI KKLATILAQT SSSNDYHYTL IGLIFWTGFK IQEAFESAVN ILTKDEQKRL  180
IFNFRTKTVK EIQENFEKLM                                              200

SEQ ID NO: 71          moltype = AA   length = 145
FEATURE                Location/Qualifiers
source                 1..145
                       mol_type = protein
                       organism = synthetic construct
SEQUENCE: 71
DKQKELAIFY YEVGQRYINV GKIKKGKLFQ AKALKIYPDL KKGFDIKLAV KELDARIKDD   60
NPKVVSTLSS ASSKADADEL EYLSVDDYYD LKSLKISKSN DTSFAVNVNA KKNDVTKNFP  120
FWKERQTLIF TTEDDNNWFL SSINF                                        145

SEQ ID NO: 72          moltype = AA   length = 90
FEATURE                Location/Qualifiers
source                 1..90
                       mol_type = protein
                       organism = synthetic construct
SEQUENCE: 72
NKFFLDLGSE QSKDLIKLFI MVKNEQNNNK FMRIVRWLYS CIEELYSLDI KYSGEGSHEY   60
NRNMPRPTAY EQYLKVKRYD YNSPVSILPT                                    90
```

```
SEQ ID NO: 73            moltype = AA  length = 525
FEATURE                  Location/Qualifiers
source                   1..525
                         mol_type = protein
                         organism = unidentified
SEQUENCE: 73
LESSSKDLKN KILKIKKEAT GKGVLFEAFT GLKTGSKVTS GGLALNNPIN TAERLLAAKA   60
QIENQLKVVK EKQNIENGGE KKNNKSKKKK NTEAISELQS SPIKLGKIKV LQKTEKIVST  120
QNLQNLQQSQ FFKNEKEKII KKIAQEFDEN EKLINKIGPN IEMFAQTINT DIQKIEPNDQ  180
FGINKTLFTE KKDNNIDFML KDNRLRRLFY SSLNYDENKI KKLATILAQT SSSNDYHYTL  240
IGLIFWTGFK IQEAFESAVN ILTKDEQKRL IFNFRTKTVK EIQENFEKLM DKQKELAIFY  300
YEVGQRYINV GKIKKGKLFQ AKALKIYPDL KKGFDIKLAV KELDARIKDD NPKVVSTLSS  360
ASSKADADEL EYLSVDDYYD LKSLKISKSN DTSFAVNVNA KKNDVTKNFP FWKERQTLIF  420
TTEDDNNWFL SSINFNKFFL DLGSEQSKDL IKLFIMVKNE QNNNKFMRIV RWLYSCIEEL  480
YSLDIKYSGE GSHEYNRNMP RPTAYEQYLK VKRYDYNSPV SILPT                 525

SEQ ID NO: 74            moltype = AA  length = 6
FEATURE                  Location/Qualifiers
source                   1..6
                         mol_type = protein
                         organism = synthetic construct
SEQUENCE: 74
HHHHHH                                                              6

SEQ ID NO: 75            moltype = AA  length = 5
FEATURE                  Location/Qualifiers
source                   1..5
                         mol_type = protein
                         organism = synthetic construct
SEQUENCE: 75
DDDDK                                                               5

SEQ ID NO: 76            moltype = AA  length = 155
FEATURE                  Location/Qualifiers
source                   1..155
                         mol_type = protein
                         organism = synthetic construct
SEQUENCE: 76
LESSSKDLKN KILKIKKEAT GKGVLFEAFT GLKTGSKVTS GGLALREAKV QAIVETGKFL   60
KIIEEEALKL KETGNSGQFL AMFDLMLEVV ESLEDVGIIG LKARVLEESK NNPINTAERL  120
LAAKAQIENQ LKVVKEKQNI ENGGEKKNNK SKKKK                             155
```